US009045391B2

(12) United States Patent
Moerbe et al.

(10) Patent No.: US 9,045,391 B2
(45) Date of Patent: *Jun. 2, 2015

(54) PROCESS FOR MAKING NITRILES

(75) Inventors: Larry E. Moerbe, Orange, TX (US); Tseng H. Chao, Beaumont, TX (US)

(73) Assignee: INVISTA North America S.a.r.l., Wilmington, DE (US)

( * ) Notice: Subject to any disclaimer, the term of this patent is extended or adjusted under 35 U.S.C. 154(b) by 74 days.

This patent is subject to a terminal disclaimer.

(21) Appl. No.: 13/808,674

(22) PCT Filed: Jun. 16, 2011

(86) PCT No.: PCT/US2011/040644
§ 371 (c)(1),
(2), (4) Date: Jan. 28, 2013

(87) PCT Pub. No.: WO2012/005910
PCT Pub. Date: Jan. 12, 2012

(65) Prior Publication Data
US 2013/0211121 A1  Aug. 15, 2013

Related U.S. Application Data

(60) Provisional application No. 61/362,175, filed on Jul. 7, 2010.

(51) Int. Cl.
*C07C 253/10* (2006.01)

(52) U.S. Cl.
CPC .................................. *C07C 253/10* (2013.01)

(58) Field of Classification Search
None
See application file for complete search history.

(56) References Cited

U.S. PATENT DOCUMENTS

| | | |
|---|---|---|
| 3,361,191 A | 1/1968 | Goble |
| 3,496,215 A | 2/1970 | Drinkard et al. |
| 3,496,217 A | 2/1970 | Drinkard, Jr. et al. |
| 3,536,748 A | 10/1970 | Drinkard, Jr. et al. |
| 3,655,723 A | 4/1972 | Drinkard, Jr. |
| 3,766,237 A | 10/1973 | Chia et al. |
| 3,773,809 A | 11/1973 | Walter |
| 3,852,329 A | 12/1974 | Tomlinson |
| 3,903,120 A | 9/1975 | Shook, Jr. et al. |
| 4,385,007 A | 5/1983 | Shook, Jr. |
| 4,416,825 A | 11/1983 | Ostermaier |
| 4,547,619 A | 10/1985 | Diaz |
| 4,874,884 A | 10/1989 | McKinney et al. |
| 5,512,696 A | 4/1996 | Kreutzer et al. |
| 5,688,986 A | 11/1997 | Tam et al. |
| 5,821,378 A | 10/1998 | Foo et al. |
| 5,959,135 A | 9/1999 | Garner et al. |
| 5,981,772 A | 11/1999 | Foo et al. |
| 6,020,516 A | 2/2000 | Foo et al. |
| 6,127,567 A | 10/2000 | Garner et al. |
| 6,169,198 B1 | 1/2001 | Fischer et al. |
| 6,197,992 B1 | 3/2001 | Fischer et al. |
| 6,242,633 B1 | 6/2001 | Fischer et al. |
| 6,355,833 B2 | 3/2002 | Fischer et al. |
| 6,521,778 B1 | 2/2003 | Fischer et al. |
| 6,770,770 B1 | 8/2004 | Baumann et al. |
| 6,812,352 B2 | 11/2004 | Kreutzer et al. |
| 6,852,199 B2 | 2/2005 | Jungkamp et al. |
| 6,893,996 B2 | 5/2005 | Chu et al. |
| 6,936,171 B2 | 8/2005 | Jackson et al. |
| 7,022,866 B2 | 4/2006 | Bartsch et al. |
| 7,067,685 B2 | 6/2006 | Bartsch et al. |
| 7,084,294 B2 | 8/2006 | Jungkamp et al. |
| 7,345,006 B2 | 3/2008 | Bartsch et al. |
| 7,361,778 B2 | 4/2008 | Bartsch et al. |
| 7,407,643 B2 | 8/2008 | Jungkamp et al. |
| 7,439,381 B2 | 10/2008 | Jungkamp et al. |
| 7,462,263 B2 | 12/2008 | Bartsch et al. |
| 7,504,529 B2 | 3/2009 | Jungkamp et al. |
| 7,521,575 B2 | 4/2009 | Bartsch et al. |
| 7,528,275 B2 | 5/2009 | Bartsch et al. |
| 7,538,240 B2 | 5/2009 | Jungkamp et al. |
| 7,541,486 B2 | 6/2009 | Scheidel et al. |
| 7,550,407 B2 | 6/2009 | Bartsch et al. |
| 7,566,800 B2 | 7/2009 | Scheidel et al. |
| 7,612,224 B2 | 11/2009 | Scheidel et al. |
| 7,671,229 B2 | 3/2010 | Bartsch et al. |
| 7,700,795 B2 | 4/2010 | Haderlein et al. |
| 7,705,171 B2 | 4/2010 | Haderlein et al. |
| 7,709,675 B2 | 5/2010 | Bartsch et al. |

(Continued)

FOREIGN PATENT DOCUMENTS

| | | |
|---|---|---|
| EP | 1344770 | 9/2003 |
| EP | 1438133 A1 | 7/2004 |

(Continued)

OTHER PUBLICATIONS

Tolman, et al., Advances in Catalysis, 1985, vol. 33, pp. 1-46.
Coutinho, "Nylon Intermediates Refining", PhD thesis dissertation, Dec. 2001.
Written Opinion for PCT/US2011/040678 dated Jun. 7, 2012.
Written Opinion for PCT/US2011/040688 dated Jun. 7, 2012.
Written Opinion for PCT/US2011/040676 dated Jun. 7, 2012.
Written Opinion for PCT/US2011/040664 dated Jun. 7, 2012.
Written Opinion for PCT/US2011/040670 dated Jun. 7, 2012.
Written Opinion for PCT/US2011/040660 dated Jun. 7, 2012.
Written Opinion for PCT/US2011/040651 dated Jun. 7, 2012.
Written Opinion for PCT/US2011/040656 dated Jun. 7, 2012.
Written Opinion for PCT/US2011/040644 dated Jun. 7, 2012.

(Continued)

*Primary Examiner* — Michael Barker
*Assistant Examiner* — Po-Chih Chen
(74) *Attorney, Agent, or Firm* — Robert B. Furr, Jr.; Edward F. Kenehan, Jr.

(57) ABSTRACT

Adiponitrile is made by reacting 3-pentenenitrile with hydrogen cyanide. The 3-pentenenitrile is made by reacting 1,3-butadiene with hydrogen cyanide. The catalyst for the reaction of 1,3-butadiene with hydrogen cyanide to make 3-pentenenitrile is recycled. At least a portion of the recycled catalyst is purified by an extraction process, which separates catalyst degradation products and reaction byproduct from the catalyst.

22 Claims, 4 Drawing Sheets

(56) References Cited

U.S. PATENT DOCUMENTS

| | | |
|---|---|---|
| 7,777,068 B2 | 8/2010 | Bartsch et al. |
| 7,781,608 B2 | 8/2010 | Scheidel et al. |
| 7,816,551 B2 | 10/2010 | Jungkamp et al. |
| 7,851,656 B2 | 12/2010 | Baumann et al. |
| 7,935,229 B2 | 5/2011 | Deckert et al. |
| 8,058,466 B2 | 11/2011 | Haderlein et al. |
| 8,278,474 B2 | 10/2012 | Jungkamp et al. |
| 8,410,299 B2 | 4/2013 | Jungkamp et al. |
| 2004/0176622 A1 | 9/2004 | Bartsch et al. |
| 2007/0155978 A1 | 7/2007 | Jungkamp et al. |
| 2007/0260086 A1 | 11/2007 | Rosier et al. |
| 2008/0221351 A1 | 9/2008 | Bartsch et al. |
| 2008/0281120 A1 | 11/2008 | Jungkamp et al. |
| 2009/0099386 A1 | 4/2009 | Leconte et al. |
| 2011/0196168 A1 | 8/2011 | Ostermaier |
| 2011/0311428 A1 | 12/2011 | Ostermaier |
| 2013/0143730 A1 | 6/2013 | Fraga-Dubreuil et al. |
| 2013/0144079 A1 | 6/2013 | Medhekar et al. |
| 2013/0144082 A1 | 6/2013 | Fraga-Dubreuil et al. |
| 2013/0150610 A1 | 6/2013 | Moerbe et al. |
| 2013/0211122 A1 | 8/2013 | Moerbe et al. |
| 2013/0211123 A1 | 8/2013 | Moerbe et al. |
| 2013/0211124 A1 | 8/2013 | Moerbe et al. |
| 2013/0211125 A1 | 8/2013 | Moerbe et al. |
| 2013/0211126 A1 | 8/2013 | Moerbe et al. |
| 2013/0211127 A1 | 8/2013 | Moerbe et al. |
| 2013/0267728 A1 | 10/2013 | Moerbe et al. |

FOREIGN PATENT DOCUMENTS

| | | |
|---|---|---|
| EP | 1603865 A1 | 12/2005 |
| EP | 1682269 A1 | 7/2006 |
| EP | 1682270 A2 | 7/2006 |
| EP | 1716107 A1 | 11/2006 |
| EP | 1713816 B1 | 8/2007 |
| EP | 2007491 A2 | 12/2008 |
| EP | 1799697 B1 | 3/2012 |
| EP | 2556050 A1 | 2/2013 |
| WO | 9511077 | 4/1995 |
| WO | 2012005910 | 1/2012 |
| WO | 2012005911 | 1/2012 |
| WO | 2012005912 | 1/2012 |
| WO | 2012005913 | 1/2012 |
| WO | 2012005915 | 1/2012 |
| WO | 2012005916 | 1/2012 |
| WO | 2012005917 | 1/2012 |
| WO | 2012005918 | 1/2012 |
| WO | 2012005919 | 1/2012 |

OTHER PUBLICATIONS

International Search Report Received for PCT Patent Application No. PCT/US2011/040644, mailed on Oct. 6, 2011, 4 pages.

Written Opinion Received for PCT Patent Application No. PCT/US2011/040644, mailed on Oct. 6, 2011, 5 pages.

International Preliminary Report on Patentability received for PCT Patent Application No. PCT/US2011/040644, mailed on Oct. 22, 2012, 16 pages.

PROCESS FOR MAKING NITRILES

CROSS-REFERENCE TO RELATED APPLICATION

This application is a 371 application of PCT/US11/40644, filed on Jun. 16, 2011, which claims the benefit of U.S. Provisional Application No. 61/362,175, filed Jul. 7, 2010.

FIELD OF THE INVENTION

This disclosure relates to a process for manufacturing nitriles. More particularly, the disclosure relates to an improved multi-reaction zone process to provide for improved nitrile product quality and yield. In a first reaction zone, 1,3-butadiene is reacted with hydrogen cyanide in the presence of a catalyst to produce pentenenitriles comprising 3-pentenenitrile and 2-methyl-3-butenenitrile. In a second reaction zone, 2-methyl-3-butenenitrile, recovered from the first reaction zone, is isomerized to 3-pentenenitrile. In a third reaction zone, 3-pentenenitrile recovered from the first and second reaction zones is reacted with hydrogen cyanide in the presence of a catalyst and a Lewis acid to produce adiponitrile. Catalysts for the first and third reaction zones are separately recycled and the transfer of catalysts between the first and third reaction zones is limited.

BACKGROUND OF THE INVENTION

Adiponitrile (ADN) is a commercially important and versatile intermediate in the industrial production of nylon polyamides useful in forming films, fibers, and molded articles. ADN may be produced by hydrocyanation of 1,3-butadiene (BD) in the presence of transition metal complexes comprising various phosphorus-containing ligands. For example, catalysts comprising zero-valent nickel and monodentate phosphorus-containing ligands are well documented in the prior art; see, for example, U.S. Pat. Nos. 3,496,215; 3,631,191; 3,655,723 and 3,766,237; and Tolman, C. A., McKinney, R. J., Seidel, W. C., Druliner, J. D., and Stevens, W. R., Advances in Catalysis, 1985, Vol. 33, pages 1-46. Improvements in the hydrocyanation of ethylenically unsaturated compounds with catalysts comprising zero-valent nickel and certain multidentate phosphite ligands are also disclosed; e.g., see: U.S. Pat. Nos. 5,512,696; 5,821,378; 5,959,135; 5,981,772; 6,020,516; 6,127,567; and 6,812,352.

3-Pentenenitrile (3PN) may be formed through a series of reactions as illustrated below.

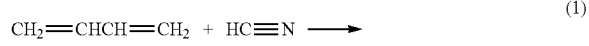
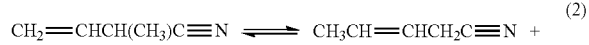
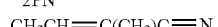
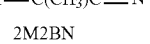

According to abbreviations used herein, BD is 1,3-butadiene, HC≡N is hydrogen cyanide, and 2M3BN is 2-methyl-3-butenenitrile. A method to increase the chemical yield of 3PN from BD hydrocyanation includes the catalytic isomerization of 2M3BN to 3PN (Equation 2 above) in the presence of $NiL_4$ complexes as disclosed in U.S. Pat. No. 3,536,748. Co-products of BD hydrocyanation and 2M3BN isomerization may include 4-pentenenitrile (4PN), 2-pentenenitrile (2PN), 2-methyl-2-butenenitrile (2M2BN), and 2-methylglutaronitrile (MGN).

In the presence of transition metal complexes comprising various phosphorus-containing ligands, dinitriles such as ADN, MGN, and ethylsuccinonitrile (ESN) may be formed by the hydrocyanation of 3PN and 2M3BN, as illustrated in Equations 3 and 4 below. Equation 4 also shows that 2M2BN can be formed when 2M3BN undesirably isomerizes in the presence of a Lewis acid promoter that may be carried over from a pentenenitrile hydrocyanation reaction zone.

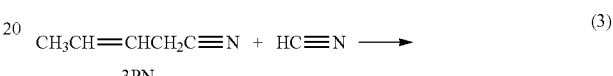
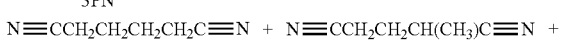
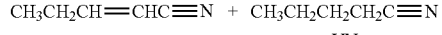
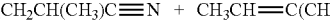

The hydrocyanation of activated olefins such as conjugated olefins (e.g., 1,3-butadiene) can proceed at useful rates without the use of a Lewis acid promoter. However, the hydrocyanation of un-activated olefins, such as 3PN, require at least one Lewis acid promoter to obtain industrially useful rates and yields for the production of linear nitriles, such as ADN. For example, U.S. Pat. Nos. 3,496,217, 4,874,884, and 5,688,986 disclose the use of Lewis acid promoters for the hydrocyanation of non-conjugated ethylenically unsaturated compounds with nickel catalysts comprising phosphorous-containing ligands.

An integrated process for the production of ADN from BD and HC≡N can comprise BD hydrocyanation, 2M3BN isomerization to produce 3PN, and the hydrocyanation of pentenenitriles, including 3PN, to produce ADN and other dinitriles. Integrated processes are disclosed, for example, in United States Patent Application 2009/0099386 A1.

Disclosed in United States Patent Publication No. 2007/0260086, is a process for the preparation of dinitriles with an aim to provide for the recovery of a catalyst formed by a mixture of mono- and bidentate ligands and to be able to reuse the catalyst thus recovered in the hydrocyanation and/or isomerization stages.

United States Patent Publication No. 2008/0221351 discloses an integrated process for preparing ADN. A first process step includes hydrocyanating BD to produce 3PN over at least one zero-valent nickel catalyst. A second process step of the integrated process involves hydrocyanating 3PN to produce ADN over at least one zero-valent nickel catalyst and at least one Lewis acid. In this integrated process, at least one of the zero-valent nickel catalysts used in one of the process steps is transferred into the other process step.

In order to optimize the use of catalyst, recycle of catalyst is desirable. However, undesirable substances, such as catalyst degradation products and reaction byproducts, may end up in catalyst recycle loops along with catalyst. When such catalyst degradation products and reaction byproducts are recycled along with catalysts, they tend to build up and cause loss of product yield and purity. Accordingly, there is a need to recycle catalysts, while retaining optimal product yield and purity.

SUMMARY OF THE INVENTION

Buildup of catalyst degradation products and reaction byproducts is reduced by using separate catalyst recycle loops for recycling a catalyst used for hydrocyanating 1,3-butadiene and a catalyst used for hydrocyanating 3-pentenenitrile. A portion of the catalyst used for hydrocyanating 1,3-butadiene is purified in a liquid/liquid extraction treatment.

Pentenenitrile is made in a process comprising two steps. In the first step [i.e. step (a)], 1,3-butadiene is reacted with hydrogen cyanide in a first reaction zone ($Z_1$) in the presence of a first catalyst comprising zero-valent nickel ($Ni^0$) and a first phosphorus-containing ligand to produce a reactor effluent comprising 3-pentenenitrile (3PN) and 2-methyl-3-butenenitrile (2M3BN). In the second step [i.e. step (b)], at least a portion of the 2M3BN made in the first step is isomerized in a second reaction zone ($Z_2$) in the presence of a second catalyst comprising zero-valent nickel ($Ni^0$) and a second phosphorus-containing ligand to produce a reaction product comprising 3PN.

An effluent stream comprising 3PN may be recovered from the second reaction zone ($Z_2$). 3PN may also be recovered by distillation of the reaction product from the first reaction zone ($Z_1$). The recovered 3PN may be contacted with HCN in a third reaction step [i.e. step (c)] in a third reaction zone ($Z_3$) in the presence of a third catalyst, comprising zero-valent nickel ($Ni^0$) and a third phosphorus-containing ligand. The reaction in the third reaction zone ($Z_3$) takes place in the presence of Lewis acid promoter.

Catalyst introduced into a reaction zone flows into, through and out of the reaction zone along with reactants and products. Any Lewis acid promoter introduced into a reaction zone also flows through the reaction zone along with the flow of reactants, products and catalyst. The catalyst which flows through the first reaction zone is also referred to herein as the first catalyst. This first catalyst comprises zero valent nickel and a first phosphorus-containing ligand. The catalyst which flows through the second reaction zone is also referred to herein as the second catalyst. This second catalyst comprises zero valent nickel and a second phosphorus-containing ligand.

The first reaction zone is substantially free of Lewis acid promoter. The flow of recycled catalyst is controlled to avoid the introduction of Lewis acid promoter, which flows through the third reaction zone ($Z_3$), into the first reaction zone ($Z_1$).

In addition to 3-pentenenitrile (3PN) and 2-methyl-3-butenenitrile (2M3BN), the reaction product of step (a) further comprises dinitriles. These dinitriles comprise adiponitrile (ADN) and methylglutaronitrile (MGN). Adiponitrile (ADN) may be formed by the reaction of 3-pentenenitrile (3PN) with HCN. Methylglutaronitrile (MGN) may be formed by the reaction of 2-methyl-3-butenenitrile (2M3BN) with HCN.

The formation of MGN in the first reaction zone ($Z_1$) is especially problematic in that 2M3BN is converted before it can be recovered and isomerized into 3PN. In a process where 3PN is recovered and reacted with HCN to form ADN, the production of one mole of MGN in the first reaction zone ($Z_1$) results in a loss of two moles of HCN and one mole of BD, which could otherwise be converted to ADN. Accordingly, unwanted production of MGN in the first reaction zone ($Z_1$) results in unwanted reduction of ADN yield, based on moles of HCN and BD reacted.

As catalyst flows through the first and second reaction zones, the zero valent nickel content of the catalyst may be reduced and catalyst degradation byproducts may be produced. These catalyst degradation byproducts comprise oxidized forms of nickel, oxidized forms of ligand and hydrolyzed forms of ligand.

At least a portion of the catalyst flowing from the first reaction zone along with products or at least a portion of the catalyst flowing from the second reaction zone along with products or at least a portion of the catalyst flowing from both of the first and second reaction zones along with products is concentrated and recycled to the first reaction zone or the second reaction zone or both the first and second reaction zones. Concentration of catalyst flowing from the first reaction zone may take place in one or more distillation steps. Similarly, concentration of the catalyst flowing from or the second reaction zone may take place in one or more distillation steps.

In one embodiment, at least a portion of the catalyst flowing from the first reaction zone along with products is concentrated and recycled to the first reaction zone. In another embodiment, at least a portion of the catalyst flowing from the second reaction zone along with products is concentrated and recycled to the first reaction zone. In another embodiment, at least a portion of the catalyst flowing from both of the first and second reaction zones along with products is concentrated and recycled to the first reaction zone. In another embodiment, at least a portion of the catalyst flowing from the first reaction zone along with products is concentrated and recycled to the second reaction zone. In another embodiment, at least a portion of the catalyst flowing from the second reaction zone along with products is concentrated and recycled to the second reaction zone. In another embodiment, at least a portion of the catalyst flowing from both of the first and second reaction zones along with products is concentrated and recycled to the first reaction zone. In another embodiment, at least a portion of the catalyst flowing from both of the first and second reaction zones along with products is concentrated and recycled to both the first and second reaction zones.

Catalyst is especially concentrated in column bottoms of columns used to concentrate catalyst. Dinitriles produced in the first reaction zone ($Z_1$) or recycled into this first reaction zone ($Z_1$) also become concentrated in column bottoms of columns used to concentrate catalyst. Catalysts tend to be less thermally stable in solutions with high concentrations of these dinitriles, as opposed to catalyst solutions with high concentrations of mononitriles, such as 3PN and 2M3BN. When the production or build-up of dinitriles is excessively high, nickel/ligand complex of the catalyst may lack thermal stability and may break down releasing free ligand and non-complexed nickel in column bottoms, where the nickel/ligand complex is exposed to the highest temperatures. Nickel which is not complexed to ligand becomes insoluble and may plate out on high temperature surfaces such as exchange tubes and column walls, which, in turn, creates a host of problems including loss of active catalyst and loss of throughput capacity, ultimately requiring shut down of production.

At least two, and, optionally, three separate liquid/liquid extraction steps are used to purify or regenerate catalysts. At least a portion of the concentrated catalyst from the first reaction zone is purified by removing catalyst degradation byproducts and reaction byproducts in a first liquid/liquid extraction step. A separate liquid/liquid extraction step is used to treat the product from the third reaction zone. Purified catalyst from the first liquid/liquid extraction step is recycled to the first reaction zone. Optionally, when the first catalyst and the second catalyst are the same, a portion of this purified catalyst may be recycled to the second reaction zone. Optionally, three separate liquid/liquid extraction sections are used for each catalyst. As used herein, the terms "extraction section" and "extraction zone" refer to the equipment and process steps for metering, charging, mixing, holding, separating and recycling components of a liquid-liquid extraction process. According to the option of using three separate extraction sections or zones, a portion of the first catalyst is extracted in a first liquid/liquid extraction zone, a portion of the second catalyst is extracted in a second liquid/liquid extraction zone, and at least a portion, for example, all, of the third catalyst is extracted in a third liquid/liquid extraction zone. These three zones have dedicated equipment for extraction, and equipment in different zones is not shared.

The first liquid/liquid extraction step comprises introducing a portion of the catalyst recycle stream, a first extraction solvent stream and a dinitrile recycle stream comprising adiponitrile (ADN) into a first liquid/liquid extraction zone. The first liquid/liquid extraction step further comprises separating the liquids in the first liquid/liquid extraction zone into a first solvent phase and a first raffinate phase. The first solvent phase comprises extraction solvent and catalyst. The first raffinate phase comprises adiponitrile (ADN), methylglutaronitrile (MGN), compounds with a higher boiling point than adiponitrile (ADN) and compounds with a lower boiling point than methylglutaronitrile (MGN).

Catalyst from the first solvent phase obtained in the first liquid/liquid extraction step is recycled to the first reaction zone. Optionally, when the first and second phosphorus-containing ligands are the same, a portion of this purified catalyst may be recycled to the second reaction zone.

The first raffinate phase may be distilled in one or more distillation steps to separate adiponitrile (ADN) and methylglutaronitrile (MGN) from compounds with a higher boiling point than adiponitrile (ADN) and compounds with a lower boiling point than methylglutaronitrile (MGN) to obtain a first refined dinitrile stream. The first refined dinitrile stream may be further distilled to remove methylglutaronitrile (MGN) from the first refined dinitrile stream to obtain a second refined dinitrile stream enriched in adiponitrile. At least a portion of the second refined dinitrile stream is recycled to the first liquid/liquid extraction step as a dinitrile recycle stream.

The third catalyst is not contacted with the first extraction solvent in the first liquid/liquid extraction step used to purify the first catalyst.

The presence of Lewis acid promoter in the third reaction zone ($Z_3$) promotes the reaction of 3-pentenenitrile (3PN) with HCN to produce adiponitrile (ADN). However, the presence of Lewis acid promoter in the first reaction zone ($Z_1$) promotes both the reaction of 3-pentenenitrile (3PN) with HCN to produce adiponitrile (ADN) and the reaction of 2-methyl-3-butenenitrile with HCN to produce methylglutaronitrile (MGN). In the event that Lewis acid is introduced into the first reaction zone ($Z_1$), the amount of Lewis acid promoter in the first reaction zone ($Z_1$) should be less than the amount sufficient to increase the production of MGN by no more than 10%, for example, no more than 5%, over the production of MGN in the absence of the Lewis acid promoter. The ratio of atomic equivalents of Ni to moles of Lewis acid in the first reaction zone may be less than 10:1 during normal process operation, for example at least 50% of the time, for example, at least 95% of the production of 3-pentenenitrile.

The Lewis acid promoter in the third reaction zone ($Z_3$) has a higher boiling point than adiponitrile. The reaction product, third catalyst and Lewis acid promoter flowing through the third reaction zone ($Z_3$) in step (c) may be contacted with an extraction solvent in an extraction zone to produce a solvent phase comprising the third catalyst and a raffinate phase comprising adiponitrile product from step (c). The raffinate phase also comprises compounds which are not adiponitrile, such as (1) compounds with a higher boiling point than adiponitrile and (2) compounds with a lower boiling point than adiponitrile. The raffinate phase may be distilled in one or more distillation steps to recover a purified adiponitrile product stream and to remove compounds which are not adiponitrile from the raffinate phase. For example, most of the Lewis acid promoter tends to partition into the raffinate phase, although at least a small amount of the promoter may also partition into the solvent phase. The partitioning of compounds between the two phases is discussed in U.S. Pat. No. 3,773,809. All of the Lewis acid promoter in the raffinate phase may be removed in distillation steps used to recover the adiponitrile product. The recovered adiponitrile product may be used to provide dinitrile to the extraction zone for the first catalyst as may be needed to promote separation. The extraction zone used to regenerate the first catalyst is different from the extraction zone used to regenerate the third catalyst. The compositions of the extraction solvents in these extraction zones may be the same or different. The raffinate phases from these zones may be distilled in the same or different distillation apparatus.

Zero valent nickel may be added to the purified first catalyst from the liquid/liquid extraction step after the catalyst is purified in the first liquid/liquid extraction step and before the purified first catalyst is recycled. For the purposes of the present disclosure, it will be understood that a catalyst which flows through a reaction zone is recycled when it is passed into the same or different reaction zone. Purified catalyst may be treated to increase its nickel content as taught in U.S. Pat. No. 4,416,825 to Ostermaier. Make-up ligand may also be added as needed, for example, following the catalyst purification steps.

In one embodiment, all of the zero valent nickel, which is added to make up for zero-valent nickel lost by catalyst degradation or unwanted removal during processing steps, may be added to the purified first catalyst after the catalyst has passed through the first liquid/liquid extraction zone.

At least a portion of the concentrated first catalyst may be recycled directly to the first reaction zone without being purified in a liquid/liquid extraction step. In such an embodiment, a purge stream may be taken from a catalyst stream which is recycled. The purge stream may be directed to the first liquid/liquid extraction step, where catalyst is purified or regenerated.

When the ligands of the first and second catalysts are the same, and when the first and second catalysts both flow through the first and second reaction zone, the first and second catalyst may be recycled to the first reaction zone or the second reaction zone or both the first and second reaction zone, but not to the third reaction zone. The third catalyst may be recycled to the third reaction zone, but not to the first reaction zone. In some embodiments, the third catalyst may be recycled to the second reaction zone, but not to the first reaction zone.

Examples of Lewis acid promoters used in the third reaction zone include zinc chloride and triphenylboron.

The first phosphorus-containing ligand of the first catalyst which flows through the first reaction zone ($Z_1$) may be, for example, a monodentate phosphorus-containing ligand. The second phosphorus-containing ligand of the second catalyst which flows through the second reaction zone ($Z_2$) may be, for example, a monodentate or bidentate phosphorus-containing ligand. The third phosphorus-containing ligand of the third catalyst which flows through the third reaction zone ($Z_3$) for reacting 3PN with HCN may be, for example, a bidentate phosphorus-containing ligand. The first phosphorus-containing ligand and the second phosphorus-containing ligand may be the same or different. The second phosphorus-containing ligand and the third phosphorus-containing ligand may be the same or different. Examples of the first phosphorus-containing ligands are mondentate ligands of the formula

$$P(OR^2)(OR^3)(OR^4) \qquad (I)$$

where $R^2$, $R^3$ and $R^4$ are the same or different and are aryl groups, for example, phenyl and tolyl groups, where the aryl or phenyl groups are each optionally substituted with up to four alkyl groups, each alkyl group having from 1-4 carbon atoms. Particular examples of the first phosphorus-containing ligand are tris(tolyl)phosphite (TTP) and a modified form of TTP, referred to herein as "MTTP." In MTTP, at least one of the tolyl groups in TTP is replaced with a phenyl group. TTP may be prepared by reacting $PCl_3$ with one or more cresol isomers, which are sources of tolyl groups in the end product. MTTP may be prepared by reacting $PCl_3$ with a mixture of phenol, which a source of phenyl groups in the end product, and one or more cresol isomers. Both TTP and MTTP typically comprise a mixture of compounds.

Adiponitrile can be used in the manufacture of precursors useful in the synthesis of nylon-6,6. For example, adiponitrile can be converted to hexamethylene diamine which can be used in the manufacture of nylon-6,6. In accordance with the invention, there is provided a process for the manufacture of hexamethylene diamine comprising a process of making adiponitrile as described herein, followed by hydrogenation of the adiponitrile thus obtained to give hexamethylene diamine. There is also provided a process for the manufacture of nylon-6,6 comprising a process of making adiponitrile as described herein, followed by hydrogenation of the adiponitrile thus obtained to give hexamethylene diamine, followed by reaction of the hexamethylene diamine with adipic acid, to give nylon-6,6.

DETAILED DESCRIPTION OF THE INVENTION

Figure 1:
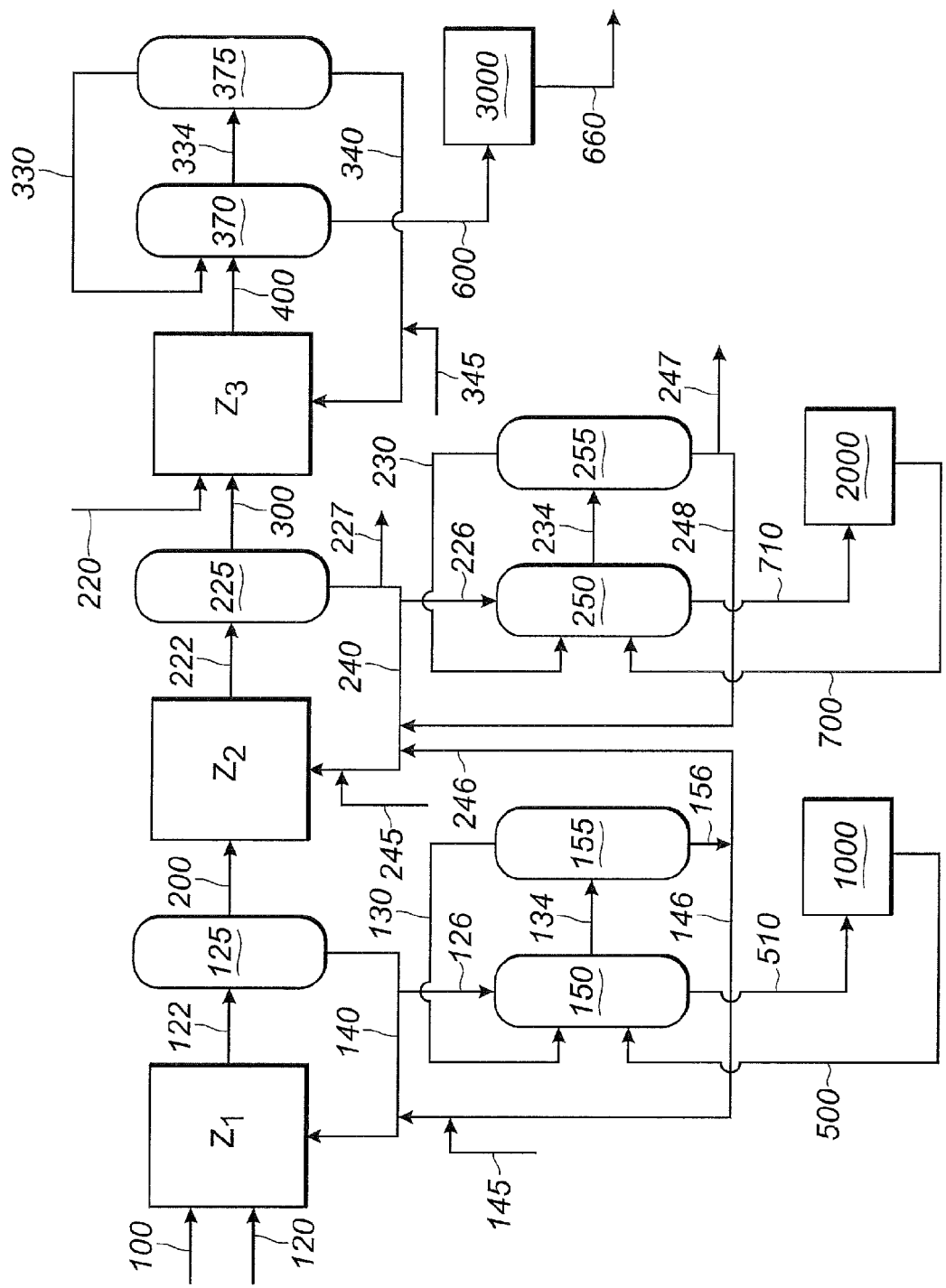
FIG. 1 is a representation of an integrated process for manufacturing 3-pentenenitrile comprising the steps of hydrocyanating 1,3-butadiene, isomerizing 2-methyl-3-penetenenitrile and hydrocyanating 3-pentenenitrile.

Although the following detailed description contains many specifics for the purpose of illustration, a person of ordinary skill in the art will appreciate that many variations and alterations to the following details are within the scope of the herein disclosed embodiments.

Accordingly, the following embodiments are set forth without any loss of generality to, and without imposing limitations upon any claimed invention. Before the present disclosure is described in greater detail, it is to be understood that this disclosure is not limited to particular embodiments described, as such may vary. It is also to be understood that the terminology used herein is for the purpose of describing particular embodiments only, and is not intended to be limiting, since the scope of the present disclosure will be limited only by the appended claims.

Certain abbreviations and definitions used herein include the following:

ADN=adiponitrile; BD=1,3-butadiene; c2PN=cis-2-pentenenitrile; c3PN=cis-3-pentenenitrile; $C_8H_{13}C{\equiv}N$=diolefinic acyclic and monoolefinic cyclic mononitrile compounds of the chemical formula $C_8H_{13}C{\equiv}N$; $C_8H_{14}(C{\equiv}N)_2$=monoolefinic acyclic and aliphatic cyclic dinitrile compounds of the chemical formula $C_8H_{14}(C{\equiv}N)_2$; dinitrile or dinitriles=ADN, MGN, and ESN unless specifically limited; ESN=ethylsuccinonitrile; $HC{\equiv}N$ or HCN=hydrogen cyanide (i.e. hydrocyanic acid); 2M2BN=2-methyl-2-butenenitrile including both (E)-2M2BN and (Z)-2M2BN isomers unless specifically limited; 2M3BN=2-methyl-3-butenenitrile; (E)-2M2BN=(E)-2-methyl-2-butenenitrile; (Z)-2M2BN=(Z)-2-methyl-2-butenenitrile; MGN=2-methylglutaronitrile; organic mononitrile=an organic compound comprising a single nitrile group, for example, a pentenenitrile; organic dinitrile=an organic compound comprising two nitrile groups, for example, ADN; pentenenitrile or pentenenitriles=4PN, 3PN, 2PN, 2M3BN, and 2M2BN isomers unless specifically limited; 2PN=2-pentenenitrile including both c2PN and t2PN isomers unless specifically limited; 3PN=3-pentenenitrile including both c3PN and t3PN unless specifically limited; 4PN=4-pentenenitrile; ppm=parts per million by weight unless stated otherwise; t2PN=trans-2-pentenenitrile, t3PN=trans-3-pentenenitrile; VN=valeronitrile.

As used herein a boiling point (BP) of a compound refers to the temperature at which a pure form of the compound boils at atmospheric pressure. A listed boiling point is the temperature of a boiling point for a compound listed in at least one reliable source from the chemical literature.

As used herein, the terms "distillation apparatus" and "distillation column" are used interchangeably, and both of these terms generally refer to equipment for performing distillation steps. For the purposes of this disclosure, a flasher is considered to be a distillation column.

Processes for making nitriles, such as 3PN and ADN, are described herein. In one embodiment, 3PN is recovered as an end product. In another embodiment, 3PN is used as a feed in an integrated process to make ADN.

A process for making 3PN, for example, in a first stage of an integrated processes for manufacturing adiponitrile (ADN), may involve reacting 1,3-butadiene (BD) and hydrogen cyanide (HC≡N) in a first reaction zone ($Z_1$) in the presence of a first catalyst. The reaction may take place under sufficient reaction conditions to produce a reaction product comprising 3-pentenenitrile (3PN) and 2-methyl-3-butenenitrile (2M3BN). The 2M3BN may be isomerized in a second reaction zone ($Z_2$) in the presence of a second catalyst under sufficient isomerization conditions to produce a reaction product comprising 3PN. The 3PN may be recovered from the effluents of both the first reaction zone ($Z_1$) and the second reaction zone ($Z_2$). In the second stage of an integrated process, the recovered 3PN may be reacted with HC≡N in a third reaction zone ($Z_3$) in the presence of a third catalyst. The second stage reaction may take place under sufficient reaction conditions to produce a reaction product comprising ADN. The ADN may be recovered. An integrated process does not require co-locality of the first and second stages.

The same catalyst may be used in all three reaction zones. Using the same catalyst in all three reaction zones may lower capital and operating costs. However, the transfer or sharing of a single catalyst among all three reaction zones ($Z_1$, $Z_2$ and $Z_3$) has disadvantages in that such a process may be performance limited by a single catalyst in any one or all 3 reaction zones. The physical properties of the single catalyst during required separation steps may also create disadvantages. For example, reboiler temperatures at certain points in the product separation train may degrade less thermally stable catalysts. By means of selecting catalysts for the individual reaction zones and limiting the transfer of catalyst between reaction zones and/or stages, higher 3PN and ADN product quality and chemical yields from BD and HC≡N may be achieved.

Selecting catalysts for individual reaction steps and limiting the transfer of catalyst between reaction steps facilitates control of reaction byproduct formation. Such byproducts include at least: 4-vinyl-1-cyclohexene, 2-methyl-2-butenenitrile, and mononitrile compounds of the chemical formula $C_8H_{13}C≡N$. As disclosed herein, separately treating the catalyst components and not co-mingling them among process stages provides opportunities to manage the flow of reaction byproducts, once formed, from one process step into another process step. For example, transfer of reaction byproducts in catalyst streams from the first process stage (e.g., in $Z_1$ and $Z_2$) to produce 3PN into the second process stage to produce ADN (performed in $Z_3$) and vice versa, may be controlled.

Overview of FIG. 1

A more detailed description of a representative process for the manufacture of adiponitrile is made with reference to FIG. 1, which provides a simplified schematic representation of such a process. FIG. 1 shows a first reaction zone ($Z_1$), where a mixture comprising 1,3-butadiene and hydrogen cyanide is contacted in the presence of a first catalyst, for example, comprising zero-valent Ni and a first phosphorus-containing ligand, collectively a first catalyst system, to produce a reaction product substantially comprising 3-pentenenitrile (3PN) and 2-methyl-3-butenenitrile (2M3BN).

Figure 4:
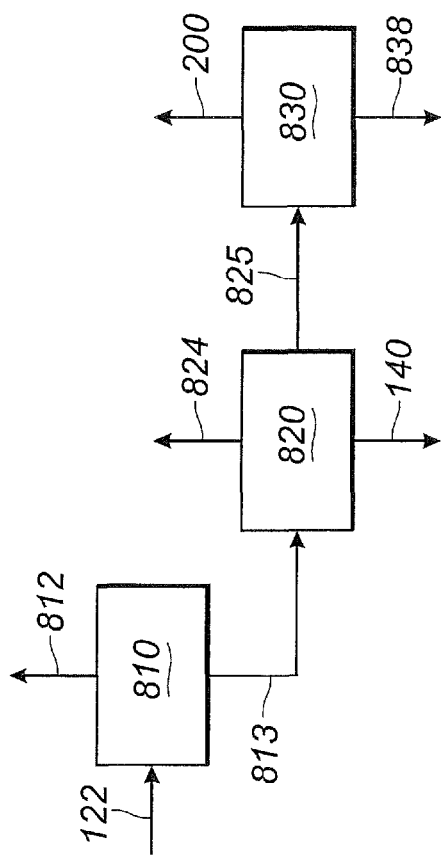
FIG. 4 is a representation of an example of separation section 125 shown in FIG. 1.

As shown in FIG. 1, 1,3-butadiene reactant is fed into the first reaction zone ($Z_1$) through line 100, hydrogen cyanide reactant is fed into the first reaction zone ($Z_1$) through line 120, and catalyst is fed into the first reaction zone ($Z_1$) through line 140. A reaction product stream is taken from the first reaction zone ($Z_1$) through line 122. The reaction product stream in line 122 comprises products, byproducts, unreacted reactants and catalyst, which flows through the first reaction zone ($Z_1$). The reaction product stream 122 is introduced into a separation section 125, to obtain, inter alia, a concentrated catalyst stream 140 and product stream 200 comprising 2-methyl-3-butenenitrile (2M3BN). The separation section 125 may comprise one or more distillation columns. An example of separation section 125 is shown in FIG. 4. Unreacted hydrogen cyanide and 1,3-butadiene may also be separated from reaction products and catalyst in separation section 125. Unreacted 1,3-butadiene may be recycled to the first reaction zone ($Z_1$) through lines not shown in FIG. 1. A stream comprising 3-pentenenitrile (3PN) may also be withdrawn from separation section 125 through a line not shown in FIG. 1. At least a portion of the catalyst separated from reaction products in separation section 125 may be recycled to the first reaction zone ($Z_1$) through line 140.

Subsequent to the reaction in the first reaction zone ($Z_1$), the substantial isomerization of 2M3BN in a second reaction zone ($Z_2$) is conducted in the presence of an isomerization catalyst to produce a reaction product comprising substantially 3PN. The isomerization catalyst is also referred to herein as the second catalyst. The isomerization catalyst may be the same as the catalyst introduced into the first reaction zone ($Z_1$). Optionally, the isomerization catalyst may be different from the catalyst introduced into the first reaction zone ($Z_1$).

Figure 5:
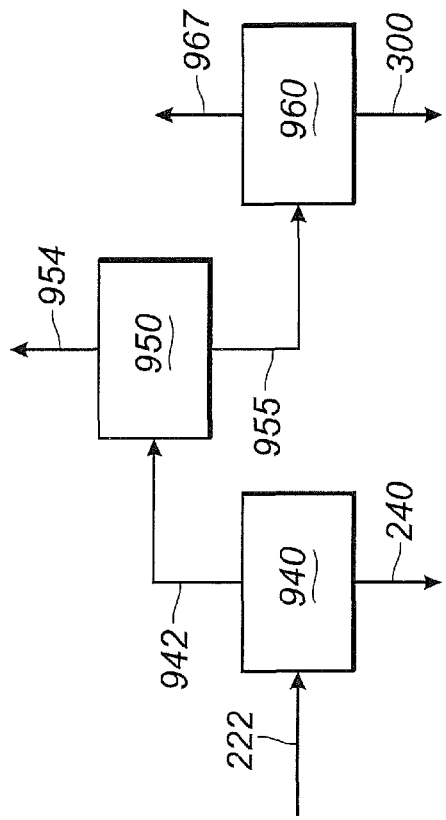
FIG. 5 is a representation of an example of separation section 225 shown in FIG. 1.

As shown in FIG. 1, a feed comprising 2M3BN is introduced into the second reaction zone ($Z_2$) through line 200. Catalyst is introduced into the second reaction zone ($Z_2$) through line 240. The effluent stream 222 from the second reaction zone ($Z_2$) comprises catalyst and 3PN product. This effluent stream 222 passes into separation section 225 to obtain, inter alia, a 3PN product stream 300 and a concentrated catalyst stream 240. Separation section 225 may comprise one or more distillation apparatus. FIG. 5 shows an example of such a separation section 225.

Catalyst recycle systems are shown in FIG. 1 for supplying catalyst to the first reaction zone ($Z_1$) and the second reaction zone ($Z_2$). These catalyst recycle systems comprise further systems for purifying at least a portion of the catalyst prior to recycle.

In the catalyst recycle system for supplying catalyst to the first reaction zone ($Z_1$), a portion of the concentrated catalyst stream in line 140 is diverted into catalyst purge stream 126.

Catalyst in purge stream 126 is in the form of a solution including impurities, such as reaction byproducts and catalyst degradation byproducts. Catalyst in purge stream 126 is fed to liquid/liquid extraction zone 150 to at least partially purify or regenerate the catalyst. The catalyst is purified or regenerated in that at least some byproducts are removed from the catalyst solution.

A non-polar solvent, such as an alkane, is fed into the liquid/liquid extraction zone 150 through line 130. A polar solvent, which is immiscible with the non-polar solvent, is also fed into the liquid/liquid extraction zone 150 through line 500.

In one embodiment, catalyst purge stream 126 and the polar solvent in line 500 are mixed prior to charging the combined stream to extraction zone 150. Although FIG. 1 schematically shows purge stream 126 and recycle stream 500 separately added to extraction zone 150, it is to be understood that catalyst purge stream 126 and the polar solvent in line 500 are preferably mixed before charging a combined stream to extraction zone 150.

In extraction zone 150, there is formed a non-polar phase comprising non-polar solvent and catalyst and a polar phase (e.g., a raffinate) comprising polar solvent and, for example, reaction byproducts and catalyst degradation products. The non-polar phase is taken from extraction zone 150 via line 134 to distillation apparatus 155. The polar phase is taken from extraction zone 150 via line 510 to separation section 1000.

Figure 2:
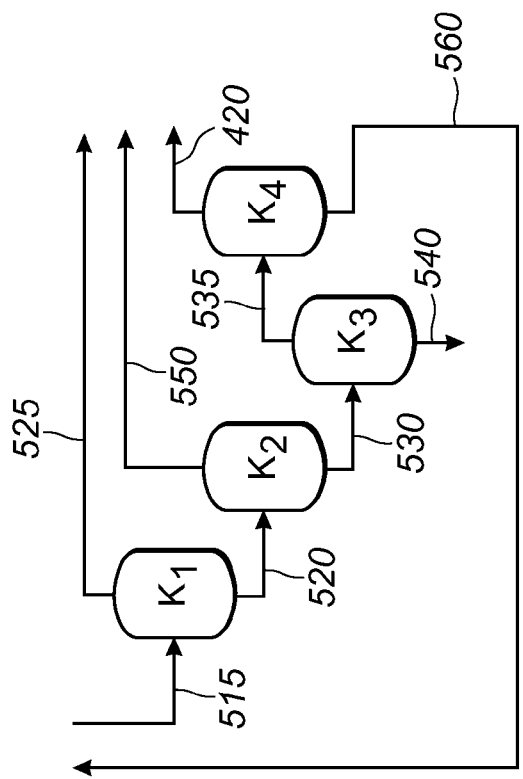
FIG. 2 is a representation of an example of separation section 1000 or separation section 2000 shown in FIG. 1.

An example of separation section 1000 is described in greater detail in FIG. 2. Separation section 1000 may include, collectively, a series of columns ($K_1$, $K_2$, $K_3$ and $K_4$) which provide for the removal of certain reaction byproducts and certain catalyst degradation products from the polar solvent. The column bottom of $K_4$ provides polar solvent, which is returned to extraction zone 150, via line 500.

Non-polar solvent is distillatively recovered in distillation apparatus 155 and returned to extraction zone 150, via line 130. Extraction zone 150, line 134, distillation apparatus 155 and line 130, collectively, form a recovery loop for recycling non-polar solvent into extraction zone 150. Extraction zone 150, line 510, separation section 1000 and line 500, collectively, form a recovery loop for recycling polar solvent into extraction zone 150. Additional non-polar solvent and polar solvent may be introduced into extraction zone 150 by lines not shown in FIG. 1. This additional solvent may be added for start up and for make-up of solvent lost during the course of the liquid/liquid extraction step.

Column bottoms from distillation column 155 include partially purified catalyst. This catalyst is partially purified or regenerated in the sense that at least some of the catalyst degradation products and/or reaction byproducts have been separated from the solution containing the catalyst. This partially purified catalyst may be taken from distillation column 155 through line 156 and introduced at any point for recycle into the first reaction zone ($Z_1$). In FIG. 1, partially purified catalyst may be taken from distillation column 155 through line 156 and transferred into line 146 for introduction into catalyst recycle line 140 for recycle into the first reaction zone ($Z_1$). FIG. 1 shows the introduction of stream 146 downstream of the take-off stream 126, but this stream may, optionally, be introduced upstream of the take-off stream 126. Stream 146 may also, optionally, be added to any catalyst-containing stream associated with the first reaction zone ($Z_1$). Optionally, at least a portion of the partially purified catalyst stream in line 156 may be recycled into the second reaction zone ($Z_2$). In FIG. 1, partially purified catalyst stream in line 156 may be transferred into line 246 for introduction into catalyst recycle line 240 for recycle into the second reaction zone ($Z_2$). However, it will be understood that other routes, not shown in FIG. 1, may be used for routing partially purified first catalyst into the second reaction zone ($Z_2$).

The partially purified stream of first catalyst, which is subsequently returned to the first reaction zone ($Z_1$) or, optionally, to the second reaction zone ($Z_2$), may be provided with additional zero-valent Ni and/or additional phosphorus-containing ligand. In FIG. 1, additional zero-valent Ni and/or additional phosphorus-containing ligand may be provided via line 145. Also as shown in FIG. 1, partially purified stream of first catalyst, which is subsequently fed to the second reaction zone ($Z_2$), may be provided with additional zero-valent Ni and/or phosphorus-containing ligand via line 245. However, it will be understood, that make-up catalyst may be added via different routes, not shown in FIG. 1. For example, make-up catalyst stream 145 may be charged to other sections of the first reaction zone catalyst loop or, for example, directly to the first reaction zone ($Z_1$).

In a particular embodiment shown in FIG. 1, the second reaction zone ($Z_2$) is provided with a second catalyst recovery system for supplying catalyst to the second reaction zone ($Z_2$). In this second catalyst recycle system, a portion of the concentrated catalyst stream in line 240 is diverted into catalyst purge stream 226. This catalyst purge stream 226 is fed into liquid/liquid extraction zone 250. A non-polar solvent, such as an alkane, is fed into the liquid/liquid extraction zone 250 through line 230. A polar solvent, which is immiscible with the non-polar solvent, is also fed into the liquid/liquid extraction zone 250 through line 700. Dinitriles from sources not shown in FIG. 1 may be added to extraction zone 250, as needed to accomplish desired phase separation and extraction.

In one embodiment, catalyst purge stream 226 and the polar solvent in line 700 are mixed prior to charging the combined stream to extraction zone 250. Although FIG. 1 schematically shows purge stream 226 and recycle stream 700 separately added to extraction zone 250, it is to be understood that catalyst purge stream 226 and the polar solvent in line 700 are preferably mixed before charging a combined stream to extraction zone 250.

In one embodiment, a portion of the refined dinitrile product stream from the third reaction zone ($Z_3$) may be used as a feed to extraction zone 250. For example, a side stream (not shown) may be taken from line 500 and introduced into extraction zone 250. In extraction zone 250, there is formed a non-polar phase comprising non-polar solvent and catalyst and a polar phase (e.g., a raffinate) comprising, for example, polar solvent, reaction byproducts and certain catalyst degradation products. The non-polar phase is taken from extraction zone 250 via line 234 to distillation apparatus 255. The polar phase is taken from extraction zone 250 via line 710 to separation section 2000. Separation section 2000 is described in greater detail in FIG. 2.

Separation section 2000 includes, collectively, a series of columns ($K_1$, $K_2$, $K_3$ and $K_4$) which provide for the separation of certain reaction by-products and catalyst degradation products. The column bottom of $K_4$ provides polar solvent, which is returned to extraction zone 250, via line 700. Additional polar solvent, in the form of adiponitrile, as need for phase separation, may be provided from adiponitrile produced in the third reaction zone ($Z_3$) through lines not shown in FIG. 1.

Non-polar solvent is distillatively recovered in distillation apparatus 255 and returned to extraction zone 250, via line 230. Extraction zone 250, line 234, distillation column 255 and line 230, collectively, form a recovery loop for recycling non-polar solvent into extraction zone 250. Extraction zone 250, line 710, separation section 2000 and line 700, collectively, form a recovery loop for recycling polar solvent into extraction zone 250.

Column bottoms from distillation column 255 include partially purified catalyst. This catalyst is partially purified or regenerated in the sense that at least some of the catalyst degradation products and/or reaction byproducts have been separated from the solution containing the catalyst. This partially purified catalyst may be taken from distillation apparatus 255 through line 248 for introduction into catalyst recycle line 240 for recycle into the second reaction zone ($Z_2$). Optionally, a side stream may be taken from line 248 into line 247, and this side stream may be used as a catalyst feed to the first reaction zone ($Z_1$), for example, by introducing the side stream from line 247 into line 146 or line 140. Any partially purified stream of catalyst, which is subsequently fed to the second reaction zone ($Z_2$), may be provided with additional zero-valent Ni and/or phosphorus-containing ligand, for example, via line 245. Although not shown in FIG. 1, line 245 may optionally be fed directly into line 246 or line 248 instead of line 240. Other ways of introducing make-up catalyst are known in the art and may be used.

Although not shown in FIG. 1, it is possible that the first reaction zone ($Z_1$) and the second reaction zone ($Z_2$) share a single catalyst recovery system. A shared catalyst recovery system may be desirable when the first and second phosphorus-containing ligands are the same. In such a shared system, the following features may be eliminated or shut down: lines 226, 230, 234, 247, 248, 700, and 710; extraction zone 250; distillation apparatus 255; and separation section 2000. Instead of taking a purge stream via line 226, a purge stream may be taken via line 227 and introduced into line 126 or directly into extraction zone 150. In such a shared catalyst recovery system, any partially purified catalyst stream entering the second reaction zone ($Z_2$) would pass through lines 246 and 240 according to the configuration shown in FIG. 1.

The 3PN product in line 300 is introduced into the third reaction zone ($Z_3$), where 3PN is reacted with HCN. 3PN from separation section 125 may also be introduced into the third reaction zone ($Z_3$) through a line or lines not shown in FIG. 1. The HCN reactant feed is introduced into the third reaction zone ($Z_3$) through line 220. A third catalyst comprising, for example, zero-valent Ni and a third phosphorus-containing ligand, collectively a third catalyst system, and a Lewis acid promoter is introduced into the third reaction zone ($Z_3$) through line 340. The reaction of 3PN and HCN in the third reaction zone ($Z_3$) produces a reaction product containing adiponitrile. A reaction product stream is taken from the third reaction zone ($Z_3$) by line 400. The reaction product stream comprises, for example, adiponitrile, catalyst, promoter, and unreacted reactants. The reaction product stream may optionally be passed through a separation section (not shown in FIG. 1) to remove unreacted reactants, prior to separation of catalyst from adiponitrile product.

Catalyst and adiponitrile product from the product stream in line 400 are passed into liquid/liquid extraction zone 370. A non-polar solvent, such as an alkane, is fed into the liquid/liquid extraction zone 370 through line 330. The non-polar solvent introduced into the liquid/liquid extraction zone 370 may have the same or different composition as the non-polar solvent introduced into the liquid/liquid extraction zone 150. Together, non-polar solvent from line 330 and adiponitrile product from line 400 comprise an extractant system of immiscible components. In extraction zone 370, there is formed a non-polar phase comprising non-polar solvent and catalyst and a polar phase (e.g., a raffinate) comprising adiponitrile, promoter and catalyst degradation products.

The non-polar phase is taken from extraction zone 370 via line 334 to distillation apparatus 375. The polar phase comprising adiponitrile is taken from extraction zone 370 via line 600 to adiponitrile purification section 3000. Adiponitrile purification section 3000 is described in greater detail in FIG. 3.

Adiponitrile purification section 3000 may include, collectively, a series of columns ($K'_1$, $K'_2$, $K'_3$ and $K'_4$) which provide for the separation of impurities, such as reaction byproducts and catalyst degradation products. The column bottom of $K'_4$ provides the purified adiponitrile product, which is recovered in line 660. A portion of the purified adiponitrile product may optionally be returned to extraction zone 150 or extraction zone 250 (by lines not shown in FIG. 1) to facilitate phase separation in these extraction zones.

Non-polar solvent is distillatively recovered in distillation apparatus 375 and returned to extraction zone 370, via line 330. Extraction zone 370, line 334, distillation apparatus 375 and line 330, collectively, form a recovery loop for recycling non-polar solvent into extraction zone 370. Column bottoms from distillation column 375 include partially purified catalyst. This partially purified catalyst may be taken from distillation column 375 through line 340 for recycle of catalyst into the third reaction zone ($Z_3$). The partially purified stream of third catalyst in line 340, which is subsequently returned to the third reaction zone ($Z_3$), may be provided with make-up quantities of additional zero-valent Ni and/or third phosphorus-containing ligand along with promoter. In FIG. 1, make-up quantities of additional zero-valent Ni and/or third phosphorus-containing ligand and/or promoter may be added via line 345. However, it will be appreciated that there are other ways of introducing make-up catalyst and promoter. For example, all or a portion of the recycled catalyst stream 340 may be charged to a catalyst reactor to increase its nickel content and the effluent from the catalyst reactor may introduced at a suitable point.

Overview of FIG. 2

FIG. 2 shows a distillation train, which may be used as separation section 1000 or separation section 2000, shown in FIG. 1. In FIG. 2, line 515 represents either line 510 or line 710 of FIG. 1. Line 515 transports a raffinate stream from either extraction zone 150 or extraction zone 250 into separation section 1000 or separation section 2000, as shown in FIG. 1. The raffinate stream in line 515 is first passed into distillation column $K_1$, where extraction solvent is separated from higher boiling components of the raffinate stream. In particular, extraction solvent, such as cyclohexane, is withdrawn from distillation column $K_1$ through line 525, and higher boiling components of the raffinate stream are withdrawn from distillation column $K_1$ through line 520.

The solvent-depleted stream in line 520 is then passed into distillation column $K_2$, where pentenenitrile is separated from higher boiling components remaining in the raffinate stream. In particular, pentenenitrile, such as 3PN and any 2M3BN, present is withdrawn from distillation column $K_2$ through line 550, and higher boiling components of the raffinate stream are withdrawn from distillation column $K_2$ through line 530.

The pentenenitrile-depleted stream in line 530 is then passed into distillation column $K_3$, where dinitriles are separated from higher boiling components remaining in the raffinate stream. In particular, dinitriles, such as ADN and MGN, are withdrawn from distillation column $K_3$ through line 535, and higher boiling components of the raffinate stream are withdrawn from distillation column $K_3$ through line 540. These higher boiling components in line 540 may comprise, for example, catalyst degradation products.

The dinitrile-enriched stream in line 535 is then passed into distillation column $K_4$, where adiponitrile is separated from lower boiling dinitriles, such as MGN. In particular, MGN is withdrawn from distillation column $K_4$ through line 420. The MGN-containing stream in line 420 may also include $C_8H_{13}C\equiv N$ compounds and phenolic compounds. An adiponitrile-enriched stream is withdrawn from distillation column $K_4$ through line 560. In FIG. 2, line 560 represents either line 500 or line 700 of FIG. 1. As shown in FIG. 1, the adiponitrile-enriched stream in line 500 is recycled to the liquid/liquid extraction zone 150, and the adiponitrile-enriched stream in line 700 is recycled to the liquid/liquid extraction zone 250.

Figure 3:
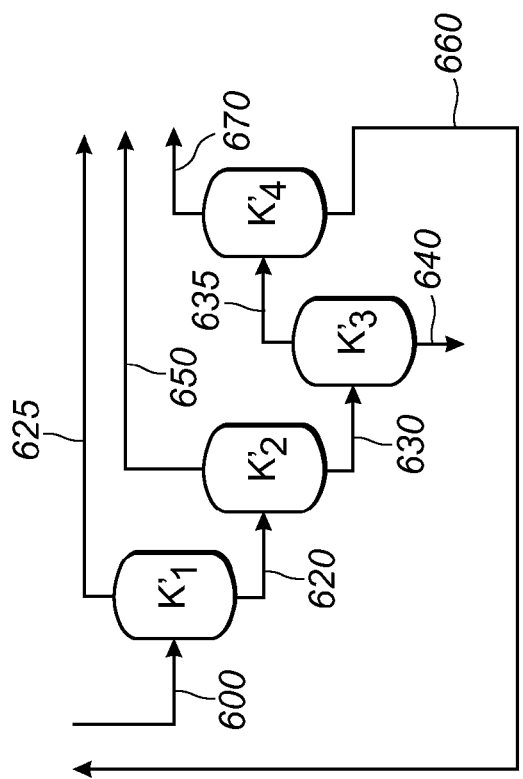
FIG. 3 is a representation of an example of adiponitrile purification section 3000 shown in FIG. 1.

Overview of FIG. 3

FIG. 3 shows a distillation train, which may be used as adiponitrile purification section 3000, shown in FIG. 1. Line 600 transports a raffinate stream from extraction zone 370 into distillation column $K'_1$, where extraction solvent is separated from higher boiling components of the raffinate stream. In particular, extraction solvent, such as cyclohexane, is withdrawn from distillation column $K'_1$ through line 625, and higher boiling components of the raffinate stream are withdrawn from distillation column $K'_1$ through line 620.

The solvent-depleted stream in line 620 is then passed into distillation column $K'_2$, where pentenenitrile is separated from higher boiling components remaining in the raffinate stream. In particular, pentenenitrile, such as 3PN and any 2M3BN present, is withdrawn from distillation column K'$_2$ through line 650, and higher boiling components of the raffinate stream are withdrawn from distillation column K'$_2$ through line 630.

The pentenenitrile-depleted stream in line 630 is then passed into distillation column K'$_3$, where dinitriles are separated from higher boiling components remaining in the raffinate stream. In particular, dinitriles, such as ADN and MGN, are withdrawn from distillation column K'$_3$ through line 635, and higher boiling components of the raffinate stream are withdrawn from distillation column K'$_3$ through line 640. These higher boiling components in line 640 may comprise, for example, catalyst degradation products.

The dinitrile-enriched stream in line 635 is then passed into distillation column K'$_4$, where adiponitrile is separated from lower boiling dinitriles, such as MGN. In particular, MGN is withdrawn from distillation column K'$_4$ through line 670, and a purified adiponitrile stream is withdrawn from distillation column K'$_4$ through line 660.

Overview of FIG. 4

FIG. 4 is a schematic representation of an example of a distillation train, which may be used as separation section 125, shown in FIG. 1. Stream 122 comprising 3PN, 2M3BN, at least one catalyst, and BD is transferred into an apparatus 810 for distillation. In this apparatus, stream 122 is distilled to obtain a BD-enriched stream 812 and a BD-depleted stream 813 comprising 3PN, 2M3BN, and at least one catalyst. The BD-enriched stream 812 may be recycled to the first reaction zone ($Z_1$).

The BD-depleted stream 813, which comprises 3PN, 2M3BN, and at least one catalyst is then transferred to another apparatus 820 for further distillation. In this apparatus, stream 813 is distilled to obtain a top product stream 824 enriched in BD, a stream 825, comprising 3PN and 2M3BN, and a bottom product stream 140 enriched in at least one catalyst. Stream 824 enriched in BD may also be recycled to the first reaction zone ($Z_1$). If excess dinitriles are introduced into apparatus 820, the catalyst may thermally degrade, causing nickel and ligand to disassociate and resulting in plating out of nickel on high-temperature surfaces such as exchanger tubes and reboiler wall surfaces or, alternatively, trigger precipitation of nickel solids, for example, in the column bottoms.

Stream 825, comprising 3PN and 2M3BN, is transferred at least in part to another distillation apparatus 830. In this apparatus, the distillation of stream 825 is distilled to obtain 2M3BN-enriched stream 200 and 2M3BN-depleted stream 838 comprising 3PN. As described in the "Nylon Intermediates Refining" section of the PhD thesis dissertation by Decio Heringer Coutinho, University of Texas at Dallas, December 2001, stream 200 may be obtained at the top region of the distillation apparatus, while the stream 838 may be obtained at the bottom region of the distillation apparatus.

FIG. 4 illustrates one distillation system for distilling the effluent from the first reaction zone ($Z_1$). However, it will be understood that it is within the skill in the art to design and operate other distillation systems to achieve the same or essentially the same results. For example, depending upon the thermal stability of catalyst, it may be possible to combine distillation apparatus 810 and distillation apparatus 820 into a single distillation apparatus, where a BN-enriched stream is withdraw as a top draw, a PN-enriched stream is withdrawn as a side draw, and a catalyst-enriched stream is withdrawn as a bottom draw.

Overview of FIG. 5

FIG. 5 is a schematic representation of an example of a distillation train, which may be used as separation section 225, shown in FIG. 1. The isomerization reaction effluent in stream 222 obtained in the second reaction zone is distilled to recover catalyst and products. In a distillation step not shown in FIG. 5, light boilers may first be removed from stream 222. Low boilers are compounds which boil at temperatures less than pentenenitriles. Examples of light boilers include, butane, butadiene and cyclohexane. Compounds in stream 222, which boil at the same temperature or higher than pentenenitrile, are introduced into distillation apparatus 940. A pentenenitrile-enriched stream 942, comprising 3PN, 2M3BN, and (Z)-2M2BN, may be obtained from the distillation apparatus 940. Stream 942 may also comprise other pentenenitriles, selected from 4PN, (E)-2M2BN, or a combination thereof, and optionally dimerized BD compounds having the empirical formula $C_8H_{12}$, such as VCH and ethylidene cyclohexene isomers. A pentenenitrile-depleted stream 240, enriched in at least one catalyst, may be obtained as the bottom product.

U.S. Pat. No. 3,852,329 describes a process for "reduced loss to undesirable products such as 2-methyl-2-butenenitrile." An objective of the distillation of stream 942 is to purge at least a portion of the lower-boiling (Z)-2M2BN isomer from the 3PN and 2M3BN reaction product mixture.

Stream 942, comprising 3PN, 2M3BN, and (Z)-2M2BN, is distilled in distillation apparatus 950. Stream 954 is obtained as an overhead product that is enriched in (Z)-2M2BN. Stream 955, comprising 3PN and 2M3BN, is obtained as a bottom product and is depleted in (Z)-2M2BN. "Enriched" and "depleted" in (Z)-2M2BN are relative to its concentration in stream 942.

Stream 954 may also comprise other pentenenitriles, selected from the group comprising 2M3BN, (E)-2M2BN, and optionally dimerized BD compounds having the empirical formula $C_8H_{12}$, such as VCH and ethylidene cyclohexene isomers. Stream 955 may also comprise other pentenenitriles, selected from the group comprising 4PN, 2PN, and (E)-2M2BN.

In one embodiment, the distillation is operated in such a manner to cause dimerized BD compounds to be enriched in stream 954 and depleted in stream 955, both relative to the concentration of dimerized BD compounds in stream 942. In another embodiment, dimerized BD compounds are enriched in stream 954 through an azeotrope of said compounds with 2M3BN. In another embodiment, stream 954 comprises greater than 1% by weight, for example greater than 5% by weight, for example greater than 10% by weight of 2M3BN, relative to the total mass of stream 954.

Stream 955, comprising 3PN and 2M3BN, may be transferred at least in part to distillation apparatus 960. In this apparatus, the distillation of stream 955 occurs to obtain 2M3BN-enriched stream 967 and a 2M3BN-depleted stream 300 comprising 3PN. As described in the "Nylon Intermediates Refining" section of the PhD thesis dissertation by Decio Heringer Coutinho, University of Texas at Dallas, December 2001, stream 967 may be obtained at the top region of the distillation apparatus, while the stream 300 may be obtained at the bottom region of the distillation apparatus.

FIG. 5 illustrates one distillation system for distilling the effluent from the second reaction zone ($Z_2$). However, it will be understood that it is within the skill in the art to design and operate other distillation systems to achieve the same or essentially the same results. For example, a distillation step to remove low boilers may be inserted into the system, as described above. It is also possible to share equipment used for distilling the effluent from the first reaction zone. For example, a stream comprising 3PN and 2M3BN obtained by distilling the effluent from the second reaction zone ($Z_2$) may be passed to a distillation apparatus, such as distillation apparatus 830, used in the distillation of the effluent form the from the first reaction zone ($Z_1$), to obtain a 3PN-enriched stream and a 2M3BN-enriched stream.

Figure 6:
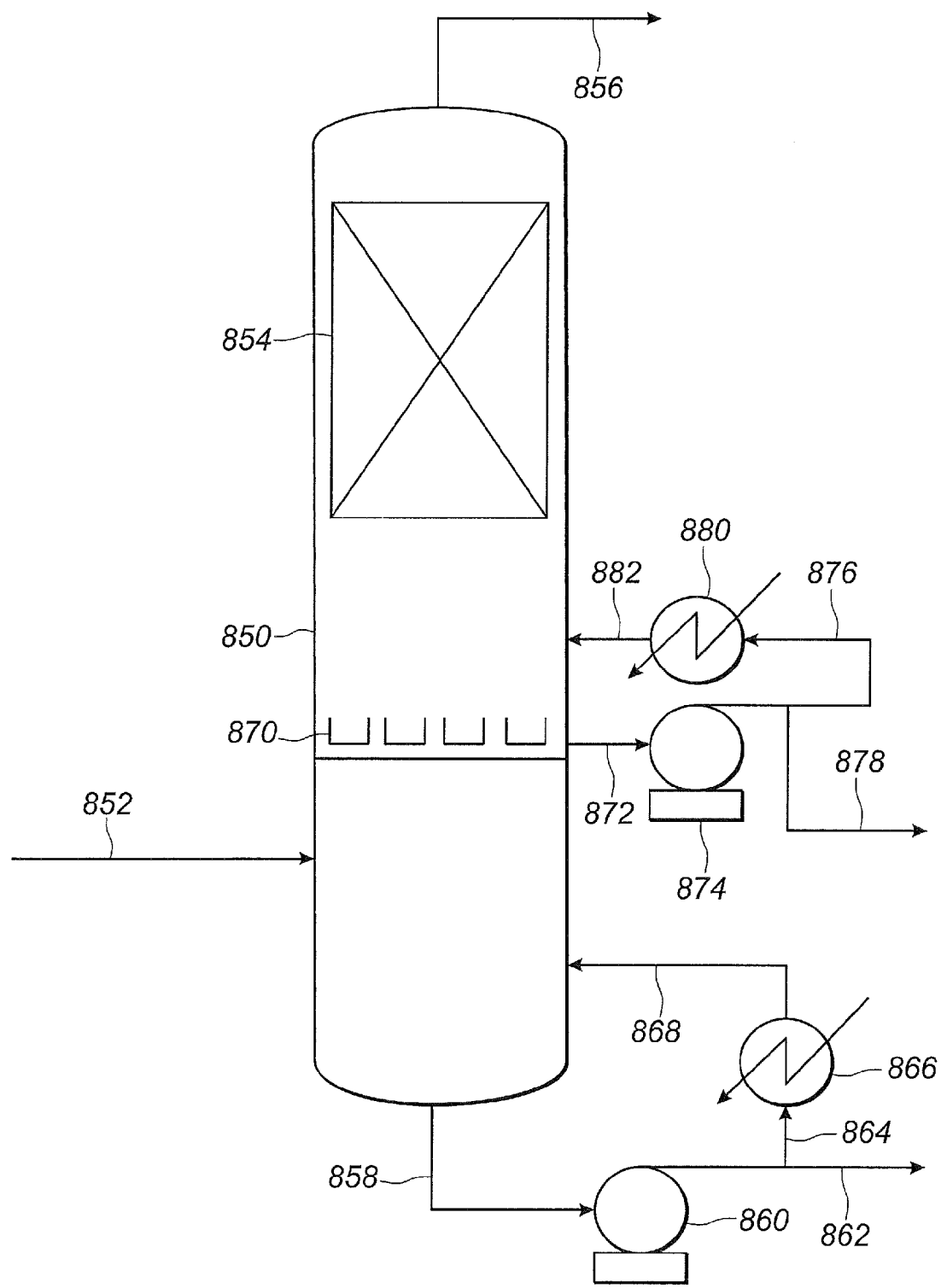
FIG. 6 is a representation of a distillation apparatus which may be used to separate pentenenitriles, catalyst and reaction byproducts from the effluent of a first reaction zone ($Z_1$), where 1,3-butadiene is reacted with hydrogen cyanide.

Overview of FIG. 6

FIG. 6 illustrates features of a distillation column having an upper draw outlet, a bottom draw outlet and a side draw outlet. A stream enriched in pentenenitrile is withdrawn from the top draw outlet. A stream enriched in catalyst is withdrawn from the bottom draw outlet. This distillation column may be designed and operated to optimize collection of liquids having boiling between 147 and 295° C., which are withdrawn from the side draw outlet.

In FIG. 6, a feed is introduced into distillation column 850 through stream 852. The feed in stream 852 comprises (1) pentenenitriles, including 3-pentenenitrile and 2-methyl-3-butenenitrile, (2) adiponitrile, (3) compounds having a boiling point between that of 3-pentenenitrile and adiponitirile and (4) compounds having a boiling point higher than adiponitrile.

3-Pentenenitrile has a boiling point of 147° C. Other pentenenitriles have a boiling point of less than 147° C. Adiponitrile has a boiling point of 295° C. Compounds which have a boiling point between 147 and 295° C. are also referred to herein as "intermediate boilers." Intermediate boilers which may be present in feed stream 852 comprise one or more compounds selected from the group consisting of phenol, cresols, $C_8H_{13}C\equiv N$ compounds, methylglutaronitrile (MGN) and tertiary-butylcatechol (TBC).

Compounds in feed stream 852 having a higher boiling point than adiponitrile include catalyst and catalyst degradation byproducts. The feed stream introduced into distillation column 850 through stream 852 may be obtained by distilling the reaction effluent from the first reaction zone ($Z_1$) under conditions sufficient to generate a butadiene-enriched stream and a butadiene-depleted stream. This butadiene-depleted stream may be fed into distillation column 850 through stream 852.

A rectifying section comprising at least one, for example, at least two, stages of separation is provided between the feed inlet and the upper draw outlet. In FIG. 6, the position of the feed inlet is shown as the position where stream 852 enters the distillation column 850. Also, the position of the upper draw outlet is shown as the position where stream 856 exits the distillation column 850. A packing section 854 is also provided in distillation column 850 above the position where feed stream 852 enters distillation column 850. Stream 856 is enriched in pentenenitriles relative to the concentration of pentenenitriles in feed stream 852.

Compounds are withdrawn from the bottom draw outlet of distillation column 850 through stream 858. Stream 858 is enriched in catalyst relative to the concentration of catalyst in feed stream 852. Stream 858 passes through pump 860 to stream 862. A portion of the catalyst-containing stream 862 may be recycled to the first reaction zone ($Z_1$) and a portion of stream 862 may be withdrawn as a purge stream, which is subsequently purified, for example, in a liquid/liquid extraction zone. A portion of stream 862 is withdrawn as a side stream 864, which is, in turn, heated in heat exchanger 866. The heated stream 868 is then returned to a lower section of distillation column 868. The loop comprising stream 858, pump 860, stream 862, side stream 864, heat exchanger 866, stream 868 and column bottoms constitutes a reboiler section for providing vapor which passes upwards through distillation column 850. This vapor comprises pentenenitrile vapor and adiponitrile vapor.

Above this reboiler section and above the point of entry of feed from stream 852, a liquid collection apparatus 870 is provided. This liquid collection apparatus 870 may be a chimney tray. This liquid collection apparatus 870 has at least one opening, which permits vapor ascending upwards through the column to pass through the apparatus. However, the liquid collection apparatus 870 does not permit liquids descending through the column to pass through. For example, the liquid collection apparatus 870 may have a tray section for collecting liquids. Accordingly, liquids descending from a point above the liquid collection apparatus 870 in the column are collected.

Liquids collected in liquid collection apparatus 870 are withdrawn from the distillation column through stream 872. This stream 872 passes through pump 874 to stream 876. A portion of the collected liquid in stream 874 is withdrawn as side stream 878. A portion of the liquid collected in stream 876 is heated in heat exchanger 880. The heated stream 882 is then returned to distillation column at a point above the liquid collection apparatus 870. The loop comprising stream 872, pump 874, stream 876, heat exchanger 880, stream 882 and liquid collection apparatus 870 constitutes a reboiler section for heating the collected liquids. This reboiler section is operated in a manner such that the percentage of pentenenitriles in the collected liquid which is vaporized is greater than the percentage of adiponitrile in the collected liquid which is vaporized. Heat supplied by heat exchanger 880 may be sufficient to restore heat lost during the collection and recycle of liquids through the reboiler loop, without supplying excess heat. Heat exchanger 880 may be considered to be a trim heater.

The pump around liquid return point from the reboiler for heating collected liquid from side draw stream 872 is shown in FIG. 6 as the point where stream 882 enters distillation column 850. The section of the distillation column above this pump around liquid return point may be considered to be the pentenenitrile flasher section of column 850. This pentenenitrile flasher section may contain one or more stages of separation in the form of trays or packing. These stages of separation are illustrated by packing 854 in FIG. 6. The overhead stream from the pentenenitrile flasher is enriched in pentenenitriles and normally requires no condensation and reflux to the flasher.

The distillation column 850 may be operated in a manner such that the catalyst-enriched stream withdrawn as stream 862 comprises at least 5% by weight of pentenenitrile including the sum of 3-pentenenitrile and 2-methyl-3-butenenitrile. The distillation column 850 may further be operated in a manner such that adiponitrile and intermediate boilers, including, for example, MGN, $C_8H_{13}C\equiv N$ compounds, phenol and cresols, are collected in the liquid collection apparatus 870. The collected liquid is withdrawn in stream 878. This stream 878 may be passed either directly or indirectly (e.g., into the catalyst purge stream) to an extraction zone. In this way, there is achieved an increased amount of intermediate boilers passed into an extraction zone and separated from recycled catalyst. In another option, compounds in stream 878 may be separated and recovered in a distillation process.

Low, Intermediate and High Boilers

When 1,3-butenenitrile is reacted with hydrogen cyanide, both 3-pentenenitrile and 2-methyl-3-butenenitrile are produced. 2-methyl-3-butenenitrile has a listed boiling point of 125° C., cis-2-pentenenitrile has a listed boiling point of 127-128° C., and trans-3-pentenenitrile has a listed boiling point of 144-147° C. In an integrated process for making adiponitrile, 3-pententnitrile is reacted with hydrogen cyanide to produce adiponitrile. Adiponitrile has a listed boiling point of 295° C.

When 3-pentenenitrile and adiponitrile are produced by the above-mentioned process, reaction byproducts and catalyst degradation byproducts may also be produced. Unreacted reactants may also become entrained in the effluent from reaction zones used to produce pentenenitriles and adiponitrile.

Certain compounds in effluents from reaction zones are referred to herein as low, intermediate or high boilers.

As used herein, the term "low boilers" refers to compounds having a lower boiling point than the listed boiling point of 2-methyl-3-butenenitrile, i.e. 125° C. Examples of such low boilers include 1-butene, 1,3 butadiene, trans-2-butene, hydrogen cyanide, and cyclohexane. 1-butene has a listed boiling point of −6.3° C. 1,3-butadiene has a listed boiling point of −4.5° C. Trans-2-butadiene has a listed boiling point of 1° C. Hydrogen cyanide has a listed boiling point of 25.7° C. Cyclohexane has a listed boiling point of 80.7° C. (Z)-2M2BN has a listed boiling point of 121.6° C.

Compounds having a boiling point between 147° C. and 295° C. are referred to herein as intermediate boilers. The listed boiling point for 3-penetenenitrile may be as high as 147° C. 295° C. is the listed boiling point for adiponitrile. Examples of compounds which are intermediate boilers include $C_9$ mononitriles, phenol, cresols, TBC, MGN and ESN. $C_9$ mononitriles encompass a broad range of compounds having boiling points between 147 and 295° C. Phenol and cresols have listed boiling points of between 180 and 210° C. Tertiary-butylcatachol (TBC) has a listed boiling point of 285° C. Methylglutaronitrile, especially 2-methyl-glutaronitrile (MGN), has a listed boiling point of 269-271° C. 2-Ethylsuccinonitrile (ESN) has a listed boiling point of 264° C.

High boilers have a listed boiling point above that of adiponitile, i.e. 295° C. Examples of high boilers include TTP or MTTP, phosphorus containing ligand degradation products, $Ni(CN)_2$, $ZnCl_2$ and triphenylboron.

Effluents from reaction zones, $Z_1$, $Z_2$ and $Z_3$, include low boilers, intermediate boilers and high boilers. Desired products, such as 3-pentenenitrile and adiponitrile, need to be purified, in that solutions of these desired products need to be separated from impurities, which are low boilers, intermediate boilers and high boilers. Catalyst, which is to be recycled, also needs to be purified or regenerated by removing certain reaction byproducts and catalyst degradation byproducts from streams including solutions of catalyst.

Reaction byproducts produced in the first reaction zone ($Z_1$) include $C_8H_{13}C{\equiv}N$ compounds. These $C_8H_{13}C{\equiv}N$ compounds may be produced by dimerization of 1,3-butadiene and hydrocyanation of such dienes. $C_8H_{13}C{\equiv}N$ compounds may be separated from catalyst in the extraction zone used to purify the catalyst from the first reaction zone ($Z_1$) or the second reaction zone ($Z_2$) or both the first reaction zone ($Z_1$) and the second reaction zone ($Z_2$). $C_8H_{13}C{\equiv}N$ compounds generally have normal boiling points within the range of 150° C. to 295° C.

The reaction product from the first reaction zone ($Z_1$) may comprise one or more phenolic compounds of the formula

where $R^1$ is H or an alkyl group having 1 to 4 carbon atoms, and n is 0 to 4, provided that when the phenolic compound of formula (II) has more than one alkyl group, these alkyl groups may be the same or different. Examples of such phenolic compounds include phenol and cresols. In particular, cresols are used to make TTP ligands, and both phenol and cresols are used to make MTTP ligands. Consequently, cresols may be present as impurities when the first phosphorus-containing ligand is TTP, and both phenol and cresols may be present as impurities when the first phosphorus-containing ligand is MTTP. Cresols may also be produced in the first reaction zone ($Z_1$) or at another point upstream of the extraction zone by unwanted hydrolysis of TTP ligands. Furthermore, both phenol and cresols may also be produced in the first reaction zone ($Z_1$) or at another point upstream of the extraction zone by unwanted hydrolysis of MTTP ligands. The phenol and cresol impurities have an approximate boiling point falling within the range of 180° C. to 210° C. By limiting the amount of phenolic compounds of formula (II) entering into the third reaction zone ($Z_3$), degradation of the third catalyst, particularly the third phosphorus-containing ligand, may be reduced.

In the distillation steps upstream of the extraction zone, compounds such as 3PN and 2M3BN, having boiling points less than, for example, 150° C., are separated from a higher boiling, catalyst-containing stream. Since tertiary-butylcatechol, $C_8H_{13}C{\equiv}N$ compounds, phenol and cresols have boiling points higher than 150° C., they may pass along with catalyst in the distillation train upstream of the extraction zone. However, when tertiary-butylcatechol, $C_8H_{13}C{\equiv}N$ compounds, phenol and cresols are present, significant amounts of these compounds are taken up in the raffinate phase of the extraction zone. $C_8H_{13}C{\equiv}N$ compounds, phenol and cresols in the raffinate phase may be separated from dinitriles in the distillation train used to produce a dinitrile recycle stream to be passed into the extraction zone.

Catalyst Purification

Buildup of catalyst degradation products and reaction byproducts may be reduced by a particular way of purifying a catalyst used for hydrocyanating 1,3-butadiene in a process for making adiponitrile. The catalyst may be purified in a liquid/liquid extraction treatment. In particular, separate extraction zones may be used to purify the first and third catalysts. In FIG. 1, these zones are represented by extraction zone 150 and extraction zone 370.

Addition of Make-Up Catalyst

During the course of the reaction in the first reaction zone ($Z_1$), as well as in subsequent processing of the reactor effluent, for example, during distillation, a portion of the first catalyst may degraded or lost. There is a need to replenish catalyst which is degraded or lost. As shown in FIG. 1, catalyst which has been lost by degradation is replenished after the extraction treatment. In FIG. 1, make-up catalyst is added to catalyst recycle stream 146 through line 145 after the catalyst passes through extraction zone 150. However, it will be understood that catalyst, which passes through extraction zone 150, may be provided with make-up catalyst and reintroduced into reaction system in different locations.

Removal of $C_8H_{13}C{\equiv}N$ Compounds

Reaction byproducts produced during the reaction of 1,3-butadiene and HCN in a first reaction zone ($Z_1$) include $C_8H_{13}C{\equiv}N$ compounds. These $C_8H_{13}C{\equiv}N$ compounds may be produced by dimerization of 1,3-butadiene and hydrocyanation of such dimers. When such $C_8H_{13}C{\equiv}N$ compounds are introduced into a reaction zone for producing adiponitrile by the reaction of 3PN with HCN, these $C_8H_{13}C{\equiv}N$ compounds may react with HCN to produce unwanted $C_8H_{14}(C{\equiv}N)_2$ compounds. Methods for removing these $C_8H_{13}C{\equiv}N$ compounds are discussed below.

$C_8H_{13}C{\equiv}N$ compounds are separated from a first catalyst in a liquid/liquid extraction zone. In FIG. 1, this separation takes place in extraction zone 150. $C_8H_{13}C{\equiv}N$ compounds which enter into the raffinate stream may, in turn, be removed by distillation. In FIG. 2, $C_8H_{13}C{\equiv}N$ compounds are removed from adiponitrile in column $K_4$ via stream 420.

A significant amount of the $C_9$ mononitriles in the raffinate stream entering separation sections 1000 and 2000, through lines 510 and 710, respectively, may pass into line 420, along with MGN.

$C_9$ mononitriles may not completely separate from pentenenitriles in a distillation step used to remove pentenenitriles from $C_9$ mononitriles. Accordingly, pentenenitriles removed from higher boiling components of the raffinate phase by distillation may contain some $C_9$ mononitriles. Pentenenitriles removed from higher boiling components of the raffinate phase may be treated to remove $C_9$ mononitriles. Pentenenitriles removed from higher boiling components of the raffinate phase may be used to prepare make-up catalyst for recycle into the first reaction zone ($Z_1$), the second reaction zone ($Z_2$) or both the first reaction zone ($Z_1$) and the second reaction zone ($Z_2$).

The effluent from the first reaction zone of step (a) may be distilled in a single distillation column to provide a stream enriched in 2M3BN and a stream enriched in both 3-pentenenitrile and $C_9$ mononitriles. The stream enriched in 3-pentenenitrile and $C_9$ mononitriles may be distilled to separate the 3-pentenenitrile from the $C_9$ mononitriles.

The effluent from the first reaction zone of step (a) may be distilled in a single distillation column to provide (i) a stream enriched in 2M3BN, (ii) a stream enriched in 3-pentenenitrile and (iii) a stream enriched in $C_9$ mononitriles. The stream enriched in 2M3BN may be taken as a top draw, the stream enriched in 3-pentenenitrile may taken as a side draw, and the stream enriched in $C_9$ mononitriles may be taken as a bottom draw.

In the context of this specification, a $C_9$ mononitrile is generally defined as an aliphatic mononitrile compound comprising a total of nine carbon atoms ($C_9$). A $C_9$ mononitrile with a carbon-carbon double bond is capable of further reacting with hydrogen cyanide to produce a $C_{10}$ dinitrile, such as $C_8H_{14}(C{\equiv}N)_2$. Without being limited by theory, it is theorized that $C_9$ mononitriles are various isomers of diolefinic acyclic $C_9$ mononitrile compounds with the chemical formula $C_8H_{13}C{\equiv}N$ and monoolefinic cyclic $C_9$ mononitrile compounds with the chemical formula $C_8H_{13}C{\equiv}N$. Compounds with the chemical formula $C_8H_{13}C{\equiv}N$ may arise by combining two 1,3-butadiene molecules with one hydrogen cyanide molecule.

Gas chromatographic (GC) methods to quantify the amounts of five carbon pentenenitrile isomers (produced from 1,3-butadiene hydrocyanation and 2-methyl-3-butenenitrile isomerization) and six carbon dinitriles (produced from pentenenitrile hydrocyanation) in a process sample may also be used to quantify $C_9$ mononitrile compounds. Dependent upon the GC column utilized, the $C_9$ mononitriles can appear as GC peaks with retention times between those peaks for 3-pentenenitrile and adiponitrile; an observation that is consistent with these $C_9$ mononitriles possessing boiling points, at a given set of conditions, that are intermediate between the boiling point of 3-pentenenitrile and the boiling point of adiponitrile at the same conditions. Using GC/mass spectroscopy with electron impact ionization method, the observation of one or more positive ions selected from the group consisting of m/e (mass/charge ratio)=135 $[C_8H_{13}C{\equiv}N]+$, 134 $[C_8H_{13}C{\equiv}N$ minus H$]+$, 120 $[C_8H_{13}C{\equiv}N$ minus $CH_3]+$, 106 $[C_8H_{13}C{\equiv}N$ minus $C_2H_5]+$, 95 $[C_8H_{13}C{\equiv}N$ minus $CH_2C{\equiv}N]+$, 94 $[C_8H_{13}C{\equiv}N$ minus $C_3H_5]+$, and 81 $[C_8H_{13}C{\equiv}N$ minus $C_2H_4C{\equiv}N]+$ can then be used to identify which of these peaks comprise a $C_9$ mononitrile and thereby quantify the amounts of $C_9$ mononitriles in a process sample by GC analysis.

During 3-pentenenitrile hydrocyanation to produce adiponitrile in the presence of nickel complexes of phosphorus-containing ligands and Lewis acid, GC analyses provide evidence that certain $C_9$ mononitrile compounds with a carbon-carbon double bond may also be hydrocyanated to produce aliphatic dinitrile compounds with a total of ten carbon atoms ($C_{10}$). Without being limited by theory, it is believed that these $C_{10}$ dinitriles are various isomers of monoolefinic acyclic $C_{10}$ dinitrile compounds with the chemical formula $C_8H_{14}(C{\equiv}N)_2$ and cyclic $C_{10}$ dinitrile compounds with the chemical formula $C_8H_{14}(C{\equiv}N)_2$.

The $C_{10}$ dinitriles appear as GC peaks with retention times before and after a retention time for 1,6-dicyanohexane [eight carbon dinitrile] utilized as a GC internal standard. Using GC/mass spectroscopy with electron impact ionization method, the observation of one or more positive ions selected from the group consisting of m/e (mass/charge ratio)=162 $[C_8H_{14}(C{\equiv}N)_2]+$, 161 $[C_8H_{14}(C{\equiv}N)_2$ minus H$]+$, 147 $[C_8H_{14}(C{\equiv}N)_2$ minus $CH_3]+$, 135 $[C_8H_{14}(C{\equiv}N)_2$ minus $C_2H_3]+$ or $[C_8H_{14}(C{\equiv}N)_2$ minus $HC{\equiv}N]+$, 134 $[C_8H_{14}(C{\equiv}N)_2$ minus $C_2H_4]+$, 122 $[C_8H_{14}(C{\equiv}N)_2$ minus $CH_2C{\equiv}N]+$, 121 $[C_8H_{14}(C{\equiv}N)_2$ minus $C_3H_5]+$, 120 $[C_8H_{14}(C{\equiv}N)_2$ minus $C_3H_6]+$, 119 $[C_8H_{14}(C{\equiv}N)_2$ minus $C_3H_7]+$, and 105 $[C_8H_{14}(C{\equiv}N)_2$ minus $C_4H_9]+$ can then be used to identify which of these peaks comprise a $C_{10}$ dinitrile and thereby quantify the amounts of $C_{10}$ dinitriles in a process sample by GC analysis.

Removal of Tertiary-Butylcatechol

Tertiary-butylcatechol (TBC) is a polymerization inhibitor, which inhibits the polymerization of 1,3-butadiene, particularly while the 1,3-butadiene is in storage. Commercial sources of 1,3-butadiene often include small amounts of TBC to inhibit polymerization of 1,3-butadiene.

TBC may react with certain phosphorus-containing ligands, such as monodentate phosphite ligands and bidentate phosphite ligands. Hydrocyanation catalysts may comprise phosphorus-containing ligands which are reactive with TBC.

European Patent Publication No. 1 344 770 describes problems with TBC reacting with hydrocyanation catalysts comprising phosphite, phosphonite and phosphinite ligands. The problem is pronounced with bidentate ligands, because these ligands tend to be used in small quantities and are expensive. EP 1 344 770 describes the removal of TBC by a variety of techniques, including vaporization or passing liquid 1,3-butadiene over an absorbent bed, such as alumina.

TBC may be separated from a first catalyst in a liquid/liquid extraction zone. In FIG. 1, this separation takes place in extraction zone 150. TBC which enters into the raffinate stream may, in turn, be removed by distillation. In FIG. 2, TBC, along with methylglutaronitrile is removed from adiponitrile in column $K_4$ via stream 420. However, since TBC tends to boil at a temperature in between boiling temperatures for methylglutaronitrile and adiponitrile, removal of TBC by distillation may be difficult and at least a portion of the tertiary-butylcatechol in the raffinate stream in line 515 may require several passes through the dinitrile recovery loop to be removed. For example, tertiary-butylcatechol may pass into extraction zone 150 along with the dinitrile-enriched stream in line 500. However, since tertiary-butylcatechol is relatively polar, for example, in comparison with cyclohexane, it tends to separate into the raffinate phase in extraction zone 150. In this way, tertiary-butylcatechol is prevented from passing downstream, for example, into the third reaction zone ($Z_3$) shown in FIG. 1. The boiling point of MGN is within the range of 269° C. to 271° C., the boiling point of tertiary-butylcatechol is 285° C., and the boiling point of adiponitrile is 295° C. Accordingly, by controlling the distillation conditions in column $K_4$, at least a portion of any tertiary-butylcatechol in the raffinate stream may be removed along with MGN in line 420.

Removal of Phenolic Compounds

Phenolic compounds, such as phenol and cresols, may be present as a catalyst impurity in catalysts used to react BD with HCN or to isomerize 2M3BN. Phenolic compounds may be produced by hydrolysis of phosphorus-containing ligands. Phenolic compounds may react with ligands in catalysts used to react 3PN with HCN. Such reactions of phenolic compounds with catalyst ligands may result in reduced yields or efficiency in the reaction of 3PN with HCN.

Phenolic compounds are removed from reaction streams upstream from a reaction zone used to react 3PN with HCN.

Phenolic compounds are separated from a first catalyst in a liquid/liquid extraction zone. In FIG. 1, this separation takes place in extraction zone 150. Phenolic compounds which enter into the raffinate stream may, in turn, be removed by distillation. In FIG. 2, phenolic compounds are removed from adiponitrile in column $K_4$ via stream 420.

The first phosphorus-containing ligand, the second phosphorus-containing ligand and the third phosphorus-containing ligand may be a ligand which is reactive with a phenolic compound, such as phenol or cresol. Such reactive ligands may be a phosphite ligand or a phosphonite ligand or a phosphinite ligand.

A phenolic compound may be an impurity in the source of first phosphorus-containing ligand. For example, TTP (i.e. tris(tolyl)phosphite) or MTTP may be made by reacting at least one phenolic compound of formula (II) with $PCl_3$. When the phenolic compound is an impurity in the source of first phosphorus-containing ligand, phenolic compound is fed into step (a) along with said first phosphorus-containing ligand.

A phenolic compound may be produced by a hydrolysis reaction, which degrades catalyst. Certain phosphorus-containing ligands in catalysts, such as a phosphite ligand or a phosphonite ligand or a phosphinite ligand, react with water to produce a phenolic compound. For example, TTP (i.e. tris(tolyl)phosphite) reacts with water to produce cresols, and MTTP reacts with water to produce a mixture of phenol and cresols. A phenolic compound and a phosphorus-containing ligand degradation product may be produced by a hydrolysis reaction occurring upstream of the third reaction zone. For example, the hydrolysis reaction may take place in the first reaction zone or downstream of the first reaction zone, for example, in a distillation column. A phosphorus-containing ligand degradation product may also be produced by an oxidation reaction or both an oxidation and hydrolysis reaction occurring upstream of the third reaction zone.

If water or another protic compound, such as tertiary-butylcatechol, is present in the system upstream from the point where the purge stream is taken, phenolic compounds may be produced by hydrolysis or reaction of the first phosphorus-containing ligand with a protic compound. If phenolic compounds are produced, they may be present in the catalyst recycle stream 140 and the catalyst purge stream 126. Phenolic compounds, introduced into the first reaction zone ($Z_1$) along with first phosphorus-containing ligand, may also be present in the catalyst recycle stream 140 and catalyst purge stream 126. At least a portion of the phenolic compounds of formula (II) will be will be extracted into the raffinate phase in extraction zone 150 along with certain reaction by-products and certain catalyst degradation products, for example, produced by oxidation of the first catalyst.

Removal of Phosphorus-Containing Ligand Degradation Products

When a hydrocyanation catalyst comprises a phosphorus-containing ligand, the ligand may degrade as a result of a hydrolysis or oxidation reaction. Such hydrolysis or oxidation reactions produce unwanted impurities. Hydrolysis and oxidation products of phosphorus-containing ligands are discussed in U.S. Pat. No. 3,773,809.

Phosphorus-containing ligand degradation products are removed from reaction streams upstream from a reaction zone used to react 3PN with HCN.

Phosphorus-containing ligand degradation products are separated from a first catalyst in a liquid/liquid extraction zone. In FIG. 1, this separation takes place in extraction zone 150. Phosphorus-containing ligand degradation products which enter into the raffinate stream may, in turn be removed by distillation. In FIG. 2, Phosphorus-containing ligand degradation products are removed from dinitriles in column $K_3$ via stream 640.

Removal of Methylglutaronitrile (MGN)

When 1,3-butadiene is reacted with hydrogen cyanide to produce 3-pentenenitrile, which is a mononitrile compound, small amounts of dinitrile compounds, including adiponitrile (ADN) and methylglutaronitrile (MGN), may also be produced. Build-up of methylglutaronitrile may cause problems associated with catalyst purification and recycle, catalyst/ligand stability and catalyst thermal sensitivity in reboilers of distillation columns.

Build-up of methylglutaronitrile (MGN) is minimized by a particular way of removing MGN produced in a reaction of 1,3-butadiene with hydrogen cyanide.

MGN is separated from a first catalyst in a liquid/liquid extraction zone. In FIG. 1, this separation takes place in extraction zone 150. MGN which enters into the raffinate stream may, in turn, be removed by distillation. In FIG. 2, MGN is removed from adiponitrile in column $K_4$ via stream 420.

Preventing Lewis Acid from Entering the First Reaction Zone ($Z_1$)

Pentenenitriles, such as 3-pentenenitrile and 2-methyl-3-butenenitrile, are produced in the reaction of 1,3-butenenitrile with hydrogen cyanide in the presence of a catalyst. However, in this reaction, dinitriles, such as adiponitrile and methylglutaronitrile, are also produced as byproducts. If Lewis acid promoters are present during this reaction of BD with HCN, the production of dinitriles, including methylglutaronitrile, is increased. When unwanted methylglutaronitrile is produced during the course of reacting 1,3-butadiene with HCN, valuable 1,3-butadiene reactant, which would otherwise be converted to wanted adiponitrile, is effectively lost.

3-pentenenitrile and 2-methyl-3-butenenitrile may be separated from catalyst and recovered by distillation. The separated catalyst may be recycled. However, dinitriles are more difficult to separate from catalyst and tend to build up in the catalyst recycle stream. Build-up of dinitriles in a reactor for hydrocyanating 1,3-butadiene may reduce the effective reactor volume, thereby negatively affecting the reaction efficiency. Also, build-up of dinitriles in concentrated catalyst compositions, such as those present in certain distillation column bottoms, may cause catalyst to decompose or precipitate.

The consequences of unwanted production of dinitriles and unwanted build-up of dinitriles in a catalyst recycle stream are minimized by limiting the flow of Lewis acid into a reaction zone for reacting 1,3-butadiene with hydrogen cyanide. The consequences of unwanted build-up of dinitriles in a catalyst recycle stream may further be minimized by removing methylglutaronitrile from the catalyst recycle stream.

Hydrocyanation of 1,3-Butadiene in the First Reaction Zone $Z_1$

As shown in FIG. 1, 1,3butadiene (BD) containing feedstock may be fed to the first reaction zone ($Z_1$), e.g., via line 100, a hydrogen cyanide feed may be fed to the first reaction zone ($Z_1$), e.g., via line 120, and a first catalyst may be fed to the first reaction zone ($Z_1$), e.g., via line 140.

The 1,3-Butadiene Feedstock

The 1,3-butadiene feedstock may comprise at least 98 wt % 1,3-butadiene based on the total weight of the feedstock, preferably at least 99 wt %, and more preferably at least 99.5 wt %. In one embodiment, the feedstock comprises from 99.5 to 99.9 wt % 1,3-butadiene based on the total weight of the feedstock. The balance of the feedstock may comprise residual levels of undesirable impurities, such as butane, butenes, 1,2-butadiene and acetylenes such as propyne. The feedstock may also comprise tertiary-butylcatechol (TBC), for example, 4-tert-butylcatechol. At least 95% of the TBC may be present in the form of 4-tert-butylcatechol. A portion of TBC present in the feedstock may optionally be removed before charging the 1,3-butadiene to the first reaction step. The BD-containing feed may comprise less than a total of 100 ppm acetylenes.

The HCN Feed

The HC≡N feed to the first reaction zone ($Z_1$) and the third reaction zone ($Z_3$) may be a product of the Andrussow process that is dried to less than about 250 ppm water, for example, less than 125 ppm water, for example, less than 80 ppm water, by distillation prior to entry into olefin hydrocyanation reaction zones. However, the HCN feed will usually contain at least some water. Very dry HCN is unstable and, for this reason, it may be undesirable to provide completely anhydrous HCN. Accordingly, the HCN feed may comprise at least 10 ppm, for example, at least 25 ppm, for example, at least 50 ppm, water.

The hydrogen cyanide (HC≡N) is preferably substantially free of carbon monoxide, oxygen and ammonia. This HC≡N can be introduced to the first reaction zone ($Z_1$) and the third reaction zone ($Z_3$) as a vapor, liquid, or mixtures thereof; see, for example, European Patent Publication No. 1 344 770. As an alternative, a cyanohydrin can be used as the source of HC≡N; see, for example, U.S. Pat. No. 3,655,723.

Equipment in the First Reaction Zone ($Z_1$)

The HC≡N feed, the BD-containing feed, and the catalyst composition are contacted in a reaction zone which may be contained in any suitable equipment known to one skilled in the art. One or more pieces of conventional equipment may be used to provide the reaction zone, for example continuous stirred-tank reactors, loop-type bubble column reactors, gas circulation reactors, bubble column reactors, tubular reactors, or combinations thereof, optionally with apparatus for removing at least a portion of the heat of reaction.

Reaction Conditions in the First Reaction Zone ($Z_1$)

A non-oxidizing and anhydrous environment retards oxidative deactivation of the catalyst. Accordingly, a dry inert atmosphere, e.g., nitrogen, is normally used, although air may be used at the expense of loss of a portion of the catalyst through oxidation and hydrolysis.

The 1,3-butadiene (BD) hydrocyanation is preferably conducted using BD substantially free of oxygen, acetylenes and water. BD can be introduced to the hydrocyanation reaction zone as a vapor, liquid, or mixtures thereof; see, for example, European Patent Publication No. 1 344 770. BD may be at least partially depleted of tertiary-butylcatechol prior to contacting the catalyst.

The BD hydrocyanation reaction temperature is typically maintained within the range of about −25° C. to about 200° C., for example, within the range of about 0° C. to about 150° C. Generally, the reaction pressure should be sufficient to maintain the BD and HC≡N in contact with the catalyst dissolved in the liquid reaction mixture, with such pressure at least, in part, being a function of the amount of unreacted BD present in the reaction mixture. Though the disclosed process is not limited by an upper limit of pressure for this reaction step, for practical purposes the pressure may generally range from about 15 psia to about 300 psia (about 1.03 bar to about 20.7 bar).

The overall feed molar ratio of the BD to HC≡N may be in the range of about 1:1 to about 100:1, for example, in the range of about 1:1 to about 2:1. Excess BD within the reaction zone may decrease the formation of dinitriles during the BD hydrocyanation reaction.

The feed molar ratio of HC≡N to catalyst in the reaction of HC≡N with BD may be in the range of about 5:1 to about 100,000:1, for example, in the range about 100:1 to about 5,000:1.

In an embodiment where the first catalyst comprises a monodentate ligand, the molar ratio of monodentate ligand to nickel in the catalyst for the reaction of HC≡N with BD may be from about 4:1 to about 50:1, for example, from about 4:1 to about 30:1, for example, from about 4:1 to about 15:1.

The residence time in the BD hydrocyanation reaction zone is typically determined by the desire to obtain a certain degree of conversion of BD, HC≡N, or a combination thereof. The BD hydrocyanation reaction zone may comprise one or more physical reactors. For example, the BD hydrocyanation zone may include a one or more plug flow reactors in combination with one or more continuous stirred tank reactors. When a reactor is used that substantially provides the mixing characteristics of a continuous stirred tank reactor, "residence time" is the time necessary for the combined feeds to displace one reactor volume for this reaction step. In addition to residence time, catalyst concentration and reaction temperature will also affect conversion of reactants to products. Generally, residence times will be in the range of about 0.1 hour to about 15 hours, for example, in the range of about 1 hour to about 10 hours. The HC≡N conversion may be, for example, greater than 99%. Generally, BD conversion in the BD hydrocyanation reaction zone may be less than 99%, for example, between 80 and 95% overall, for example 90% overall. Staged HCN addition within the hydrocyanation reaction zone may be used.

Distillation of the Reactor Effluent from the First Reaction Zone ($Z_1$)

The reaction product mixture from the BD hydrocyanation reaction zone, including BD, 3PN, 2M3BN, and catalyst, may be distilled in one or more distillation apparatus to recover a BD-enriched stream, pentenenitrile-enriched stream including 3PN and 2M3BN, and catalyst-enriched stream including the catalyst. The BD-enriched and catalyst-enriched streams may be recycled to the BD hydrocyanation reaction. The pentenenitrile-enriched stream may be further distilled to obtain a 2M3BN-enriched stream and a 2M3BN-depleted stream including 3PN.

The 2M3BN-enriched stream from the BD hydrocyanation process may be a 2M3BN feed to the 2M3BN isomerization process. In FIGS. 1 and 4, this 2M3BN-enriched stream is represented by stream 200. The 2M3BN-depleted stream including 3PN may be used as a 3PN feed to the third reaction zone ($Z_3$). A 2M3BN-depleted stream including 3PN is represented in FIG. 4 as stream 838.

As noted above, the reaction of 1,3-butadiene and hydrogen cyanide in the presence of a first catalyst in a first reaction zone ($Z_1$) produces a first reaction effluent (stream 122) comprising 1,3-butadiene, 3-pentenenitrile, 2-methyl-3-butenenitrile, and first catalyst. These components of the reaction effluent may be separated, at least partially, by one or more distillation steps, represented, schematically, by separation section 125 in FIG. 1. An example of separation section 125 is shown in greater detail in FIG. 4. In particular, these distillation steps may take place in one or more distillation columns, to provide:

1) at least one 1,3-butadiene-enriched stream 812 and 824;
2) a first 2-methyl-3-butenenitrile-enriched stream 200;
3) a first 3-pentenenitrile-enriched stream 838; and
4) a first catalyst-enriched stream 140.

These streams are enriched with a particular component in that they have greater concentrations of these components than the effluent from the first reaction zone ($Z_1$) in line 122. For example, the first catalyst-enriched stream 140 has a greater concentration of catalyst than the effluent stream in line 122. The first 2-methyl-3-butenenitrile-enriched stream 200 and first 3-pentenenitrile-enriched stream 838 may each contain less than a total of 500 parts per million by weight of phosphorus-containing ligand, for example, less than 350 parts per million by weight of phosphorus-containing ligand, for example, less than 200 parts per million by weight of phosphorus-containing ligand. If an excessive amount of dinitriles is present in the effluent of-from the first reaction zone ($Z_1$), catalyst may thermally degrade, causing the nickel/ligand complex to disassociate in column bottoms of distillation apparatus used to obtain the first catalyst-enriched stream 140.

At least partial separation of a 3-pentenenitrile and 2-methyl-3-butenenitrile mixture from at least one phosphorus-containing ligand may be achieved by a distillation process. For example, this separation may be facilitated by a distillation apparatus comprising a feed inlet; an upper draw outlet; and a bottom draw outlet. A phosphorus-containing ligand stream, such as stream 813 comprising 3PN, 2M3BN, and at least one catalyst including a phosphorus-containing ligand, may be flowed into a feed stage of the first distillation apparatus through the feed inlet. The distillation apparatus may include a stripping section, a rectifying section or both. There may be at least one stage of separation between the feed inlet and the upper draw outlet. A pentenenitrile-enriched stream comprising 3-pentenenitrile and 2-methyl-3-butenenitrile may be withdrawn from the upper draw outlet. This stream is depleted of the at least one phosphorus-containing ligand, relative to the phosphorus-containing ligand stream fed to the distillation column. A pentenenitrile-depleted stream may be withdrawn from the bottom draw outlet. This pentenenitrile-depleted stream is enriched with the phosphorus-containing ligand, relative to the phosphorus-containing ligand stream fed to the distillation column. The first distillation apparatus may be operated such that the pentenenitrile-depleted stream comprises at least 5% by weight of pentenenitrile including the sum of 3-pentenenitrile and 2-methyl-3-butenenitrile.

The pentenenitrile-enriched stream comprising 3-pentenenitrile and 2-methyl-3-butenenitrile may be distilled in a second distillation apparatus to obtain a 2-methyl-3-butenenitrile-enriched stream as a top product and a 2-methyl-3-butenenitrile-depleted stream (i.e. a 3-pentenenitrile-enriched stream) as a bottom product.

The first 3-pentenenitrile-enriched stream may comprise small amounts of 2-methyl-3-butenenitrile. These small amounts of 2-methyl-3-butenenitrile may be separated from 3-pentenenitrile in one or more distillations columns, where 2-methyl-3-butenenitrile is recovered as a top product and 3-pentenenitrile is recovered as a bottom product. For example, two or more 3-pentenenitrile-enriched streams may be combined and distilled in a single or shared distillation column or these streams may be distilled in separate distillation columns. 2-methyl-3-butenenitrile recovered from such distillation may be passed as feed to the second reaction zone ($Z_2$), and 3-pentenenitrile recovered from such distillation may be passed as feed to the third reaction zone ($Z_3$).

Distillation of the Effluent from $Z_1$ to Optimize Removal of Intermediate Boilers Removal of intermediate boilers, such as MGN, $C_8H_{13}C\equiv N$ compounds, phenol and cresols, from the reaction system may be facilitated by distilling the reaction product stream from the first reaction zone ($Z_1$) in a particular manner. For example, after removing unreacted 1,3-butadiene and hydrogen cyanide from the reaction product stream from the first reaction zone ($Z_1$), the stream, comprising pentenenitriles, zero valent nickel and first phosphorus-containing ligand, may be fed into a distillation column having a feed inlet, an upper draw outlet, and a bottom draw outlet. The distillation column may have a stripping section, a rectifying section or both. A rectifying section comprising at least one stage of separation is provided between the feed inlet and the upper draw outlet. A pentenenitrile-enriched stream is withdrawn from the upper draw outlet. A catalyst-enriched stream is withdrawn from the bottom draw outlet. The distillation column is operated in a manner such that the catalyst-enriched stream comprises at least 5% by weight of pentenenitrile including the sum of 3-pentenenitrile and 2-methyl-3-butenenitrile. In this way, intermediate boilers tend to pass into the catalyst-enriched stream. These compounds may then be removed at least in part from the reaction system by the extraction process into the raffinate and from the raffinate by the raffinate treatment process described above.

In a modification of this process for distilling the reaction product stream from the first reaction zone ($Z_1$) depleted of 1,3-butadiene and hydrogen cyanide, the distillation column is further provided with a side draw outlet. A rectifying section comprising at least two stages of separation is provided between the feed inlet and the upper draw outlet. A pentenenitrile-enriched stream is withdrawn from the upper draw outlet. A catalyst-enriched stream is withdrawn from the bottom inlet. The distillation column is further provided with a liquid collection apparatus, such as a chimney tray, in the rectifying section. Liquid in the liquid collection apparatus of the rectifying section is collected at a location between the feed stage and upper draw outlet. At least a portion of the collected liquid is withdrawn to obtain the side-draw stream. The distillation column may be operated in a manner such that the catalyst-enriched stream comprises at least 5% by weight of pentenenitrile including the sum of 3-pentenenitrile and 2-methyl-3-butenenitrile. The distillation column may also be operated in a manner such that dinitriles and intermediate boilers, such as MGN, $C_8H_{13}C\equiv N$ compounds, phenol and cresols, tend to pass out of the column through the side draw outlet. The stream from the side draw may then be passed either directly or indirectly into an extraction system. In another embodiment, the stream from the side draw is passed to a distillation column to selectively remove phenols, cresols and $C_8H_{13}C\equiv N$ compounds. In this way, at least a portion of the $C_8H_{13}C\equiv N$ compounds, phenol and cresols are separated from recycled catalyst.

Recycle and Purification of the First Catalyst

The first catalyst-enriched stream passes from separation section 125 through line 140. A portion of this catalyst enriched stream in line 140 is withdrawn forming a first catalyst purge stream, which passes through line 126. This purge stream comprises the first catalyst, catalyst degradation product and reaction byproduct. At least a portion of the first catalyst from the first catalyst purge in line 126 is fed to a first catalyst regeneration zone comprising liquid-liquid extraction to at least partially separate catalyst degradation product and reaction byproduct from the first catalyst.

At least 80%, preferably at least 90%, for example, 93 to 96%, at least 99%, at least 99.9%, and substantially all of the first catalyst in stream 140 is recycled. A portion of the first catalyst recycle stream 140 is withdrawn in purge stream 126 for purification and recovery. In embodiments of the disclosed process, the minimum amount of circulating catalyst that is withdrawn, purified, recovered and optionally treated to increase its nickel content is selected from 2, 5, 10, 15 and 20% by weight of the circulating catalyst. In other embodiments, less than 100, 75, 50 and 25% by weight of the circulating catalyst can be withdrawn, purified, recovered and optionally treated to increase its nickel content. The purified and recovered catalyst is then returned to either the first ($Z_1$) or second ($Z_2$) reaction zone.

The purification steps as applied to the first and third catalysts are segregated, in order to avoid (at least reducing to de minimis levels as described herein above) co-mingling of the first catalyst with the third catalyst in the first ($Z_1$) and second ($Z_2$) reaction zones, and also the third ($Z_3$) reaction zone.

The process conducted in a catalyst regeneration zone may comprise the steps of:
1) introducing a dinitrile stream comprising dinitrile and an extraction solvent stream comprising extraction solvent into an extraction zone;
2) contacting the catalyst purge with extraction solvent from the extraction solvent stream and dinitrile from the dinitrile stream in the extraction zone to obtain within the extraction zone at least two immiscible liquid phases including an extract phase and a raffinate phase;
3) withdrawing from the extract phase an extract stream comprising extraction solvent and catalyst;
4) withdrawing from the raffinate phase a raffinate stream comprising dinitrile, catalyst degradation product and reaction byproduct;
5) distilling the extract stream to obtain at least one extraction solvent-enriched stream and an extraction solvent-depleted stream (i.e. a catalyst-enriched stream) comprising separated catalyst; and
6) optionally, distilling the raffinate phase in one or more steps to purge catalyst degradation products and to provide a dinitrile stream depleted in such catalyst degradation products. Catalyst degradation products may have lower or higher boiling points than the adiponitrile, and this optional distillation step may be configured accordingly by one of ordinary skill given the vapor-liquid equilibrium data for the components to be distilled.

Purification or regeneration of catalyst results in removal of catalyst degradation products. Such catalyst degradation products may include one or more of, for example, one or more phosphorus-containing ligand hydrolysis products, e.g., phenol and substituted phenol, one or more phosphorus-containing ligand oxidation products, such as phosphates derived from the oxidation of phosphite ligands, $Ni(C\equiv N)_2$, ligand hydrolysis products and nickel metal.

Purification or regeneration of catalyst also results in removal of reaction byproducts. Examples of such reaction byproducts include a $C_8H_{13}C\equiv N$ compound, 2-methyl-2-butenenitrile, 2-pentenenitrile, 2-methylglutaronitrile, and ethylsuccinonitrile.

The First Extraction Zone

A first extraction zone is shown in FIG. 1. A catalyst purge stream 126 is fed into liquid/liquid extraction zone 150. A non-polar solvent, such as an alkane, is fed into the liquid/liquid extraction zone 150 through line 130. A polar solvent, which is immiscible with the non-polar solvent, is also fed into the liquid/liquid extraction zone 150 through line 500. The polar solvent introduced into extraction zone 150 through line 500 comprises adiponitrile. The catalyst purge stream 126 comprises reaction byproducts and catalyst degradation byproducts formed in the first reaction zone ($Z_1$). In extraction zone 150, there is formed a non-polar phase comprising non-polar solvent and catalyst and a polar phase (e.g., a raffinate) comprising polar solvent and, for example, reaction byproducts and catalyst degradation products. The non-polar phase is taken from extraction zone 150 via line 134 to distillation column 155. The polar phase is taken from extraction zone 150 via line 510 to separation section 1000.

The extraction solvent provided to the extraction zone may be at least one hydrocarbon compound selected from the group consisting of linear aliphatic, branched aliphatic, unsubstituted cycloaliphatic, and alkyl-substituted cycloaliphatic hydrocarbons. Such extraction solvents may boil in the range of 30° C. to 135° C., for example, from 60° C. to 100° C., at a pressure of one atmosphere. The dinitrile feed to the extraction zone may be mainly composed of adiponitrile. MGN and ESN may be at least partially removed from the dintrile stream prior to recycling to the liquid/liquid extraction zone.

The extraction zone may comprise a plurality of extraction stages. A catalyst purge stream and, optionally, a side-draw stream comprising intermediate boilers may be charged into different extraction stages of the extraction zone. The side-draw stream may be generated during the distillation of pentenenitriles containing catalyst to obtain a pentenenitrile-enriched stream as an upper draw and a catalyst-enriched stream as a lower draw. Both the catalyst purge stream and the side-draw stream may comprise dinitriles and intermediate boilers, such as $C_8H_{13}C\equiv N$ compounds, phenol and cresols. Extract and raffinate phases may flow in a counter-current fashion within the extraction zone. The above-mentioned side-draw stream comprising intermediate boilers may be charged into a multiple stage extraction zone and into an extraction stage closer than the first stage to the extraction stage where the raffinate phase is withdrawn. Extraction solvent may be charged to the same extraction stage of the extraction zone where the raffinate phase is withdrawn from the extraction zone to obtain the raffinate stream. The catalyst-enriched stream may be charged to the same extraction stage of the extraction zone where the extract phase is withdrawn from the extraction zone to obtain the extract stream. In a multistage extraction zone, a portion of the catalyst enriched stream may also be charged to the same extraction stage of the extraction zone where the raffinate phase is withdrawn from the extraction zone to obtain the raffinate stream.

A stream comprising make-up catalyst from a make-up catalyst reactor may also be introduced to the catalyst loop downstream of the extraction zone. In a multi-stage extraction zone, comprising, for example, at least 3, for example, at least 4, for example, at least 5 extraction stages, make-up phosphite ligand of the catalyst may be introduced near the stage where the catalyst purge stream is charged.

In the extraction zone, wherein an extract phase and a raffinate phase are produced, the molar ratio of total moles of mononitrile compounds divided by total moles of dinitrile compounds should be sufficient to achieve this phase separation. For example, this molar ratio may be between 0 and 0.5, for example, 0.005 to 0.5, for example, 0.01 to 0.25, for example, 0.05 to 0.20, for example, 0.05 and 0.15, for example, 0.1 and 0.5. The mononitriles in the extraction zone may include 4-pentenenitrile, 3-pentenenitrile, 2-pentenenitrile, 2-methyl-3-butenenitrile, 2-methyl-2-butenenitrile, and valeronitrile. The dinitriles in the extraction zone may include adiponitrile, 2-methylglutaronitrile, and ethylsuccinonitrile. In order to achieve proper extraction of catalyst into the extraction solvent phase, the flow of catalyst enriched stream into the extraction zone and the flow of the extraction solvent phase from the extraction zone should be controlled. Also, the flow of catalyst enriched stream into the extraction zone and the flow of the extraction solvent into the extraction zone should be controlled. For example, the ratio of mass flow of extraction solvent entering the extraction zone divided by sum of the mass flows of the dinitrile and catalyst feed to the extraction zone for the contacting may be less than about 2, for example, less than 1.5, for example, less than 1.2. Further, the flow of raffinate stream withdrawn from the extraction zone and the flow of the catalyst stream into the extraction zone should be controlled. For example, the ratio of mass flow of raffinate stream withdrawn from the extraction zone divided by mass flow of the pentenenitrile-depleted stream entering the extraction zone for the contacting may be greater than about 0.9. U.S. Pat. No. 3,773,809 to Walter teaches an example of a suitable liquid/liquid extraction process.

The temperature in the extraction zone to facilitate phase separation and catalyst extraction may be from 25° C. to 135° C., for example, 25° C. to 90° C., for example, 50° C. to 75° C. The concentration of mononitriles in the extraction zone (e.g., from the combined catalyst enriched stream and dinitrile stream) may be between 2-20%, for example, 5-15%, by weight of total mononitriles, for example, where the mononitrile component is calculated as the sum of the weights of mononitrile compounds comprising 2-pentenenitrile, 3-pentenenitrile, 4-pentenenitrile, 2-methyl-3-butenenitrile, 2-methyl-2-butenenitrile, and valeronitrile.

Recycle of Extraction Solvent

Non-polar solvent may be distillatively recovered and recycled to the extraction zone for purifying (i.e. regenerating) catalyst. For example, as shown in FIG. 1, non-polar solvent may be distillatively recovered in distillation column 155 and returned to extraction zone 150, via line 130. Extraction zone 150, line 134, distillation column 155 and line 130, collectively, form a recovery loop for recycling non-polar solvent into extraction zone 150. Extraction zone 150, line 510, separation section 1000 and line 500, collectively, form a recovery loop for recycling polar solvent into extraction zone 150.

The extract stream may be distilled in at least one distillation column at 1 psia to 22 psia (0.07 bar to 1.5 bar) pressure and with a base temperature of less than about 160° C., for example, less than about 150° C., for example, less than about 140° C. The base temperature is chosen in part to maintain the thermal stability of the catalyst composition.

Distillation of the Raffinate from the First Reaction Zone ($Z_1$)

The raffinate stream from the extraction zone may be distilled in one or more distillation columns to separate dinitriles from other components of the raffinate stream, such as extraction solvent, pentenenitriles, reaction byproducts and catalyst degradation products. Dinitriles separated from the other components of the raffinate stream may then be recycled to the extraction zone.

Distillation of the raffinate phase is shown in FIG. 2, as described above.

Although a majority of the extraction solvent separates into the solvent phase in the extraction zone, some extraction solvent is extracted into the raffinate phase. The raffinate stream, therefore, comprises some extraction solvent. The raffinate stream may further comprise one or more of at least one pentenenitrile (typically a mixture of pentenenitriles), tertiary-butylcatechol, $C_8H_{13}C\equiv N$ compounds, phenol, cresols, and dinitriles comprising adiponitrile (ADN) and methylglutaronitrile (MGN). In a first distillation step of the raffinate stream, extraction solvent having a lower boiling point than pentenenitriles may be separated from other higher boiling constituents of the raffinate stream to obtain an extraction solvent depleted raffinate stream. Such extraction solvents may have a boiling point of, for example, 30 to 135° C., for example, 60 to 100° C. An example of such an extraction solvent is cyclohexane, which has a boiling point (BP) of 81° C.

In a second distillation step of the raffinate stream, pentenenitrile may be removed from other higher boiling components of the raffinate stream to obtain a pentenenitrile-depleted raffinate stream. This pentenenitrile-depleted raffinate stream may comprise, for example, a total of at least 0.01%, for example, at least 0.07%, for example, at least 0.1%, for example, less than 1%, by weight of pentenenitrile including the sum of 4-pentenenitrile, 3-pentenenitrile, and 2-pentenenitrile. Examples of pentenenitriles, which may be removed as an overhead stream in this second distillation step include 2-methyl-3-butenenitrile, trans-3-pentenenitrile, cis-3-pentenenitrile, trans-2-pentenenitrile, and cis-2-pentenenitrile. Such removed pentenenitriles may have an approximate boiling point within the range of from 120° C. to 150° C. The column may be operated under conditions sufficient to keep a majority of the intermediate boilers, such as $C_9$ mononitriles, in the pentenenitrile-depleted stream. These conditions may involve operating the column such that at least some pentenenitrile is included in the pentenenitrile depleted stream.

The pentenenitrile-depleted raffinate stream obtained in the above-mentioned second distillation step may be introduced into at least a third distillation step. In this third distillation step, compositions having a higher boiling point than dinitriles are separated as a bottom stream from the dinitriles and compounds, such as tertiary-butylcatechol, $C_8H_{13}C\equiv N$ compounds, phenol and cresols, if present. Such bottoms products may have a boiling point of, for example, at least 300° C. In contrast, most dinitriles in the pentenenitrile-depleted raffinate stream from the above-mentioned second distillation step would tend to have a boiling point within the approximate range of 260° C. to 300° C.

The third distillation step of the raffinate stream may occur in one or more distillation columns. In an example of using a single distillation column for this third distillation step, compounds having a boiling point of, for example, less than 250° C. are withdrawn as an overhead stream, compounds having a boiling point of, for example, from 260° C. to 300° C. are withdrawn as a side draw from the distillation column, and compounds having a boiling point of, for example, greater than 300° C. are withdrawn as a bottom stream. In this example of a third distillation step, the overhead stream may comprise compounds, such as $C_8H_{13}C\equiv N$ compounds, phenol and cresols, the side stream may comprise compounds, such as tertiary-butylcatechol and dinitriles, and the bottoms stream may comprise compounds, such as catalyst degradation products, including for example, $Ni(CN)_2$ and an organophosphate formed by oxidation of an organophosphite ligand. For example, tris(tolyl)phosphate is an oxidation byproduct of tris(tolyl)phosphite.

This separation may also take place in two distillation columns. When two distillation columns are used for the third distillation step, a first distillation column may be operated to produce a bottoms stream comprising compounds having a boiling point of greater than 300° C. and an overhead stream comprising dinitriles and, for example, $C_8H_{13}C\equiv N$ compounds, phenol and cresols. This overhead stream may then be passed to a second distillation column to produce dinitriles as a bottoms stream and an overhead stream comprising $C_8H_{13}C\equiv N$ compounds, phenol and cresols.

When the dinitrile stream from the third distillation step comprises methylglutaronitrile (MGN), in particular, 2-methylglutaronitrile (2-MGN), this stream may be further distilled to remove MGN from this stream to thereby produce a stream enriched in adiponitrile for recycle to the extraction zone. 2-MGN has an approximate boiling point of 269° C. to 271° C., whereas adiponitrile has an approximate boiling point of 295° C. Tertiary-butylcatechol, especially 4-tertiary-butylcatechol, has a boiling point of 285° C. The overhead cut point of the above-mentioned third distillation step for treating the raffinate stream may also be adjusted such that MGN is removed along with $C_8H_{13}C\equiv N$ compounds, phenol and cresols, as an overhead of the single distillation column with a side draw or as an overhead in of the second distillation column, when two columns are used. Removing MGN from the adiponitrile prevents unwanted buildup of MGN. The removal of MGN also facilitates the removal of $C_8H_{13}C\equiv N$ compounds, phenol and cresols from the catalyst recycle stream and the entire reaction system. Removing MGN further facilitates removal of any 2-ethylsuccinonitrile, an isomer of ADN and MGN. The boiling point of 2-ethylsuccinonitrile is 264° C. At least a portion of any tertiary-butylcatechol in the dinitrile stream may be removed with the MGN. The MGN-containing stream recovered from the distillation column may be further purified by removing impurities, such as phenols, cresols and TBC. The purified MGN may be commercially sold. MGN is useful as a solvent/intermediate in the fiber industry.

Although particular distillation steps are described above for converting the raffinate stream from the extraction zone into a purified adiponitrile stream, which is, in turn, recycled to the extraction zone, it will be understood that other distillation steps are possible. It is within the ordinary skill in the art to design and operate such steps. Streams of compounds removed from the adiponitrile in the raffinate may be disposed of, further refined, used in a different reaction process or recycled to an appropriate point in the overall reaction system.

Bottoms comprising catalyst degradation products from the above-mention third distillation step may passed to a wiped film evaporator (WFE) to recover adiponitrile in such bottoms. A wiped film evaporator may also be used to recover adiponitrile from catalyst degradation products in an adiponitrile recovery section 3000. Catalyst degradation products from separation section 1000 and separation section 2000 may be fed to a wiped film evaporator in adiponitrile recovery section 3000 to recover adiponitrile in all of the concentrated catalyst degradation products, separated from dinitriles in these sections.

Introduction of Recycled Catalyst into the First Reaction Zone ($Z_1$)

After catalyst has passed through a distillation apparatus for distilling non-polar solvent from catalyst, the purified (i.e. regenerated) catalyst may be recycled to the first reaction zone. When the first and second catalysts comprise the same phosphorus-containing ligand, at least a portion of the purified (i.e. regenerated), second catalyst may be recycled to the first reaction zone. For example, referring to FIG. 1, column bottoms from distillation column 155 include partially purified catalyst. This partially purified catalyst may be taken from distillation column 155 through lines 156 and 146 for introduction into catalyst recycle line 140 for recycle into the first reaction zone ($Z_1$). Optionally, a side stream may be taken from line 246 into line 200 or 240, and this side stream may be used as a catalyst feed to the second reaction zone ($Z_2$). Any partially purified stream of first catalyst, which is subsequently fed to the second reaction zone ($Z_2$), may be provided with additional zero-valent Ni, for example, and/or first phosphorus-containing ligand, via line 245. Although not shown in FIG. 1, line 245 may optionally be fed directly into line 246 or line 248 instead of line 240.

The composition of the column bottoms from column 155 in line 156 may comprise, for example, 1-2 wt % zero valent Ni, 70-90 wt % phosphorus-containing ligand, less than 4 wt % of the non-polar solvent, such a cyclohexane, used in the extraction zone 150, less than 10 wt % pentenenitriles, and less than 10 wt % dinitriles.

Isomerization of 2-Methyl-3-Butenenitrile in the Second Reaction Zone ($Z_2$)

As shown in FIG. 1, 2-methyl-3-butenenitrile (2M3BN)) containing feedstock may be fed to the second reaction zone ($Z_2$), e.g., via line 222, and a second catalyst may be fed to the second reaction zone ($Z_2$), e.g., via line 240.

In a second reaction zone ($Z_2$) at least a portion of the first 2-methyl-3-butenenitrile-enriched stream is reacted in the presence of a second catalyst, comprising a zero-valent nickel and at least one phosphorus-containing ligand. In FIG. 1, this first 2-methyl-3-butenenitrile-enriched stream passes from separation section 125 to the second reaction zone ($Z_2$) through line 200. FIG. 1 does not show lines for withdrawing the above-mentioned first 3-pentenenitrile-enriched stream and 1,3-butadiene-enriched stream from separation section 125. The first 3-pentenenitrile-enriched stream may, for example, by-pass the second reaction zone ($Z_2$) and be fed directly into the third reaction zone ($Z_3$) or to a feed line, such as line 300, shown in FIG. 1 for introducing feed into the third reaction zone ($Z_3$). As mentioned above, the 1,3-butadiene-enriched stream may be recycled back into the first reaction zone ($Z_1$).

The 2-Methyl-3-Butenenitrile Feed

The 2-methyl-3-butenenitrile feed to the second reaction zone ($Z_2$) is obtained from distillation steps described herein above. This feed may comprise at least 30 wt % 2M3BN. This feed may also comprise less than 70 wt % of pentenenitriles other than 2M3BN, and less than 1 wt % of the first phosphorus-containing ligand, for example, less than 0.1 wt. %.

Equipment in the Second Reaction Zone ($Z_2$)

The 2M3BN-containing feed and the catalyst composition are contacted in a reaction zone which may be contained in any suitable equipment known to one skilled in the art. One or more pieces of conventional equipment may be used to provide the reaction zone, for example continuous stirred-tank reactors, loop-type bubble column reactors, gas circulation reactors, bubble column reactors, tubular reactors, or combinations thereof, optionally with apparatus for removing at least a portion of the heat of reaction.

Reaction Conditions in the Second Reaction Zone ($Z_2$)

The feed molar ratio of 2M3BN to catalyst for the isomerization reaction step is generally greater than 1:1, usually in the range from about 5:1 to 20,000:1, for example, from about 100:1 to about 5,000:1.

When a monodentate ligand is used, the molar ratio of monodentate ligand to zero valent nickel in the catalyst for the isomerization reaction may be from about 1:1 to about 50:1, for example, from about 1:1 to about 30:1. When a bidentate ligand is used, the molar ratio of bidentate ligand to zero valent nickel in the catalyst for the isomerization reaction may be from 1:1 to 10:1, for example, from 1:1 to 5:1.

The residence time in the reaction zone for the isomerization reaction may be from about 0.1 hour to about 15 hours, for example, from about 1 hour to about 10 hours.

For the isomerization of 2M3BN to produce 3PN, the reaction temperature may be maintained within the range of about 0° C. to about 200° C., for example, within the range of about 50° C. to about 165° C. Again, though the invention is not limited by an upper limit of pressure for this reaction step, for practical purposes the pressure generally ranges from about 15 psia to about 300 psia (about 1.03 bar to about 20.7 bar).

Distillation of the Reactor Effluent from the Second Reaction Zone ($Z_2$)

The reaction product mixture from the 2M3BN isomerization reaction zone may include certain light boilers, 3PN, 2M3BN, (Z)-2M2BN and catalyst. At least some of the light boilers may be removed in a first distillation step. Then, a stream depleted in light boilers may be distilled in one or more distillation apparatus to recover a (Z)-2M2BN-enriched stream, a (Z)-2M2BN-depleted stream including 3PN and 2M3BN, and a catalyst-enriched stream including the catalyst. At least a portion of the catalyst-enriched stream may be recycled to the 2M3BN isomerization reaction.

The (Z)-2M2BN-depleted stream may be further distilled to obtain a 2M3BN-enriched stream and a 2M3BN-depleted stream including 3PN. The 2M3BN-enriched stream from the BD hydrocyanation process may be a 2M3BN feed to the 2M3BN isomerization process.

The effluent from the second reaction zone ($Z_2$) comprises 3-pentenenitrile, 2-methyl-3-butenenitrile and the second catalyst. In FIG. 1, this effluent from the second reaction zone ($Z_2$) passes through line 222. These components of the reaction effluent may be separated, at least partially by one or more distillation steps, represented, diagrammatically, by separation section 225 in FIG. 1. An example of separation section 225 is shown in greater detail in FIG. 5. In particular, these distillation steps may take place in one or more distillation columns, to provide:

1) a second 2-methyl-3-butenenitrile-enriched stream 967;
2) a second 3-pentenenitrile-enriched stream 300; and
3) a second catalyst-enriched stream 240.

The second 2-methyl-3-butenenitrile-enriched stream and the second 3-pentenenitrile-enriched stream may each contain less than a total of 500 parts per million by weight of the phosphorus-containing ligand. For example, the second 3-pentenenitrile-enriched stream may contain less than 300 ppm, for example, less than 100 ppm, of the phosphorus-containing ligand.

The second 3-pentenenitrile-enriched stream may comprise small amounts of 2-methyl-3-butenenitrile. These small amounts of 2-methyl-3-butenenitrile may be separated from 3-pentenenitrile in one or more distillations columns, where 2-methyl-3-butenenitrile is recovered as a top product and 3-pentenenitrile is recovered as a bottom product. For example, the first and second 3-pentenenitrile-enriched streams may be combined and distilled in a single or shared distillation column or these streams may be distilled in separate distillation columns. 2-methyl-3-butenenitrile recovered from such distillation may be passed as feed to the second reaction zone (4), and 3-pentenenitrile recovered from such distillation may be passed as feed to the third reaction zone ($Z_3$).

The second 3-pentenenitrile-enriched stream may further comprise (Z)-2-methyl-2-butenenitrile and the second 3-pentenenitrile-enriched stream may be distilled to obtain a (Z)-2-methyl-3-butenenitrile-enriched stream, comprising 2-methyl-3-butenenitrile and (Z)-2-methyl-2-butenenitrile, along with other low boilers as described previously, as a top product, and a (Z)-2-methyl-2-butenenitrile-depleted stream, comprising 3-pentenenitrile, 2-methyl-3-butenenitrile, and, depending on distillation conditions, some (Z)-2-methyl-2-butenenitrile, as a bottom product.

At least one distillation system for distilling the effluent from the second reaction zone ($Z_2$) is described above. However, it will be understood that it is within the skill in the art to design and operate other distillation systems to achieve the same or essentially the same results. For example, a stream comprising 3PN and 2M3BN obtained by distilling the effluent from the second reaction zone ($Z_2$) may be passed to a distillation apparatus, such as distillation apparatus 830, used in the distillation of the effluent form the from the first reaction zone ($Z_1$), to obtain a 3PN-enriched stream and a 2M3BN-enriched stream.

At least a portion of the second 3-pentenenitrile-enriched stream may be used to prepare a catalyst solution. In particular, at least a portion of the second 3-pentenenitrile-enriched stream may be passed into a catalyst reaction zone, wherein nickel metal reacts with the phosphorus-containing ligand to produce a catalyst solution, comprising catalyst and pentenenitriles. A portion of this catalyst solution may be passed into the second reaction zone ($Z_2$). When the first and second catalysts comprise the same phosphorus-containing ligand, a portion of the catalyst may be passed to the first reaction zone ($Z_1$).

Recycle and Purification of the Second Catalyst

The second catalyst-enriched stream passes from separation section 225 through line 240. A portion of this catalyst enriched stream in line 240 is withdrawn forming a second catalyst purge stream, which passes through line 226. This purge stream comprises the second catalyst, catalyst degradation product and reaction byproduct. At least a portion of the second catalyst from the second catalyst purge stream in line 226 may be fed to a second catalyst regeneration zone comprising liquid-liquid extraction to at least partially separate catalyst degradation product and reaction byproduct from a separated first catalyst. According to an option not shown in FIG. 1, at least a portion of the second catalyst purge in line 226 may be fed to a first catalyst regeneration zone. In such an option, the second catalyst regeneration zone may be omitted.

At least 10%, for example, at least 50%, for example, 75%, for example, 80% to 90%, of the second catalyst in stream 240 is recycled, and the remaining amount in purge stream 226 is withdrawn for purification and recovery. In one embodiment, 20 to 60% by weight of the circulating catalyst can be withdrawn, purified, recovered and optionally treated to increase its nickel content. The purified and recovered catalyst is then returned to either the first ($Z_1$) or second ($Z_2$) reaction zone. Depending upon the activity of the second catalyst, one embodiment of the disclosed process may include charging the second catalyst to the second reaction zone ($Z_2$) and not recycling it.

The process conducted in a catalyst regeneration zone may comprise the steps of:

1) introducing a dinitrile stream comprising dinitrile and an extraction solvent stream comprising extraction solvent into an extraction zone;
2) contacting the catalyst purge with extraction solvent from the extraction solvent stream and dinitrile from the dinitrile stream in the extraction zone to obtain within the extraction zone at least two immiscible liquid phases including an extract phase and a raffinate phase;
3) withdrawing from the extract phase an extract stream comprising extraction solvent and catalyst;
4) withdrawing from the raffinate phase a raffinate stream comprising dinitrile, catalyst degradation product and reaction byproduct;
5) distilling the extract stream to obtain at least one extraction solvent-enriched stream and an extraction solvent-depleted stream (i.e. a catalyst-enriched stream) comprising separated catalyst; and
6) optionally, distilling the raffinate phase in one or more steps to purge catalyst degradation products and to provide a dinitrile stream depleted in such catalyst degradation products. Catalyst degradation products may have lower or higher boiling points than the adiponitrile and this optional distillation step may be configured accordingly by one of ordinary skill given the vapor-liquid equilibrium data for the components to be distilled.

Purification or regeneration of catalyst results in removal of catalyst degradation products. Such catalyst degradation products include one or more of, for example, one or more phosphorus-containing ligand hydrolysis products, e.g., phenol and substituted phenol, one or more phosphorus-containing ligand oxidation products, such as phosphates derived from the oxidation of phosphite ligands, Ni(C≡N)$_2$, ligand hydrolysis products and nickel metal.

Purification or regeneration of catalyst also results in removal of reaction byproducts. Examples of such reaction byproducts include a $C_8H_{13}C$≡N compound, 2-methyl-2-butenenitrile, 2-pentenenitrile, 2-methylglutaronitrile, and ethylsuccinonitrile.

The Second Extraction Zone

A second extraction zone is shown in FIG. 1. A catalyst purge stream 226 is fed into liquid/liquid extraction zone 250. A non-polar solvent, such as an alkane, is fed into the liquid/liquid extraction zone 250 through line 230. A polar solvent, which is immiscible with the non-polar solvent, is also fed into the liquid/liquid extraction zone 250 through line 700. The polar solvent introduced into extraction zone 250 through line 700 comprises reaction byproducts and catalyst degradation byproducts formed in the first reaction zone ($Z_1$). In extraction zone 250, there is formed a non-polar phase comprising non-polar solvent and catalyst and a polar phase (e.g., a raffinate) comprising polar solvent and, for example, reaction byproducts and catalyst degradation products. The non-polar phase is taken from extraction zone 250 via line 234 to distillation column 255. The polar phase is taken from extraction zone 250 via line 710 to separation section 2000.

The extraction solvent provided to the extraction zone may be at least one hydrocarbon compound selected from the group consisting of linear aliphatic, branched aliphatic, unsubstituted cycloaliphatic, and alkyl-substituted cycloaliphatic hydrocarbons. Such extraction solvents may boil in the range of 30° C. to 135° C., for example, 60° C. to 100° C., at a pressure of one atmosphere. The dinitrile feed to the extraction zone may be mainly composed of adiponitrile. MGN and ESN may be removed from the dintrile stream prior to recycle to the liquid/liquid extraction zone. However, even when MGN and ESN are removed, small amounts of MGN and ESN may still be present, because these isomers of adiponitrile may not be completely removed in the distillation process used to treat the raffinate stream.

The extraction zone may comprise a plurality of extraction stages. A catalyst purge stream and, optionally, a side-draw stream comprising intermediate boilers may be charged into different extraction stages of the extraction zone. The side-draw stream may be generated during the distillation of pentenenitriles containing catalyst to obtain a pentenenitrile-enriched stream as an upper draw and a catalyst-enriched stream as a lower draw. Both the catalyst purge stream and the side-draw stream may comprise dinitriles and intermediate boilers, such as $C_8H_{13}C$≡N compounds, phenol and cresols. Extract and raffinate phases may flow in a counter-current fashion within the extraction zone. The above-mentioned side-draw stream comprising intermediate boilers may be charged into a multiple stage extraction zone and into an extraction stage closer than the first stage to the extraction stage where the raffinate phase is withdrawn. Extraction solvent may be charged to the same extraction stage of the extraction zone where the raffinate phase is withdrawn from the extraction zone to obtain the raffinate stream. The catalyst-enriched stream may be charged to the same extraction stage of the extraction zone where the extract phase is withdrawn from the extraction zone to obtain the extract stream. In a multistage extraction zone, a portion of the catalyst enriched stream may also be charged to the same extraction stage of the extraction zone where the raffinate phase is withdrawn from the extraction zone to obtain the raffinate stream.

A stream comprising make-up ligand may also be introduced into the extraction zone.

In the extraction zone, wherein an extract phase and a raffinate phase are produced, the molar ratio of total moles of mononitrile compounds divided by total moles of dinitrile compounds should be sufficient to achieve this phase separation. For example, this ratio may be between 0 and 0.5, for example, 0.005 to 0.5, for example, 0.01 to 0.25, for example, 0.05 to 0.20, for example, 0.05 and 0.15, for example, 0.1 and 0.5. The mononitriles in the extraction zone may include 4-pentenenitrile, 3-pentenenitrile, 2-pentenenitrile, 2-methyl-3-butenenitrile, 2-methyl-2-butenenitrile, and valeronitrile. The dinitriles in the extraction zone may include adiponitrile, 2-methylglutaronitrile, and ethylsuccinonitrile. In order to achieve proper extraction of catalyst into the extraction solvent phase, the flow of catalyst enriched stream into the extraction zone and the flow of the extraction solvent phase from the extraction zone should be controlled. Ratios of extraction solvents and catalyst charged to the extraction zone are substantially the same as described above for extraction zone 150. The boiling point of the dinitrile may be greater than a boiling point of 3-pentenenitrile at a given pressure. Examples of such dinitrile compounds include adiponitrile, 2-methylglutaronitrile, ethylsuccinonitrile, and mixtures of these dinitriles. The temperature in the extraction zone to facilitate phase separation and catalyst extraction may be from 25° C. to 135° C., for example, for example, 25° C. to 90° C., for example, 50° C. to 75° C. The concentration of mononitriles in the extraction zone (e.g., from the combined catalyst enriched stream and dinitrile stream) may be between 2-20%, for example, 5-15%, by weight of total mononitriles, for example, where the mononitrile component is calculated as the sum of the weights of mononitrile compounds comprising 2-pentenenitrile, 3-pentenenitrile, 4-pentenenitrile, 2-methyl-3-butenenitrile, 2-methyl-2-butenenitrile, and valeronitrile.

Recycle of Extraction Solvent

Non-polar solvent may be distillatively recovered and recycled to the extraction zone for purifying (i.e. regenerating) catalyst. For example, as shown in FIG. 1, non-polar solvent may be distillatively recovered in distillation column 255 and returned to extraction zone 250, via line 230. Extraction zone 250, line 234, distillation column 255 and line 230, collectively, form a recovery loop for recycling non-polar solvent into extraction zone 250. Extraction zone 250, line 710, separation section 2000 and line 700, collectively, form a recovery loop for recycling polar solvent into extraction zone 250.

The extract stream may be distilled in at least one distillation column at 1 psia to 22 psia (0.07 bar to 1.5 bar) pressure and with a base temperature of less than about 160° C., for example, less than about 150° C., for example, less than about 140° C., for example, less than about 130° C., or, for example, less than about 120° C. The base temperature is chosen in part to maintain the thermal stability of the catalyst composition.

Distillation of the Raffinate from the Second Reaction Zone ($Z_2$)

The raffinate stream from the extraction zone may be distilled in one or more distillation columns to separate dinitriles from other components of the raffinate stream, such as extraction solvent, pentenenitriles, reaction byproducts and catalyst degradation products. Dinitriles separated from the other components of the raffinate stream may then be recycled to the extraction zone.

Distillation of the raffinate phase is shown in FIG. 2, as described above.

Although a majority of the extraction solvent separates into the solvent phase in the extraction zone, some extraction solvent is extracted into the raffinate phase. The raffinate stream, therefore, comprises some extraction solvent. The raffinate stream may further comprise one or more of at least one pentenenitrile (typically a mixture of pentenenitriles), tertiary-butylcatechol, $C_8H_{13}C\equiv N$ compounds, phenol, cresols, and dinitriles comprising adiponitrile (ADN) and methylglutaronitrile (MGN). In a first distillation step of the raffinate stream, extraction solvent having a lower boiling point than pentenenitriles may be separated from other higher boiling constituents of the raffinate stream to obtain an extraction solvent depleted raffinate stream. Such extraction solvents may have a boiling point of, for example, from 30 to 135° C., for example, from 60 to 100° C. An example of such an extraction solvent is cyclohexane, which has a boiling point (BP) of 81° C.

In a second distillation step of the raffinate stream, pentenenitrile may be removed from other higher boiling components of the raffinate stream to obtain a pentenenitrile-depleted raffinate stream. This pentenenitrile-depleted raffinate stream may comprise, for example, a total of at least 0.01%, for example, at least 0.07%, for example, at least 0.1%, for example, less than 1%, by weight of pentenenitrile including the sum of 4-pentenenitrile, 3-pentenenitrile, and 2-pentenenitrile. Examples of pentenenitriles, which may be removed as an overhead stream in this second distillation step include 2-methyl-3-butenenitrile, trans-3-pentenenitrile, cis-3-pentenenitrile, trans-2-pentenenitrile, and cis-2-pentenenitrile. Such removed pentenenitriles may have an approximate boiling point within the range of from 120° C. to 150° C.

The pentenenitrile-depleted raffinate stream obtained in the above-mentioned second distillation step may be introduced into at least a third distillation step. In this third distillation step, compositions having a higher boiling point than dinitriles are separated as a bottom stream from the dinitriles and compounds, such as tertiary-butylcatechol, $C_8H_{13}C\equiv N$ compounds, phenol and cresols, if present. Such bottoms products may have a boiling point of, for example, at least 300° C. In contrast, most dinitriles in the pentenenitrile-depleted raffinate stream from the above-mentioned second distillation step would tend to have a boiling point within the approximate range of 260° C. to 300° C.

The third distillation step of the raffinate stream may occur in one or more distillation columns. In an example of using a single distillation column for this third distillation step, compounds having a boiling point of, for example, less than 250° C. are withdrawn as an overhead stream, compounds having a boiling point of, for example, from 260° C. to 300° C. are withdrawn as a side draw from the distillation column, and compounds having a boiling point of, for example, greater than 300° C. are withdrawn as a bottom stream. In this example of a third distillation step, the overhead stream may comprise compounds, such as $C_8H_{13}C\equiv N$ compounds, phenol and cresols, the side stream may comprise compounds, such as tertiary-butylcatechol and dinitriles, and the bottoms stream may comprise compounds, such as catalyst degradation products, including for example, $Ni(CN)_2$ and an organophosphate formed by oxidation of an organophosphite ligand. For example, tris(tolyl)phosphate is an oxidation byproduct of tris(tolyl)phosphite.

This separation may also take place in two distillation columns. When two distillation columns are used for the third distillation step, a first distillation column may be operated to produce a bottoms stream comprising compounds having a boiling point of greater than 300° C. and an overhead stream comprising dinitriles and, for example, $C_8H_{13}C\equiv N$ compounds, phenol and cresols. This overhead stream may then be passed to a second distillation column to produce dinitriles as a bottoms stream and an overhead stream comprising lower boilers, such as $C_8H_{13}C\equiv N$ compounds, phenol and cresols.

When the dinitrile stream from the third distillation step comprises methylglutaronitrile (MGN), in particular, 2-methylglutaronitrile (2-MGN), this stream may be further distilled to remove MGN from this stream to thereby produce an essentially pure adiponitrile stream for recycle to the extraction zone. 2-MGN has an approximate boiling point of 269° C. to 271° C., whereas adiponitrile has an approximate boiling point of 295° C. Tertiary-butylcatechol, especially 4-tertiary-butylcatechol, has a boiling point of 285° C. The overhead cut point of the above-mentioned third distillation step for treating the raffinate stream may also be adjusted such that MGN is removed along with $C_8H_{13}C\equiv N$ compounds, phenol and cresols, as an overhead of the single distillation column with a side draw or as an overhead in of the second distillation column, when two columns are used. Removing MGN from the adiponitrile prevents unwanted buildup of MGN. The removal of MGN also facilitates the removal of $C_8H_{13}C\equiv N$ compounds, phenol and cresols from the catalyst recycle stream and the entire reaction system. Removing MGN further facilitates removal of any 2-ethylsuccinonitrile, an isomer of ADN and MGN. The boiling point of 2-ethylsuccinonitrile is 264° C. At least a portion of any tertiary-butylcatechol in the dinitrile stream may be removed with the MGN.

Although particular distillation steps are described above for converting the raffinate stream from the extraction zone into a purified adiponitrile stream, which is, in turn, recycled to the extraction zone, it will be understood that other distillation steps are possible. It is within the ordinary skill in the art to design and operate such steps. Streams of compounds removed from the adiponitrile in the raffinate may be disposed of, further refined, used in a different reaction process or recycled to an appropriate point in the overall reaction system.

Bottoms comprising catalyst degradation products from the above-mention third distillation step may passed to a wiped film evaporator (WFE) to recover adiponitrile in such bottoms. A wiped film evaporator may also be used to recover adiponitrile from catalyst degradation products in an adiponitrile recovery section 3000. Catalyst degradation products from separation section 1000 and separation section 2000 may be fed to a single wiped film evaporator in adiponitrile recovery section 3000 to recover adiponitrile in all of the concentrated catalyst degradation products, separated from dinitriles in these sections.

Introduction of Recycled Catalyst into the Second Reaction Zone ($Z_2$)

After catalyst has passed through a distillation apparatus for distilling non-polar solvent from catalyst, the purified (i.e. regenerated), second catalyst may be recycled to the second reaction zone. When the first and second catalysts comprise the same phosphorus-containing ligand, at least a portion of the purified (i.e. regenerated), second catalyst may be recycled to the first reaction zone. When the second and third catalysts comprise the same phosphorus-containing ligand, at least a portion of the purified (i.e. regenerated), second catalyst may be recycled to the third reaction zone. For example, referring to FIG. 1, column bottoms from distillation column 255 include partially purified catalyst. This partially purified catalyst may be taken from distillation column 255 through line 248 for introduction into catalyst recycle line 240 for recycle into the second reaction zone ($Z_2$). Optionally, when the first and second catalyst comprise the same phosphorus-containing ligand, a side stream may be taken from line 248 into line 247, and this side stream may be used as a catalyst feed to the first reaction zone ($Z_1$). Any partially purified stream of second catalyst, which is subsequently fed to the first reaction zone ($Z_1$), may be provided with additional zero-valent Ni, for example, and/or first phosphorus-containing ligand, via line 145. Although not shown in FIG. 1, line 145 may optionally be fed directly into line 140 instead of line 146. In an embodiment where second reaction zone ($Z_2$) and the third reaction zone ($Z_3$) share catalyst, the make-up catalyst for the second reaction zone ($Z_2$) may be recovered from the catalyst recycle stream of the third reaction zone ($Z_3$). This embodiment is not illustrated in the Figures.

Hydrocyanation of 3-Pentenenitrile in the Third Reaction Zone $Z_3$

As shown in FIG. 1, 3-pentenenitrile (3PN) containing feedstock may be fed to the third reaction zone ($Z_3$), e.g., via line 300, a hydrogen cyanide feed may be fed to the third reaction zone ($Z_3$), e.g., via line 220, and a third catalyst may be fed to the third reaction zone ($Z_3$), e.g., via line 340. The catalyst feed also comprises a Lewis acid promoter.

A first 3-pentenenitrile stream is obtained from the distillation of the effluent from the first reaction zone ($Z_1$). A second 3-pentenenitrile stream is obtained from the distillation of the effluent of the second reaction zone ($Z_2$). In the third reaction zone ($Z_3$), at least a portion of the first 3-pentenenitrile-enriched stream and the second 3-pentenenitrile-enriched stream is reacted with hydrogen cyanide in the presence of a third catalyst, comprising a zero-valent nickel and at least one phosphorus-containing ligand, and at least one promoter. In FIG. 1, the second 3-pentenenitrile-enriched stream passes from separation section 225 to the third reaction zone ($Z_3$) through line 300. FIG. 1 does not show a line for withdrawing the above-mentioned second 2-methyl-3-butenenitrile-enriched stream and second 1,3-butadiene-enriched stream from separation section 225. The second 2-methyl-3-butenenitrile-enriched stream may, for example, be recycled back into the second reaction zone ($Z_2$).

The 3-Pentenenitrile Feedstock

The 3-pentenenitrile feed to the third reaction zone ($Z_3$) is obtained from distillation steps described herein above. This feed may comprise at least 95 wt % 3PN. This feed may also comprise less than 5 wt % of pentenenitriles other than 3PN, and less than 0.1 wt % of the first phosphorus-containing ligand.

The 3PN feed may comprise less than 5000 parts per million (ppm) $C_9$ mononitriles, for example, less than 2000 parts per million (ppm) $C_9$ mononitriles, for example, less than 1000 parts per million (ppm) $C_9$ mononitriles, for example, less than 600 parts per million (ppm) $C_9$ mononitriles.

The HCN Feed

The HC≡N feed to the first reaction zone ($Z_1$) and the third reaction zone ($Z_3$) may be a product of the Andrussow process that is dried to less than about 250 ppm water, for example, less than 125 ppm water, for example, less than 80 ppm water, by distillation prior to entry into olefin hydrocyanation reaction zones. However, the HCN feed will usually contain at least some water. Very dry HCN is unstable, and it is preferred to use anhydrous HCN Accordingly, the HCN feed may comprise at least 10 ppm, for example, at least 25 ppm, for example, at least 50 ppm, water.

The hydrogen cyanide (HC≡N) is preferably substantially free of carbon monoxide, oxygen and ammonia. This HC≡N can be introduced to the first reaction zone ($Z_1$) and the third reaction zone ($Z_3$) as a vapor, liquid, or mixtures thereof; see, for example, European Patent Publication No. 1 344 770. As an alternative, a cyanohydrin can be used as the source of HC≡N; see, for example, U.S. Pat. No. 3,655,723.

Equipment in the Third Reaction Zone ($Z_3$)

The HC≡N feed, the 3PN-containing feed, and the catalyst composition are contacted in a reaction zone which may be contained in any suitable equipment known to one skilled in the art. One or more pieces of conventional equipment may be used to provide the reaction zone, for example continuous stirred-tank reactors, loop-type bubble column reactors, gas circulation reactors, bubble column reactors, tubular reactors, or combinations thereof, optionally with apparatus for removing at least a portion of the heat of reaction.

Reaction Conditions in the Third Reaction Zone ($Z_3$)

PN hydrocyanation may be performed by reacting HC≡N and 3PN as a vapor, liquid, or mixtures thereof. As an alternative, a cyanohydrin may be used as the source of HC≡N.

The steps for making 3-pentenenitrile and the steps reacting 3-pentenenitrile with hydrogen cyanide need not take place in the same location or facility. For example, the second reaction zone and the third reaction zone may be separated from each other by a distance of at least 500 meters. The third reaction zone may be capable of being operated separately and independently from the first reaction zone and the second reaction zone.

In the 3PN hydrocyanation reaction, promoters are provided to enhance the production of dinitriles. As known in the art, promoters influence both catalyst activity and selectivity to the desired ADN. Promoters employed include salts of metals having atomic numbers 13, 21-32, 39-50, and 57-80, for example, zinc, and compounds of the formula $BR'_3$ wherein R' is an alkyl or an aryl radical of up to 18 carbon atoms, for example triphenylboron, $(C_6H_5)_3B$. The anions of the metal salts include halides, for example chloride, sulfates, phosphates, and lower aliphatic carboxylates. Useful promoters are generally known in the art as Lewis acids. The mole ratio of promoter to nickel in the catalyst is sufficient to promote the hydrocyanation of 3-pentenenitrile, and in one embodiment may be in the range of 1:20 to 50:1, for example, from 0.2:1 to 2:1 when the Lewis acid promoter is $ZnCl_2$.

In the 3PN hydrocyanation process, a 2M3BN-depleted stream from the BD hydrocyanation process, a 2M3BN-depleted stream from the 2M3BN isomerization process, or a combination thereof, is a useful feed stream. The 3PN hydrocyanation reaction temperature may be maintained within the range of about 0° C. to about 150° C., for example, within the range of about 25° C. to about 80° C. Generally, the reaction pressure should be sufficient to maintain the HC≡N in contact with the catalyst dissolved in the liquid reaction mixture. Such pressure is at least, in part, a function of the amount of unreacted HC≡N present in the reaction mixture. While an upper limit of pressure for this reaction step is not limited to any particular pressure, for practical purposes the pressure generally ranges from about 15 psia to about 300 psia (about 1.03 bar to about 20.7 bar).

The overall feed molar ratio of 3PN to HC≡N may be in the range of 1:1 to 100:1, for example, in the range of 1:1 to about 5:1.

The molar ratio of HC≡N to catalyst in the reaction of 3PN with HC≡N may be in the range of 10:1 to 5000:1, for example, 100:1 to 3000:1, for example, in the range 300:1 to 2000:1.

The phosphorus-containing ligand used in the reaction of 3PN with HC≡N is, preferably, a bidentate ligand. The molar ratio of bidentate ligand to nickel in the catalyst for the 3PN hydrocyanation step may be from 1:1 to 10:1, for example, 1:1 to 5:1, for example, 1:1 to 3:1.

The residence time in the 3PN hydrocyanation reaction zone for this reaction step is typically determined by the desire to obtain a certain degree of conversion of pentenenitriles, HC≡N, or a combination thereof. In addition to residence time, catalyst concentration and reaction temperature will also affect conversion of reactants to products. Generally, residence times will be in the range of about 0.1 hour to about 30 hours, for example, in the range of about 1 hour to about 20 hours. The HC≡N conversion may be greater than 99%.

Processing of the Reaction Effluent from the Third Reaction Zone ($Z_3$)

The effluent from the third reaction zone ($Z_3$) comprises adiponitrile, third catalyst, catalyst promoter and catalyst degradation product. In FIG. 1, this reaction effluent from the third reaction zone ($Z_3$) passes through line 400 to liquid/liquid extraction zone 370. One or more stages of distillation (not illustrated) may be included between the third reaction zone ($Z_3$) and liquid/liquid extraction zone 370 to remove lower-boiling constituents including unreacted 3-pentenenitrile. Extraction solvent is fed into extraction zone 370 through line 330. In extraction zone 370 there is formed an extract phase and a raffinate phase. The extract phase comprises the extraction solvent and third catalyst, and the raffinate phase comprises adiponitrile, catalyst degradation products and promoter. The extract phase passes through line 334 to distillation column 375, where extraction solvent is separated from the catalyst. The extraction solvent from distillation column 375 passes through line 330 and is recycled back into extraction zone 370. A catalyst stream is taken from distillation column 375 and is recycled back into the third reaction zone ($Z_3$). The raffinate phase is taken from extraction zone 370 through line 600 into adiponitrile purification section 3000. A purified adiponitrile product stream is recovered via line 660.

The reaction product mixture from the 3PN hydrocyanation reaction zone, including pentenenitriles, such as 3PN, 2PN, and (E)-2M2BN, dinitriles, such as ADN and MGN, catalyst, catalyst degradation products and promoter, may be contacted with a non-polar hydrocarbon extraction solvent in an extraction zone according to a method described in U.S. Pat. Nos. 3,773,809 and 6,936,171. An extract stream including catalyst and extraction solvent and a raffinate stream including extraction solvent, pentenenitriles, dinitriles, catalyst degradation products, and promoter are withdrawn from the extraction zone. The extract stream may be charged to a distillation apparatus.

The extract stream is distilled to obtain a first extraction solvent-enriched stream and a catalyst-enriched stream including the recovered catalyst. The catalyst-enriched stream including nickel complexes of the phosphorus-containing ligand may be recycled to contact 3PN and HC≡N in the presence of the promoter to produce ADN.

The raffinate stream may be distilled in one or more distillation columns to obtain a second extraction solvent-enriched stream, a pentenenitrile-enriched stream including 3PN, a dinitrile-enriched stream, a dinitrile-depleted stream including the catalyst degradation products and promoter, a MGN-enriched stream, and a MGN-depleted stream including the recovered ADN.

Extraction solvent from the first and second extraction solvent-enriched streams may be reused in the extraction zone. Pentenenitrile from the pentenenitrile-enriched stream may be used as a solvent source for preparing the first, second or third catalyst. 3PN may also be separated from the pentenenitrile-enriched stream and may contact catalyst and HC≡N in the presence of the promoter to produce ADN, provided that the 3PN is sufficiently free of $C_8H_{13}C$≡N compounds or compounds, such as phenol or cresols, which are capable of reacting with the phosphorus-containing ligand used in the catalyst for reacting 3PN with HC≡N.

The extract stream may be distilled in at least one distillation column at 1 psia to 22 psia (0.07 bar to 1.5 bar) pressure and with a base temperature of less than about 150° C., for example, less than about 140° C., for example, less than about 130° C., or, for example, less than about 120° C. The base temperature is chosen in part to maintain the thermal stability of the catalyst composition.

Distillation of the raffinate phase is shown in FIG. 3, as described above.

Although a majority of the extraction solvent separates into the solvent phase in the extraction zone, some extraction solvent is extracted into the raffinate phase, which is delivered to distillation column K'$_1$ in FIG. 3 through line 600. The raffinate stream, therefore, comprises some extraction solvent. The raffinate stream 600 may further comprise one or more of at least one pentenenitrile (typically a mixture of pentenenitriles), intermediate boilers and dinitriles comprising adiponitrile (ADN) and methylglutaronitrile (MGN). In a first distillation step of the raffinate stream, extraction solvent (in FIG. 3, withdrawn through stream 625) having a lower boiling point than pentenenitriles may be separated from other higher boiling constituents of the raffinate stream to obtain an extraction solvent depleted raffinate stream, which is withdrawn from column K'$_1$ through line 620. The extraction solvent withdrawn through line 625 may have a boiling point of, for example, from 30 to 135° C., for example, from 60 to 100° C. An example of such an extraction solvent is cyclohexane, which has a boiling point (BP) of 81° C.

In a second distillation step of the raffinate stream, pentenenitrile may be removed from other higher boiling components of the raffinate stream to obtain a pentenenitrile-depleted raffinate stream. In FIG. 3, this pentenenitrile-depleted raffinate stream 630 is obtained by distilling an extraction solvent depleted stream 620 in distillation column K'$_2$. This pentenenitrile-depleted raffinate stream 630 may comprise, for example, a total of at least 0.01% by weight of pentenenitrile including the sum of 4-pentenenitrile, 3-pentenenitrile, and 2-pentenenitrile. Examples of pentenenitriles, which may be removed as an overhead stream 650 in this second distillation step include 2-methyl-3-butenenitrile, trans-3-pentenenitrile, cis-3-pentenenitrile, trans-2-pentenenitrile, and cis-2-pentenenitrile. This pentenenitrile-depleted raffinate stream may comprise, for example, a total of at least 0.01%, for example, 0.07%, for example 0.1%, for example, less than 1%, by weight of pentenenitrile including the sum of 4-pentenenitrile, 3-pentenenitrile, and 2-pentenenitrile. Such removed pentenenitriles may have an approximate boiling point within the range of from 120° C. to 150° C.

The pentenenitrile-depleted raffinate stream 630 obtained in the above-mentioned second distillation step may be introduced into at least a third distillation step. In FIG. 3, this third distillation step takes place in column K'$_3$. In this third distillation step, compositions having a higher boiling point than dinitriles are separated as a bottom stream 640 from dinitriles and any coboilers present, such as intermediate boilers. Such bottoms products in stream 640 may have a boiling point of, for example, at least 300° C. In contrast, most dinitriles in the pentenenitrile-depleted raffinate stream 630 from the above-mentioned second distillation step would tend to have a boiling point within the approximate range of 260° C. to 300° C. These dinitriles and intermediate boilers tend to be withdrawn as an overhead draw through stream 635.

In FIG. 3, stream 635 may then be passed to distillation column K'$_4$ to produce adiponitrile as a bottoms stream 660 and an overhead stream 670 comprising MGN and intermediate boilers.

Stream 640 comprising catalyst degradation products from column K'$_3$ may be passed to a wiped film evaporator (WFE) to recover adiponitrile in such bottoms. One or more streams comprising catalyst degradation byproducts from column K$_3$ in FIG. 2 may also, optionally, be passed to this wiped film evaporator.

Although particular distillation steps are described above for converting the raffinate stream from the extraction zone into a purified adiponitrile stream, it will be understood that other distillation steps are possible. It is within the ordinary skill in the art to design and operate such steps. Streams of compounds removed from the adiponitrile in the raffinate may be disposed of, further refined, used in a different reaction process or recycled to an appropriate point in the overall reaction system.

Yield of and Purity of Adiponitrile (ADN)

The adiponitrile chemical yield from 1,3-butadiene may be greater than 60%, for example, greater than 85% or greater than 90%, and the adiponitrile chemical yield from hydrogen cyanide may be greater than 60%, for example, greater than 85% or greater than 90%.

By limiting the amount of C$_9$ mononitriles entering into the third reaction zone (Z$_3$), the amount of dinitriles of the formula C$_8$H$_{14}$(C≡N)$_2$, produced in the third reaction zone may be limited. For example, the reaction product from the third (Z$_3$) reaction zone may comprise substantially a dinitrile product comprising adiponitrile (ADN) and having less than 5000 parts per million (ppm); preferably less than 2000 parts per million (ppm); most preferably less 500 parts per million (ppm) dinitriles (DDN) of chemical formula C$_8$H$_{14}$(C≡N)$_2$.

Optional Shared Catalyst Regeneration Zone

The zones described herein where catalyst is partially purified by removal of catalyst degradation products and reaction byproducts are referred to herein as purification zones or regeneration zones. When the phosphorus-containing ligands of the first and second catalysts are identical, the first and second catalyst regeneration zones may be combined (co-mingled) as a shared catalyst regeneration zone comprising liquid-liquid extraction. This option further comprises feeding at least a portion of the first catalyst from the first catalyst purge, feeding at least a portion of the second catalyst from the second catalyst purge or feeding a combination thereof to the shared catalyst regeneration zone to at least partially separate catalyst degradation product and reaction byproduct from a separated catalyst.

At least a portion of the separated catalyst from the shared catalyst regeneration zone may be contacted with 1,3-butadiene and hydrogen cyanide in the first reaction zone (Z$_1$) to produce the first reaction effluent.

At least a portion of the separated catalyst from the shared catalyst regeneration zone may be contacted with 2-methyl-3-butenenitrile in the second (Z$_2$) reaction zone to produce the second reaction effluent.

Catalyst from the shared catalyst regeneration zone may be contacted with both 1,3-butadiene and hydrogen cyanide in the first reaction zone (Z$_1$) and with 2-methyl-3-butenenitrile in the second reaction zone (Z$_2$).

The optional shared catalyst regeneration zone for the first and second catalyst is generally not used when the ligands of the first and second catalysts are different.

The First, Second and Third Catalysts

As used herein, the term "catalyst" includes within its meaning a catalyst precursor composition. This meaning indicates that the zero-valent nickel at some point becomes bound to at least one phosphorus-containing ligand. Furthermore, additional reactions occur during hydrocyanation, e.g., complexing of the initial catalyst composition to an ethylenically unsaturated compound. As used herein, the term "catalyst" also includes within its meaning recycled catalyst, that is, a catalyst comprising a zero-valent nickel and at least one phosphorus-containing ligand which, having been used in the process of the invention, is returned or may be returned to the process and used again or used repeatedly. Suitable solvents for the catalysts include extraction solvents useful in the process, for example, polar solvents such as nitriles, for example, pentenenitriles such as 3-pentenenitrile, and non-polar solvents such as aliphatic hydrocarbons, for example, cyclohexane.

The first, second and third catalysts each comprise zero valent nickel and a phosphorus-containing ligand. These catalysts may be the same or different. Optionally, the first, second and third catalysts are all different. Optionally, the first and second catalysts are the same, and the third catalyst is different. Optionally, the second and third catalysts are the same, and the first catalyst is different. Optionally, the first and second catalysts comprise the same or different monodentate ligand, and the third catalyst comprises a bidentate ligand. Optionally, the first catalyst comprises a monodentate ligand, and the second catalyst and third catalysts comprise the same or different bidentate ligand.

The chemical yield of adiponitrile may be increased from the reaction of 1,3-butadiene and hydrogen cyanide over what can be achieved when the first catalyst, second catalyst, and the third catalyst are the same with respect to the phosphorus-containing ligand and the same catalyst flows into the first, second and third reaction zones.

The first catalyst for reacting BD with HC≡N may comprise, for example, zero-valent Ni and at least one monodentate phosphorus-containing ligand. Also, the third catalyst for reacting 3PN with HC≡N may be segregated from the first ($Z_1$) and second ($Z_2$) reaction zones. Further, the steps for purifying the first and third catalysts are preferably segregated, at least to the extent to avoid a mixture of the first and third catalyst from being introduced into a reaction zone.

The third catalyst may be segregated from the first ($Z_1$) and second ($Z_2$) zones by not recycling the third catalyst back (either directly or indirectly) to the first ($Z_1$) and second ($Z_2$) reaction zones, or indeed to any location upstream of the second ($Z_2$) reaction zone or streams thereto.

When the ligand of the first and second catalysts is a monodentate ligand and the ligand of the third catalyst is a bidentate ligand, the third catalyst may be segregated from the first and second reaction zone. By segregating the third catalyst from the first ($Z_1$) and second ($Z_2$) reaction zones, the concentration of the phosphorus-containing multidentate ligand in the third catalyst in either the first or the second reaction zones may be no more than 100 ppm, for example, no more than 50 ppm, for example, no more than 10 ppm, for example, no more than 5 ppm, for example, no more than 1 ppm, and for example, substantially zero.

Although small amounts (e.g., traces) of the first catalyst may be present in the feed stream 300 to the third reaction zone ($Z_3$), the first catalyst is preferably not intentionally introduced to the third ($Z_3$) reaction zone. Thus, in a preferred embodiment, the purified stream of the first catalyst in line 156 from the distillation column 155 is recycled to at least one of the first reaction zone ($Z_1$) via line 146 and, optionally, to the second reaction zone ($Z_2$) via line 246, but none of this stream in line 156 is passed to the third reaction zone ($Z_3$). In general, at least 90%, for example, at least 95%, for example, at least 99%, for example, at least 99.9% and suitably, substantially all of the first catalyst recycled to at least one of the first reaction zone ($Z_1$) and the second reaction zone ($Z_2$), and/or less than 10%, for example, less than 5%, for example, less than 1%, for example, less than 0.1%, and suitably none of the first catalyst is introduced to the third reaction zone ($Z_3$).

Nevertheless, the present invention does tolerate some of the first catalyst passing downstream to the third reaction zone ($Z_3$), although this is normally achieved by routes other than passing the purified stream of first catalyst in line 156 from the distillation column 155 to the third reaction zone ($Z_3$), as will be appreciated from the process descriptions herein. For example, some of the first catalyst may unintentionally pass into the third reaction zone ($Z_3$) as a result of a unit upset or operator error without the need to shut down the entire integrated process and remove first catalyst from the third reaction zone ($Z_3$).

When the ligand of the first catalyst is a monodentate ligand and the ligand of the third catalyst is a bidentate ligand, the concentration of the phosphorus-containing monodentate ligand of the first catalyst in the third reaction zone ($Z_3$) may be no more than 500 ppm, preferably no more than 100 ppm, preferably no more than 50 ppm, preferably no more than 10 ppm, preferably no more than 5 ppm, preferably no more than 1 ppm, and preferably substantially zero.

The reaction of nickel metal with at least one free phosphorus-containing ligand is taught in U.S. Pat. Nos. 3,903,120, 4,385,007, 4,416,825; United States Patent Application Publication No. 20040176622, and PCT Patent Application Publication No. 1995011077, incorporated herein by reference.

Catalyst compositions comprising at least one phosphorus-containing ligand may be substantially free and maintained separate from at least one of carbon monoxide, oxygen, and water. These catalyst compositions may be preformed or prepared in situ according to techniques well known in the art.

For example, the catalyst composition may be formed by contacting a monodentate or bidentate phosphite ligand with a zero-valent nickel compound having ligands easily displaced by organophosphite ligands, such as $Ni(COD)_2$, $Ni[P(O\text{-}o\text{-}C_6H_4\text{---}CH_3)_3]_3$, and $Ni[P(O\text{-}o\text{-}C_6H_4\text{---}CH_3)_3]_2(C_2H_4)$, all of which are well known in the art, wherein 1,5-cyclooctadiene (COD), tris(ortho-tolyl)phosphite [$P(O\text{-}o\text{-}C_6H_4\text{---}CH_3)_3$], and ethylene ($C_2H_4$) are the easily displaced ligands, where the lower case "o" represents ortho. Elemental nickel, preferably nickel powder, when combined with a halogenated catalyst, as described in U.S. Pat. No. 3,903,120; is also a suitable source of zero-valent nickel.

Alternatively, divalent nickel compounds can be combined with a reducing agent, to serve as a source of zero-valent nickel in the reaction, in the presence of a monodentate or bidentate phosphite ligands. Suitable divalent nickel compounds include compounds of the formula $NiZ_2$ where Z is halide, carboxylate, or acetylacetonate. Suitable reducing agents include metal borohydrides, metal aluminum hydrides, metal alkyls, Li, Na, K, Zn, Fe or $H_2$ and electrochemical means known from the art. See, for example, U.S. Pat. No. 6,893,996, which is incorporated herein by reference. In a catalyst composition, the bidentate phosphite ligand may be present in excess of what can theoretically be coordinated to the nickel at a given time.

When a divalent nickel compound is reacted with a reducing agent, a Lewis acid may be generated as a byproduct. For example, when $NiCl_2$ is reacted with zero valent Zn in the presence of a ligand, there is formed a catalyst comprising zero valent Ni and $ZnCl_2$, which is a Lewis acid. It is possible to use such a reaction product as a feed of both catalyst and Lewis acid to the third reaction zone ($Z_3$). However, this reaction product should be subjected to an appropriate purification step to remove Lewis acid before the catalyst is used as a feed to the first reaction zone ($Z_1$). Such a purification step may involve liquid/liquid extraction and distillation. It is preferred to use zero valent Ni, instead of divalent Ni, as the nickel source for the first catalyst.

Suitable methods for preparing catalysts, which may be used as the first, second or third catalyst, are described in International Application Number PCT/US10/160381, International Application Number PCT/US10/60388, U.S. Publication 2011-0196168 and U.S. Pat. No. 8,969,606.

The catalyst composition may be dissolved in a solvent non-reactive toward, and miscible with, the hydrocyanation reaction mixture. Suitable solvents include, for example, aliphatic and aromatic hydrocarbons with 1 to 10 carbon atoms, and nitrile solvents such as acetonitrile. Alternatively, 3PN, a mixture of isomeric pentenenitriles, a mixture of isomeric methylbutenenitriles, a mixture of isomeric pentenenitriles and isomeric methylbutenenitriles, or the reaction product from a previous reaction campaign, may be used to dissolve the catalyst composition.

As discussed herein above, catalyst may be regenerated by liquid/liquid extraction followed by distillation to remove extraction solvent. The concentration of nickel complexes in the catalyst, recovered in this distillation step, may be increased prior to contacting at least a portion of the concentrated nickel complexes, comprising zero-valent nickel and at least one phosphorus-containing ligand, with 1,3-butadiene and hydrogen cyanide in the first ($Z_1$) reaction zone to produce the first reaction effluent; and with 2-methyl-3-butenenitrile in the second ($Z_2$) reaction zone to produce the second reaction effluent; or their combination. The concentration of nickel complexes may be increased by contacting at least a portion of the extraction solvent-depleted stream with nickel metal in an organonitrile solvent.

Phosphorus-Containing Ligand

The catalysts used in the process of the invention include zero-valent nickel and at least one phosphorus-containing (P-containing) ligand, such as a phosphite, a phosphonite, a phosphinite, a phosphine, and a mixed P-containing ligand or a combination of such members.

The P-containing ligands chemically bond to nickel as complexes comprising zero-valent nickel, and the free P-containing ligands not bonded to the complexes, may be monodentate or multidentate, for example, bidentate or tridentate. The term "bidentate" is well known in the art and means both phosphorus atoms of the ligand may be bonded to a single metal atom. The term "tridentate" means the three phosphorus atoms on the ligand may be bonded to a single metal atom. The terms "bidentate" and "tridentate" are also known in the art as chelate ligands.

As used herein, the term "mixed P-containing ligand" means a P-containing ligand comprising at least one combination selected from the group consisting of a phosphite-phosphonite, a phosphite-phosphinite, a phosphite-phosphine, a phosphonite-phosphinite, a phosphonite-phosphine, and a phosphinite-phosphine or a combination of such members.

At least one of the catalysts selected from the group of the first catalyst, the second catalyst, and the third catalyst may be different with respect to at least one phosphorus-containing ligand.

Suitable phosphorus-containing ligands for the first catalyst are selected from the group consisting of compounds of Formula I, Formula III, Formula IV, Formula IVa or combinations thereof. Suitable phosphorus-containing ligands for the second catalyst, are selected from the group consisting of compounds of Formula I, Formula III, Formula IV, Formula IVa or combinations thereof. Suitable phosphorous-containing ligands for the third catalyst are selected from the group consisting of compounds of Formula I, Formula III, Formula IV, Formula IVa or combinations thereof. Formula III has the structure,

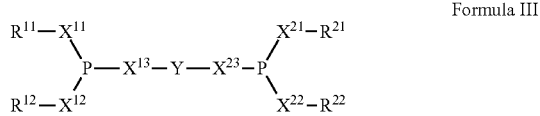

Formula III wherein,
$X^{11}, X^{12}, X^{13}, X^{21}, X^{22}, X^{23}$ independently represent oxygen or a single bond;
$R^{11}, R^{12}$ independently represent identical or different, single or bridged organic radicals;
$R^{21}, R^{22}$ independently represent identical or different, single or bridged organic radicals; and
Y represents a bridging group.

In a preferred embodiment, $X^{11}, X^{12}, X^{13}, X^{21}, X^{22}, X^{23}$ may each be oxygen. In such a case, the bridging group Y is bonded to phosphite groups. In another preferred embodiment, $X^{11}$ and $X^{12}$ may each be oxygen and $X^{13}$ a single bond, or $X^{11}$ and $X^{13}$ each oxygen and $X^{12}$ a single bond, so that the phosphorus atom surrounded by $X^{11}, X^{12}$ and $X^{13}$ is the central atom of a phosphonite. In such a case, $X^{21}, X^{22}$ and $X^{23}$ may each be oxygen, or $X^{21}$ and $X^{22}$ may each be oxygen and $X^{23}$ a single bond, or $X^{21}$ and $X^{23}$ may each be oxygen and $X^{22}$ a single bond, or $X^{22}$ and $X^{23}$ may be oxygen and $X^{21}$ and $X^{22}$ each a single bond, or $X^{21}$ may be oxygen and $X^{22}$ and $X^{23}$ each a single bond, or $X^{21}, X^{22}$ and $X^{23}$ may each be a single bond, so that the phosphorus atom surrounded by $X^{21}, X^{22}$ and $X^{23}$ may be the central atom of a phosphite, phosphonite, phosphinite or phosphine, preferably a phosphonite. In another preferred embodiment, $X^{13}$ may be oxygen and $X^{11}$ and $X^{12}$ each a single bond, or $X^{11}$ may be oxygen and $X^{12}$ and $X^{13}$ each a single bond, so that the phosphorus atom surrounded by $X^{11}, X^{12}$ and $X^{13}$ is the central atom of a phosphonite. In such a case, $X^{21}, X^{22}$ and $X^{23}$ may each be oxygen, or $X^{23}$ may be oxygen and $X^{21}$ and $X^{22}$ each a single bond, or $X^{21}$ may be oxygen and $X^{22}$ and $X^{23}$ each a single bond, or $X^{21}, X^{22}$ and $X^{23}$ may each be a single bond, so that the phosphorus atom surrounded by $X^{21}, X^{22}$ and $X^{23}$ may be the central atom of a phosphite, phosphinite or phosphine, preferably a phosphinite. In another preferred embodiment, $X^{11}, X^{12}$ and $X^{13}$ may each be a single bond, so that the phosphorus atom surrounded by $X^{11}, X^{12}$ and $X^{13}$ is the central atom of a phosphine. In such a case, $X^{21}, X^{22}$ and $X^{23}$ may each be oxygen, or $X^{21}, X^{22}$ and $X^{23}$ may each be a single bond, so that the phosphorus atom surrounded by $X^{21}, X^{22}$ and $X^{23}$ may be the central atom of a phosphite or phosphine, preferably a phosphine. The bridging group Y is preferably an aryl group which is substituted, for example by $C_1$-$C_4$-alkyl, halogen, such as fluorine, chlorine, bromine, halogenated alkyl, such as trifluoromethyl, aryl, such as phenyl, or is unsubstituted, preferably a group having from 6 to 20 carbon atoms in the aromatic system, in particular pyrocatechol, bis(phenol) or bis(naphthol). The $R^{11}$ and $R^{12}$ radicals may each independently be identical or different organic radicals. Advantageous $R^{11}$ and $R^{12}$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups. The $R^{21}$ and $R^{22}$ radicals may each independently be identical or different organic radicals. Advantageous $R^{21}$ and $R^{22}$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups. The $R^{11}$ and $R^{12}$ radicals may each be separate or bridged. The $R^{21}$ and $R^{22}$ radicals may also each be separate or bridged. The $R^{11}, R^{12}, R^{21}$ and $R^{22}$ radicals may each be separate, two may be bridged and two separate, or all four may be bridged, in the manner described.

Formula IV has the structure,

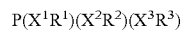

Formula IV wherein,
$X^1, X^2, X^3$ independently represent oxygen or a single bond; and
$R^1, R^2$ and $R^3$ are each independently identical or different organic radicals. $R^1, R^2$ and $R^3$ are each independently alkyl radicals preferably having from 1 to 10 carbon atoms, such as methyl, ethyl, n-propyl, i-propyl, n-butyl, i-butyl, s-butyl, t-butyl, aryl groups such as phenyl, o-tolyl, m-tolyl, p-tolyl, 1-naphthyl, 2-naphthyl, or hydrocarbyl, preferably having from 1 to 20 carbon atoms, such as 1,1'-biphenol, 1,1'-binaphthol. The $R^1, R^2$ and $R^3$ groups may be bonded together directly, i.e. not solely via the central phosphorus atom. Preference is given to the $R^1, R^2$ and $R^3$ groups not being bonded together directly. In a preferred embodiment, $R^1, R^2$ and $R^3$ groups are radicals selected from the group consisting of phenyl, o-tolyl, m-tolyl and p-tolyl. In a particularly preferred embodiment, a maximum of two of the $R^1, R^2$ and $R^3$ groups should be phenyl groups. In another preferred embodiment, a maximum of two of the $R^1$, $R^2$ and $R^3$ groups should be o-tolyl groups. Particularly preferred compounds which may be used are those of the formula (IVa) below:

$$(o\text{-tolyl-O---})_w(m\text{-tolyl-O---})_x(p\text{-tolyl-O---})_y(\text{phenyl-O---})_zP \quad \text{Formula (IVa)}$$

where w, x, y, z are each a natural number and the following conditions apply: w+x+y+z=3 and w, z<=2.

Examples of such compounds (IIa) are (o-tolyl-O—)$_3$P, (p-tolyl-O—)(phenyl-O—)$_2$P, (m-tolyl-O—) (phenyl-O—)$_2$P, (o-tolyl-O—)(phenyl-O—)$_2$P, (p-tolyl-O—)$_2$(phenyl-O—)P, (m-tolyl-O—)$_2$(phenyl-O—)P, (o-tolyl-O—)$_2$(phenyl-O—)P, (m-tolyl-O—)(p-tolyl-O—)(phenyl-O—)P, (o-tolyl-O—)(p-tolyl-O—)(phenyl-O—)P, (o-tolyl-O—)(m-tolyl-O—)(phenyl-O—)P, (p-tolyl-O—)$_3$P, (m-tolyl-O—)(p-tolyl-O—)$_2$P, (o-tolyl-O—)(p-tolyl-O—)$_2$P, (m-tolyl-O—)$_2$(p-tolyl-O—)P, (o-tolyl-O—)$_2$(p-tolyl-O—)P, (o-tolyl-O—)(m-tolyl-O—)(p-tolyl-O—)P, (m-tolyl-O—)$_3$P, (o-tolyl-O—)(m-tolyl-O—)$_2$P, (o-tolyl-O—)$_2$(m-tolyl-O—)P or mixtures of such compounds.

An example of a bidentate phosphite ligand that is useful in the present process is that having the Formula V, shown below

V

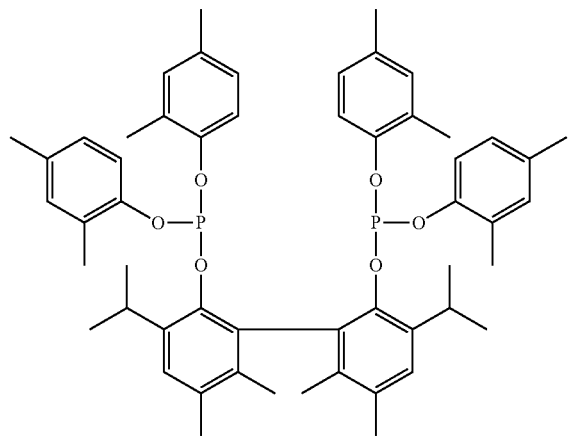

Further examples of bidentate phosphite ligands that are useful in the present process include those having the Formulae VI to IX, shown below wherein for each formula, $R^{17}$ is selected from the group consisting of methyl, ethyl or isopropyl, and $R^{18}$ and $R^{19}$ are independently selected from H or methyl:

VI

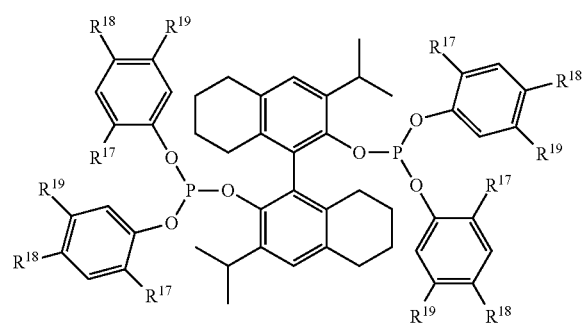

-continued

VII

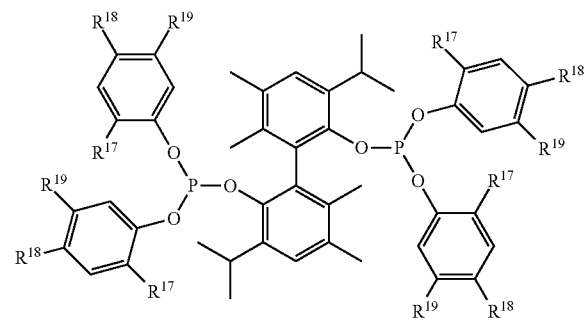

VIII

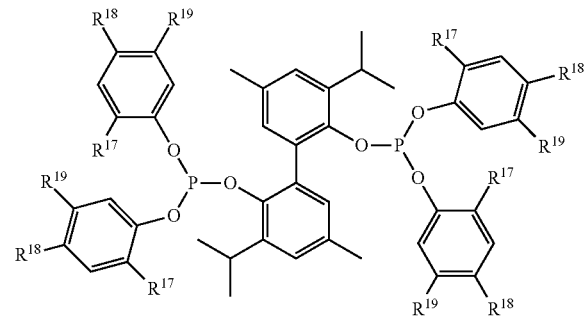

IX

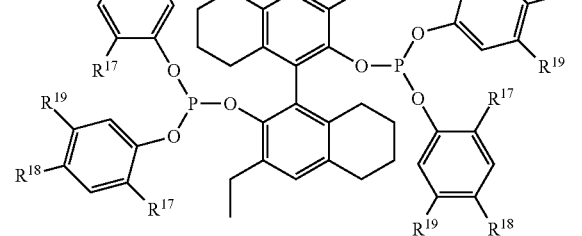

Additional examples of bidentate phosphite ligands that are useful in the present process include a ligand selected from a member of the group represented by Formulae X and XI, in which all like reference characters have the same meaning, except as further explicitly limited:

Formula X

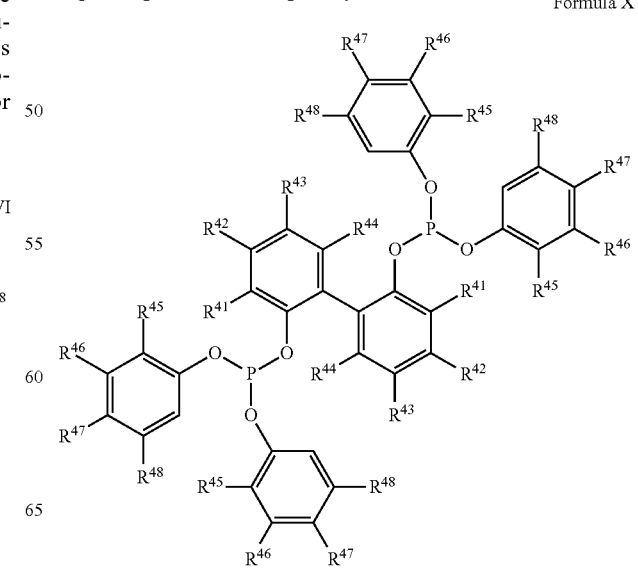

-continued

Formula XI

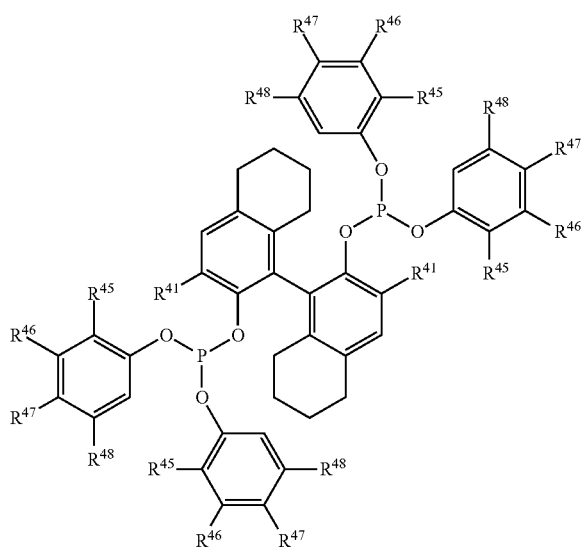

wherein, $R^{41}$ and $R^{45}$ are independently selected from the group consisting of $C_1$ to $C_5$ hydrocarbyl, and each of $R^{42}$, $R^{43}$, $R^{44}$, $R^{46}$, $R^{47}$ and is independently selected from the group consisting of H and $C_1$ to $C_4$ hydrocarbyl.

For example, the bidentate phosphite ligand can be selected from a member of the group represented by Formula X and Formula XI, wherein $R^{41}$ is methyl, ethyl, isopropyl or cyclopentyl;
$R^{42}$ is H or methyl;
$R^{43}$ is H or a $C_1$ to $C_4$ hydrocarbyl;
$R^{44}$ is H or methyl;
$R^{45}$ is methyl, ethyl or isopropyl; and
$R^{46}$, $R^{47}$ and $R^{48}$ are independently selected from the group consisting of H and $C_1$ to $C_4$ hydrocarbyl.

As additional examples, the bidentate phosphite ligand can be selected from a member of the group represented by Formula X, wherein $R^{41}$, $R^{44}$, and $R^{45}$ are methyl;
$R^{42}$, $R^{46}$, $R^{47}$ and $R^{48}$ are H; and
$R^{43}$ is a $C_1$ to $C_4$ hydrocarbyl;

or $R^{41}$ is isopropyl;
$R^{42}$ is H;
$R^{43}$ is a $C_1$ to $C_4$ hydrocarbyl;
$R^{44}$ is H or methyl;
$R^{45}$ is methyl or ethyl;
$R^{46}$ and $R^{48}$ are H or methyl; and
$R^{47}$ is H, methyl or tertiary-butyl;

or the bidentate phosphite ligand can be selected from a member of the group represented by Formula XI, wherein $R^{41}$ is isopropyl or cyclopentyl;
$R^{45}$ is methyl or isopropyl; and
$R^{46}$, $R^{47}$, and $R^{48}$ are H.

As yet another example, the bidentate phosphite ligand can be represented by Formula X, wherein $R^{41}$ is isopropyl; $R^{42}$, $R^{46}$, and $R^{48}$ are H; and $R^{43}$, $R^{44}$, $R^{45}$, and $R^{47}$ are methyl.

It will be recognized that Formulae V to XI are two-dimensional representations of three-dimensional molecules and that rotation about chemical bonds can occur in the molecules to give configurations differing from those shown. For example, rotation about the carbon-carbon bond between the 2- and 2'-positions of the biphenyl, octahydrobinaphthyl, and or binaphthyl bridging groups of Formulae V to XI, respectively, can bring the two phosphorus atoms of each Formula in closer proximity to one another and can allow the phosphite ligand to bind to nickel in a bidentate fashion. The term "bidentate" is well known in the art and means both phosphorus atoms of the ligand are bonded to a single nickel atom.

At least one phosphorus-containing ligand for the first catalyst may be, for example, selected from the group consisting of compounds of Formula IV, wherein Formula IV has the structure above.

At least one phosphorus-containing ligand for the second catalyst may be, for example, selected from the group consisting of compounds of Formulae III and IV, wherein Formulae III and IV have the structure above.

At least one phosphorus-containing ligand for the third catalyst may be selected from the group consisting of compounds of Formula III, wherein Formula III has the structure above.

Lewis Acid Promoter

The reaction, which takes place in the third reaction zone ($Z_3$) for hydrocyanating 3-pentenenitrile to produce adiponitrile, preferably takes place in the presence of a promoter for promoting this reaction. The promoter may be a Lewis acid, such as an inorganic compound, an organometallic compound, or combinations thereof, in which a cation of the Lewis acid is selected from the group consisting of scandium, titanium, vanadium, chromium, manganese, iron, cobalt, copper, zinc, boron, aluminum, yttrium, zirconium, niobium, molybdenum, cadmium, rhenium, lanthanum, erbium, ytterbium, samarium, tantalum, and tin. However, the reactions, which take place in the first reaction zone ($Z_1$) for hydrocyanating,3-butadiene and the second reaction zone ($Z_2$) for isomerizing 2-methyl-3-butenenitrile, preferably take place in the absence or substantial absence of such a promoter. It will be understood that the expression, substantial absence, allows for some measurable promoter to be present, provided that the amount of the promoter is not sufficient to significantly impact the selectivity or yield of the reactions taking place in the first reaction zone ($Z_1$) and the second reaction zone ($Z_2$).

Dinitriles may be produced in the first reaction zone by the reaction of 3PN or 2M3BN with HCN. Lewis acids are capable of promoting the formation of dinitriles in the first reaction zone. Lewis acids are preferably not introduced into the first reaction zone in detectable amounts. However, a detectable amount of a Lewis acid may be introduced into the first reaction zone, provided that dinitrile formation is minimized. For example, a detectable amount of a Lewis acid may be introduced into the first reaction zone, provided that the amount of dinitriles produced, when none of the Lewis acid is introduced into the first reaction zone, is not increased by more than 5 wt %.

Lewis acid may be unintentionally introduced into the first reaction zone as a result of a unit upset or operator error. However, the continuous production of 3-pentenenitrile may be maintained, provided that the ratio of atomic equivalents of Ni to moles of Lewis Acid in the first reaction zone is less than 10:1 during the course of at least 95% of the production of 3-pentenenitrile.

3-pentenenitrile produced in the first and second reaction zones may be reacted with hydrogen cyanide to produce dinitriles comprising adiponitrile in a third reaction zone downstream of the first and second reaction zones. A catalyst and a Lewis acid promoter may flow through the third reaction zone along with reactants and products. Preferably, none of the Lewis acid promoter which flows from the third reaction zone flows into the first reaction zone. However, it is possible that a portion of the Lewis acid promoter which flows from the third reaction zone flows into the first reaction zone, provided that the unwanted production of dinitriles in the first reaction is minimized, as discussed above.

Distillation Equipment

Distillation steps described herein may be performed in any suitable equipment known to one skilled in the art. Examples of conventional equipment suitable for this distillation include sieve tray columns, bubble tray columns, columns with regular packing, random packed columns or single-stage evaporators, such as falling film evaporators, thin-film evaporators, flash distillation evaporators, multiphase helical coil evaporators, natural circulation evaporators or forced circulation flash evaporators. The distillation can be performed in one or more pieces of equipment.

Distillation equipment comprise at least one distillation column. A distillation column may be provided with a structured packing section above the feed location to prevent catalyst entrainment in the distillate and to generate an appropriate separation.

The examples which follow demonstrate the present invention and its capability for use. These examples are regarded as illustrative in nature and not restrictive.

Example 1

Shared Catalyst Recovery System and Bidentate Ligand in Reaction Zones $Z_1$, $Z_2$ and $Z_3$ This Example 1 describes operation of a two-step process for the hydrocyanation of 1,3-butadiene to make adiponitrile using a single, shared catalyst purification system for each of the first reaction zone for hydrocyanating 1,3-butadiene, ($Z_1$), the second reaction zone for isomerizing mixed pentenenitriles to enrich the mixture in 3-pentenenitrile ($Z_2$) and the third reaction zone for hydrocyanating 3-pentenenitrile to adiponitrile ($Z_3$). These Examples use the term "catalyst loop" to include the identified reaction zone ($Z_1$, $Z_2$ or $Z_3$) along with its associated catalyst handling equipment that may include process equipment for separating, purifying and recycling the catalyst, as well as adding fresh make-up catalyst.

1,3-butadiene and hydrogen cyanide are charged to a first reaction zone ($Z_1$), as shown in FIG. 1, where the mixture is contacted in the presence of a first catalyst comprising zerovalent Ni and a phosphite-containing ligand, collectively a catalyst system, to produce a reaction product substantially comprising 3-pentenenitrile (3PN) and 2-methyl-3-butenenitrile (2M3BN). In this Example 1, the catalyst system comprises a bidentate phosphite ligand of Formula III as disclosed herein.

As shown in FIG. 1, 1,3-butadiene reactant is fed into the first reaction zone ($Z_1$) through line 100, hydrogen cyanide reactant is fed into the first reaction zone ($Z_1$) through line 120, and catalyst is fed into the first reaction zone ($Z_1$) through line 140. A reaction product stream is taken from the first reaction zone ($Z_1$) through line 122. The reaction product stream in line 122 comprises products, byproducts, unreacted reactants and catalyst, which flows through the first reaction zone ($Z_1$). The reaction product stream 122 is introduced into a separation section 125, to obtain, inter alia, a concentrated catalyst stream 140 and product stream 200 comprising 2-methyl-3-butenenitrile (2M3BN). The separation section 125 comprises one or more distillation columns as shown in FIG. 4. Unreacted hydrogen cyanide and 1,3-butadiene may also be separated from reaction products and catalyst in separation section 125, although HCN is usually reacted to extinction during normal unit operation. Unreacted 1,3-butadiene is recycled to the first reaction zone ($Z_1$) through lines not shown in FIG. 1. A stream comprising 3-pentenenitrile (3PN) is also withdrawn from separation section 125 through a line not shown in FIG. 1. At least a portion of the catalyst separated from reaction products in separation section 125 is recycled to the first reaction zone ($Z_1$) through line 140.

Subsequent to the reaction in the first reaction zone ($Z_1$), the substantial isomerization of 2M3BN in a second reaction zone ($Z_2$) is conducted in the presence of an isomerization catalyst to produce reaction product comprising substantially 3PN. In this Example 1, the isomerization catalyst is the same catalyst composition introduced into the first reaction zone ($Z_1$).

As shown in FIG. 1, a feed comprising 2M3BN is introduced into the second reaction zone ($Z_2$) through line 200. Catalyst is introduced into the second reaction zone ($Z_2$) through line 240. The effluent stream 222 from the second reaction zone ($Z_2$) comprises catalyst and 3PN product. This effluent stream 222 passes into separation section 225 to obtain, inter alia, a 3PN product stream 300 and a concentrated catalyst stream 240. Separation section 225 comprises a series of distillation columns as shown in FIG. 5.

Catalyst recycle systems are shown in FIG. 1 for supplying catalyst to the first reaction zone ($Z_1$), the second reaction zone ($Z_2$) and the third reaction zone ($Z_3$). In this Example, the catalyst recycle systems are different from those shown in FIG. 1. In particular, all three reaction zones in this Example 1 share a single catalyst purification and regeneration system.

In the catalyst recycle system for supplying catalyst to the first reaction zone ($Z_1$), a portion of the concentrated catalyst stream in line 140 is diverted into catalyst purge stream 126. This catalyst purge stream 126 is mixed with stream 226 and charged, along with stream 400, to extraction zone 370. The regenerated catalyst stream 340 then returns to $Z_1$ and $Z_2$ as streams 140 and 240, respectively.

In this Example 1, the first reaction zone ($Z_1$) and second reaction zone ($Z_2$) are not provided with dedicated, isolated catalyst recovery systems. They share the catalyst recovery system as described above for the third reaction zone ($Z_3$). Catalyst purge streams from the first reaction zone ($Z_1$) and the second reaction zone ($Z_2$) are combined and charged to extraction zone 370 as shown in FIG. 1.

In this Example 1, Lewis acid from the third reaction zone ($Z_3$) carries over to reaction zones $Z_1$ and $Z_2$ with recycled catalyst into the shared liquid-liquid extraction zone 370 and the catalyst purification and recovery steps.

Example 1

Operating Parameters and Results

Nickel dosage is maintained at about 500 ppm weight (based on total feed) in the first reaction zone ($Z_1$). Ligand dosage is controlled at around 3:1 molar ratio of bidentate ligand:nickel.

Catalyst loss is observed when the bottoms (process side of the reboiler) operating temperature in the butadiene column (the first distillation column after the first reaction zone) exceeds about 125° C. While not to limit the scope of the invention by a recitation of theory, it is believed that the loss of the bidentate ligand component of the catalyst is due to thermal degradation. To maintain ligand inventory, the butadiene column bottoms (the first column after the first reaction zone) is controlled at 125° C. Initially, this results in an unacceptably high level of unreacted butadiene in the pentenenitrile-enriched bottoms product. In an attempt to solve this problem, the butadiene column is upgraded for vacuum operation, and refrigeration equipment is installed for condensing the overheads. Additional monitoring equipment is installed to detect oxygen intrusion from the atmosphere and mitigate the risk of uncontrolled 1,3-butadiene polymerization in the presence of oxygen.

The process is carried out under continuous operating conditions, and the residual Lewis acid concentration in the catalyst increases. The physical state of the Lewis acid in the catalyst does not appear to be critical, and may be present in the catalyst in solution or by entrainment. The presence of the Lewis acid appears to correlate with increased conversion of 1,3-butadiene to MGN in the first reaction zone ($Z_1$). This initial conversion of 1,3-butadiene to MGN results in loss of ADN yield.

Example 2

Segregated Catalyst Recovery Systems

This Example 2 illustrates segregated catalyst recovery systems. In particular, this Example 2 illustrates a process using three separate catalyst recovery systems where each of reaction zones $Z_1$, $Z_2$ and $Z_3$ contain catalyst comprising nickel and a bidentate phosphite-containing ligand having the structure of Formula III, above.

In this Example 2, as shown in FIG. 1, 1,3-butadiene reactant is fed into the first reaction zone ($Z_1$) through line 100, hydrogen cyanide reactant is fed into the first reaction zone ($Z_1$) through line 120, and catalyst is fed into the first reaction zone ($Z_1$) through line 140. A reaction product stream is taken from the first reaction zone ($Z_1$) through line 122. The reaction product stream in line 122 comprises products, byproducts, unreacted reactants and catalyst, which flows through the first reaction zone ($Z_1$). The reaction product stream 122 is introduced into a separation section 125, to obtain, inter alia, a concentrated catalyst stream 140 and product stream 200 comprising 2-methyl-3-butenenitrile (2M3BN). The separation section 125 may comprise one or more distillation columns. An example of separation section 125 is shown in FIG. 4. Unreacted hydrogen cyanide and 1,3-butadiene may also be separated from reaction products and catalyst in separation section 125. Unreacted 1,3-butadiene may be recycled to the first reaction zone ($Z_1$) through lines not shown in FIG. 1. A stream comprising 3-pentenenitrile (3PN) may also be withdrawn from separation section 125 through a line not shown in FIG. 1. At least a portion of the catalyst separated from reaction products in separation section 125 may be recycled to the first reaction zone ($Z_1$) through line 140.

Subsequent to the reaction in the first reaction zone ($Z_1$), the substantial isomerization of 2M3BN in a second reaction zone ($Z_2$) is conducted in the presence of an isomerization catalyst to produce a reaction product comprising substantially 3PN. The isomerization catalyst is also referred to herein as the second catalyst. The isomerization catalyst may be the same as the catalyst introduced into the first reaction zone ($Z_1$). Optionally, the isomerization catalyst may be different from the catalyst introduced into the first reaction zone ($Z_1$).

As shown in FIG. 1, a feed comprising 2M3BN is introduced into the second reaction zone ($Z_2$) through line 200. Catalyst is introduced into the second reaction zone ($Z_2$) through line 240. The effluent stream 222 from the second reaction zone ($Z_2$) comprises catalyst and 3PN product. This effluent stream 222 passes into separation section 225 to obtain, inter alia, a 3PN product stream 300 and a concentrated catalyst stream 240. Separation section 225 may comprise one or more distillation apparatus. FIG. 5 shows an example of such a separation section 225.

Catalyst recycle systems are shown in FIG. 1 for supplying catalyst to the first reaction zone ($Z_1$) and the second reaction zone ($Z_2$). These catalyst recycle systems comprise further systems for purifying at least a portion of the catalyst prior to recycle.

In the catalyst recycle system for supplying catalyst to the first reaction zone ($Z_1$), a portion of the concentrated catalyst stream in line 140 is diverted into catalyst purge stream 126.

Catalyst in purge stream 126 is in the form of a solution including impurities, such as reaction byproducts and catalyst degradation byproducts. Catalyst in purge stream 126 is fed to liquid/liquid extraction zone 150 to at least partially purify or regenerate the catalyst. The catalyst is purified or regenerated in that at least some byproducts are removed from the catalyst solution.

A non-polar solvent, such as an alkane, is fed into the liquid/liquid extraction zone 150 through line 130. A polar solvent, which is immiscible with the non-polar solvent, is also fed into the liquid/liquid extraction zone 150 through line 500. In extraction zone 150, there is formed a non-polar phase comprising non-polar solvent and catalyst and a polar phase (e.g., a raffinate) comprising polar solvent and, for example, reaction byproducts and catalyst degradation products. The non-polar phase is taken from extraction zone 150 via line 134 to distillation apparatus 155. The polar phase is taken from extraction zone 150 via line 510 to separation section 1000.

An example of separation section 1000 is described in greater detail in FIG. 2. Separation section 1000 may include, collectively, a series of columns ($K_1$, $K_2$, $K_3$ and $K_4$) which provide for the removal of certain reaction byproducts and certain catalyst degradation products from the polar solvent. The column bottom of $K_4$ provides polar solvent, which is returned to extraction zone 150, via line 500.

Non-polar solvent is distillatively recovered in distillation apparatus 155 and returned to extraction zone 150, via line 130. Extraction zone 150, line 134, distillation apparatus 155 and line 130, collectively, form a recovery loop for recycling non-polar solvent into extraction zone 150. Extraction zone 150, line 510, separation section 1000 and line 500, collectively, form a recovery loop for recycling polar solvent into extraction zone 150. Additional non-polar solvent and polar solvent may be introduced into extraction zone 150 by lines not shown in FIG. 1. This additional solvent may be added for start up and for make-up of solvent lost during the course of the liquid/liquid extraction step.

Column bottoms from distillation column 155 include partially purified catalyst. This catalyst is partially purified or regenerated in the sense that at least some of the catalyst degradation products and/or reaction byproducts have been separated from the solution containing the catalyst. This partially purified catalyst may be taken from distillation column 155 through line 156 and introduced at any point for recycle into the first reaction zone ($Z_1$). In FIG. 1, partially purified catalyst may be taken from distillation column 155 through line 156 and transferred into line 146 for introduction into catalyst recycle line 140 for recycle into the first reaction zone ($Z_1$). FIG. 1 shows the introduction of stream 146 downstream of the take-off stream 126, but this stream may, optionally, be introduced upstream of the take-off stream 126. Stream 146 may also, optionally, be added to any catalyst-containing stream associated with the first reaction zone ($Z_1$).

The partially purified stream of first catalyst, which is subsequently returned to the first reaction zone ($Z_1$) may be provided with additional zero-valent Ni and/or additional phosphorus-containing ligand. In FIG. 1, additional zero-valent Ni and/or additional phosphorus-containing ligand may be provided via line 145. Also as shown in FIG. 1, partially purified stream of first catalyst, which is subsequently fed to the first reaction zone ($Z_1$), may be provided with additional zero-valent Ni and/or phosphorus-containing ligand via line 145. However, it will be understood, that make-up catalyst may be added via different routes, not shown in FIG. 1. For example, make-up catalyst stream 145 may be charged to other sections of the first reaction zone catalyst loop or, for example, directly to the first reaction zone ($Z_1$).

In this Example 2, the second reaction zone ($Z_2$) is provided with a second catalyst recovery system for supplying catalyst to the second reaction zone ($Z_2$). In this second catalyst recycle system, a portion of the concentrated catalyst stream in line 240 is diverted into catalyst purge stream 226. This catalyst purge stream 226 is fed into liquid/liquid extraction zone 250. A non-polar solvent, such as an alkane, is fed into the liquid/liquid extraction zone 250 through line 230. A polar solvent, which is immiscible with the non-polar solvent, is also fed to the liquid/liquid extraction zone 250 through line 700. Dinitriles from sources not shown in FIG. 1 may be added to extraction zone 250, as needed to accomplish desired phase separation and extraction. For example, a portion of the refined dinitrile product stream from the third reaction zone ($Z_3$) may be used. For example, a side stream (not shown) may be taken from line 500 and introduced into extraction zone 250. In extraction zone 250, there is formed a non-polar phase comprising non-polar solvent and catalyst and a polar phase (e.g., a raffinate) comprising, for example, polar solvent, reaction byproducts and certain catalyst degradation products. The non-polar phase is taken from extraction zone 250 via line 234 to distillation apparatus 255. The polar phase is taken from extraction zone 250 via line 710 to separation section 2000. Separation section 2000 is described in greater detail in FIG. 2.

Separation section 2000 includes, collectively, a series of columns ($K_1$, $K_2$, $K_3$ and $K_4$) which provide for the separation of certain reaction by-products and catalyst degradation products. The column bottom of $K_4$ provides polar solvent, which is returned to extraction zone 250, via line 700. Additional polar solvent, in the form of adiponitrile, as needed for phase separation, may be provided from adiponitrile produced in the third reaction zone ($Z_3$) through lines not shown in FIG. 1.

Non-polar solvent is distillatively recovered in distillation apparatus 255 and returned to extraction zone 250, via line 230. Extraction zone 250, line 234, distillation column 255 and line 230, collectively, form a recovery loop for recycling non-polar solvent into extraction zone 250. Extraction zone 250, line 710, separation section 2000 and line 700, collectively, form a recovery loop for recycling polar solvent into extraction zone 250.

Column bottoms from distillation column 255 include partially purified catalyst. This catalyst is partially purified or regenerated in the sense that at least some of the catalyst degradation products and/or reaction byproducts have been separated from the solution containing the catalyst. This partially purified catalyst may be taken from distillation apparatus 255 through line 248 for introduction into catalyst recycle line 240 for recycle into the second reaction zone ($Z_2$). Any partially purified stream of catalyst, which is subsequently fed to the second reaction zone ($Z_2$), may be provided with additional zero-valent Ni and/or phosphorus-containing ligand, for example, via line 245. Although not shown in FIG. 1, line 245 may optionally be fed directly into line 246 or line 248 instead of line 240. Other ways of introducing make-up catalyst are known in the art and may be used.

The 3PN product in line 300 is introduced into the third reaction zone ($Z_3$), where 3PN is reacted with HCN. 3PN from separation section 125 may also be introduced into the third reaction zone ($Z_3$) through a line or lines not shown in FIG. 1. The HCN reactant feed is introduced into the third reaction zone ($Z_3$) through line 220. The third catalyst comprising, optionally, zero-valent Ni and a bidentate phosphite-containing ligand, collectively a third catalyst system, and a Lewis acid promoter is introduced into the third reaction zone ($Z_3$) through line 340. The reaction of 3PN and HCN in the third reaction zone ($Z_3$) produces a reaction product containing adiponitrile. A reaction product stream is taken from the third reaction zone ($Z_3$) by line 400. The reaction product stream comprises, for example, adiponitrile, catalyst, promoter, and unreacted reactants. The reaction product stream may optionally be passed through a separation section (not shown in FIG. 1) to remove unreacted reactants, prior to separation of catalyst from adiponitrile product.

Catalyst and adiponitrile product from the product stream in line 400 are passed into liquid/liquid extraction zone 370. A non-polar solvent, such as an alkane, is fed into the liquid/liquid extraction zone 370 through line 330. The non-polar solvent introduced into the liquid/liquid extraction zone 370 may have the same or different composition as the non-polar solvent introduced into the liquid/liquid extraction zone 150. Together, non-polar solvent from line 330 and adiponitrile product from line 400 comprise an extractant system of immiscible components. In extraction zone 370, there is formed a non-polar phase comprising non-polar solvent and catalyst and a polar phase (e.g., a raffinate) comprising adiponitrile, promoter and catalyst degradation products.

The non-polar phase is taken from extraction zone 370 via line 334 to distillation apparatus 375. The polar phase comprising adiponitrile is taken from extraction zone 370 via line 600 to adiponitrile purification section 3000. Adiponitrile purification section 3000 is described in greater detail in FIG. 3.

Adiponitrile purification section 3000 may include, collectively, a series of columns ($K'_1$, $K'_2$, $K'_3$ and $K'_4$) which provide for the separation of impurities, such as reaction byproducts and catalyst degradation products. The column bottom of $K'_4$ provides the purified adiponitrile product, which is recovered in line 660. A portion of the purified adiponitrile product may optionally be returned to extraction zone 150 or extraction zone 250 (by lines not shown in FIG. 1) to facilitate phase separation in these extraction zones.

Non-polar solvent is distillatively recovered in distillation apparatus 375 and returned to extraction zone 370, via line 330. Extraction zone 370, line 334, distillation apparatus 375 and line 330, collectively, form a recovery loop for recycling non-polar solvent into extraction zone 370. Column bottoms from distillation column 375 include partially purified catalyst. This partially purified catalyst may be taken from distillation column 375 through line 340 for recycle of catalyst into the third reaction zone ($Z_3$). The partially purified stream of third catalyst in line 340, which is subsequently returned to the third reaction zone ($Z_3$), may be provided with make-up quantities of additional zero-valent Ni and/or third phosphorus-containing ligand along with promoter. In FIG. 1, make-up quantities of additional zero-valent Ni and/or third phosphorus-containing ligand and/or promoter may be added via line 345. However, it will be appreciated that there are other ways of introducing make-up catalyst and promoter. For example, all or a portion of the recycled catalyst stream 340 may be charged to a catalyst reactor to increase its nickel content and the effluent from the catalyst reactor may introduced at a suitable point.

FIG. 2 shows a distillation train, which may be used as separation section 1000 or separation section 2000, shown in FIG. 1. In FIG. 2, line 515 represents either line 510 or line 710 of FIG. 1. Line 515 transports a raffinate stream from either extraction zone 150 or extraction zone 250 into separation section 1000 or separation section 2000, as shown in FIG. 1. The raffinate stream in line 515 is first passed into distillation column $K_1$, where extraction solvent is separated from higher boiling components of the raffinate stream. In particular, extraction solvent, such as cyclohexane, is withdrawn from distillation column $K_1$ through line 525, and higher boiling components of the raffinate stream are withdrawn from distillation column $K_1$ through line 520.

The solvent-depleted stream in line 520 is then passed into distillation column $K_2$, where pentenenitrile is separated from higher boiling components remaining in the raffinate stream. In particular, pentenenitrile, such as 3PN and 2M3BN, is withdrawn from distillation column $K_2$ through line 550, and higher boiling components of the raffinate stream are withdrawn from distillation column $K_2$ through line 530.

The pentenenitrile-depleted stream in line 530 is then passed into distillation column $K_3$, where dinitriles are separated from higher boiling components remaining in the raffinate stream. In particular, dinitriles, such as ADN and MGN, are withdrawn from distillation column $K_3$ through line 535, and higher boiling components of the raffinate stream are withdrawn from distillation column $K_3$ through line 540. These higher boiling components in line 540 may comprise, for example, catalyst degradation products.

The dinitrile-enriched stream in line 535 is then passed into distillation column $K_4$, where adiponitrile is separated from lower boiling dinitriles, such as MGN. In particular, MGN is withdrawn from distillation column $K_4$ through line 420. The MGN-containing stream in line 420 also includes $C_8H_{13}C\equiv N$ compounds and phenolic compounds. An adiponitrile-enriched stream is withdrawn from distillation column $K_4$ through line 560. In FIG. 2, line 560 represents either line 500 or line 700 of FIG. 1. As shown in FIG. 1, the adiponitrile-enriched stream in line 500 is recycled to the liquid/liquid extraction zone 150, and the adiponitrile-enriched stream in line 700 is recycled to the liquid/liquid extraction zone 250.

FIG. 3 shows a distillation train, which may be used as adiponitrile purification section 3000, shown in FIG. 1. Line 600 transports a raffinate stream from extraction zone 370 into distillation column $K'_1$, where extraction solvent is separated from higher boiling components of the raffinate stream. In particular, extraction solvent, such as cyclohexane, is withdrawn from distillation column $K'_1$ through line 625, and higher boiling components of the raffinate stream are withdrawn from distillation column $K'_1$ through line 620.

The solvent-depleted stream in line 620 is then passed into distillation column $K'_2$, where pentenenitrile is separated from higher boiling components remaining in the raffinate stream. In particular, pentenenitrile, such as 3PN and 2M3BN, is withdrawn from distillation column $K'_2$ through line 650, and higher boiling components of the raffinate stream are withdrawn from distillation column $K'_2$ through line 630.

The pentenenitrile-depleted stream in line 630 is then passed into distillation column $K'_3$, where dinitriles are separated from higher boiling components remaining in the raffinate stream. In particular, dinitriles, such as ADN and MGN, are withdrawn from distillation column $K'_3$ through line 635, and higher boiling components of the raffinate stream are withdrawn from distillation column $K'_4$ through line 640. These higher boiling components in line 640 may comprise, for example, catalyst degradation products.

The dinitrile-enriched stream in line 635 is then passed into distillation column $K'_4$, where adiponitrile is separated from lower boiling dinitriles, such as MGN. In particular, an MGN-enriched stream is withdrawn from distillation column $K'_4$ through line 670, and a purified adiponitrile stream is withdrawn from distillation column $K'_4$ through line 660.

FIG. 4 is a schematic representation of an example of a distillation train, which may be used as separation section 125, shown in FIG. 1. Stream 122 comprising 3PN, 2M3BN, at least one catalyst, and BD is transferred into an apparatus 810 for distillation. In this apparatus, stream 122 is distilled to obtain a BD-enriched stream 812 and a BD-depleted stream 813 comprising 3PN, 2M3BN, and at least one catalyst. The BD-enriched stream 812 may be recycled the first reaction zone ($Z_1$).

The BD-depleted stream 813, which comprises 3PN, 2M3BN, and at least one catalyst is then transferred to another apparatus 820 for further distillation. In this apparatus, stream 813 is distilled to obtain a top product stream 824 enriched in BD, a stream 825, comprising 3PN and 2M3BN, and a bottom product stream 140 enriched in at least one catalyst. Stream 824 enriched in BD may also be recycled to the first reaction zone ($Z_1$). If excess dinitriles are present in, for example, apparatus 810 or 820, the catalyst may be less thermally stable, causing nickel to plate out on high-temperature surfaces such as exchanger tubes and reboiler walls. Alternatively, this may trigger precipitation of nickel solids, for example, in the column bottoms. The presence of excess dinitriles may also limit the maximum operating temperature and require closer process control, especially temperature control.

Stream 825, comprising 3PN and 2M3BN, is transferred at least in part to another distillation apparatus 830. In this apparatus, the distillation of stream 825 is distilled to obtain 2M3BN-enriched stream 200 and 2M3BN-depleted stream 838 comprising 3PN. Stream 200 may be obtained at the top region of the distillation apparatus, while the stream 838 may be obtained at the bottom region of the distillation apparatus.

FIG. 4 illustrates one distillation system for distilling the effluent from the first reaction zone ($Z_1$). However, it will be understood that it is within the skill in the art to design and operate other distillation systems to achieve the same or essentially the same results. For example, depending upon the thermal stability of catalyst, it may be possible to combine distillation apparatus 810 and distillation apparatus 820 into a single distillation apparatus, where a BN-enriched stream is withdraw as a top draw, a PN-enriched stream is withdrawn as a side draw, and a catalyst-enriched stream is withdrawn as a bottom draw.

FIG. 5 is a schematic representation of an example of a distillation train, which may be used as separation section 225, shown in FIG. 1. The isomerization reaction effluent in stream 222 obtained in the second reaction zone is distilled to recover catalyst and products. Stream 222 is introduced into distillation apparatus 940. A pentenenitrile-enriched stream 942, comprising 3PN, 2M3BN, and (Z)-2M2BN, may be obtained from the distillation apparatus 940. Stream 942 may also comprise other pentenenitriles, selected from 4PN, (E)-2M2BN, or a combination thereof, and optionally dimerized BD compounds having the empirical formula $C_8H_{12}$, such as VCH and ethylidene cyclohexene isomers. A pentenenitrile-depleted stream 240, enriched in at least one catalyst, may be obtained as the bottom product.

Stream 942 may be distilled to purge at least a portion of the lower-boiling (Z)-2M2BN isomer from the 3PN and 2M3BN reaction product mixture.

Stream 942, comprising 3PN, 2M3BN, and (Z)-2M2BN, is distilled in distillation apparatus 950. Stream 954 is obtained as an overhead product that is enriched in (Z)-2M2BN. Stream 955, comprising 3PN and 2M3BN, is obtained as a bottom product and is depleted in (Z)-2M2BN. "Enriched" and "depleted" in (Z)-2M2BN are relative to its concentration in stream 942.

Stream 954 may also comprise other pentenenitriles, selected from the group comprising 2M3BN, (E)-2M2BN, and optionally dimerized BD compounds having the empirical formula $C_8H_{12}$, such as VCH and ethylidene cyclohexene isomers. Stream 955 may also comprise other pentenenitriles, selected from the group comprising 4PN, 2PN, and (E)-2M2BN.

The distillation is optionally operated in such a manner to cause dimerized BD compounds to be enriched in stream 954 and depleted in stream 955, both relative to the concentration of dimerized BD compounds in stream 942. Optionally, dimerized BD compounds are enriched in stream 954 through an azeotrope of said compounds with 2M3BN. As a result of the operations described above, stream 954 comprises greater than 1% by weight, for example greater than 5% by weight, for example greater than 10% by weight of 2M3BN, relative to the total mass of stream 954.

Stream 955, comprising 3PN and 2M3BN, may be transferred at least in part to distillation apparatus 960. In this apparatus, the distillation of stream 955 occurs to obtain 2M3BN-enriched stream 967 and a 2M3BN-depleted stream 300 comprising 3PN. Stream 967 may be obtained at the top region of the distillation apparatus, while the stream 300 may be obtained at the bottom region of the distillation apparatus.

FIG. 5 illustrates one distillation system for distilling the effluent from the second reaction zone ($Z_2$). However, it will be understood that it is within the skill in the art to design and operate other distillation systems to achieve the same or essentially the same results. For example, a distillation step to remove low boilers may be inserted into the system, as described above. It is also possible to share equipment used for distilling the effluent from the first reaction zone. For example, a stream comprising 3PN and 2M3BN obtained by distilling the effluent from the second reaction zone ($Z_2$) may be passed to a distillation apparatus, such as distillation apparatus 830, used in the distillation of the effluent form the from the first reaction zone ($Z_1$), to obtain a 3PN-enriched stream and a 2M3BN-enriched stream.

Comparison of Example 1 and Example 2

Lewis Acid in the Catalyst of the First ($Z_1$) and Second ($Z_2$) Reaction Zones The residual Lewis acid concentration in the catalyst of the first ($Z_1$) and second ($Z_2$) zones increases in Example 1. The physical state of the Lewis acid in the catalyst does not appear to be critical, and may be present in the catalyst in solution or by entrainment. The presence of the Lewis acid is observed to correlate with increased conversion of 1,3-butadiene to MGN in the first reaction zone ($Z_1$). This initial conversion of 1,3-butadiene to MGN results in loss of ADN yield.

Example 3

Segregated Catalyst Recovery Systems

Example 3 illustrates partially segregated catalyst recovery systems with monodentate ligand in the $Z_1/Z_2$ catalyst loops and bidentate ligand in the $Z_3$ catalyst loop where the $Z_1$ and $Z_2$ catalyst loops share a first catalyst recovery section and the $Z_3$ catalyst loop has a dedicated second catalyst recovery system. In this Example 3, the $Z_1/Z_2$ catalyst recovery section and the $Z_3$ catalyst recovery section are segregated to minimize flow of the monodentate ligand of $Z_1/Z_2$ into the bidentate ligand of $Z_3$, and the bidentate ligand and Lewis acid of $Z_3$ into the monodentate ligand of $Z_1/Z_2$.

For this Example 3, Example 2 is repeated, except that the first reaction zone ($Z_1$) and the second reaction zone ($Z_2$) share a single catalyst recovery system, not shown in FIG. 1. A shared catalyst recovery system may be desirable when the first and second phosphite-containing ligands are the same, as is the case in this Example 3, where both $Z_1$ and $Z_2$ use a catalyst comprising a monodentate phosphite ligand. In such a shared system, the following features may be eliminated or shut down: lines 226, 230, 234, 247, 248, 700, and 710; extraction zone 250; distillation apparatus 255; and separation section 2000. Instead of taking a purge stream via line 226, a purge stream may be taken via line 227 and introduced into line 126 or directly into extraction zone 150. In such a shared catalyst recovery system, any partially purified catalyst stream entering the second reaction zone ($Z_2$) would pass through lines 246 and 240 according to the configuration shown in FIG. 1.

Comparison of Example 2 and Example 3

In comparison with Example 2, the substitution of the monodentate ligand coupled with isolating the $Z_1/Z_2$ catalyst recovery section from the $Z_3$ catalyst recovery section lowers the production of $C_9$ mononitriles from the first reaction zone ($Z_1$) by about 0.3% per pass, based on 1,3-butadiene feed. These $C_9$ mononitriles readily convert to $C_{10}$ dinitriles (also referred to as decenedinitriles or DDNs) in the third reaction zone ($Z_3$), degrade the quality of the as-produced ADN and result in ADN yield loss from 1,3-butadiene.

Example 3 also lowers the formation of VCH (vincylcyclohexane) in the first reaction zone ($Z_1$) by about 0.5% per pass in comparison with Example 2. This is desirable because converting 1,3-butadiene to VCH (rather than to 3-pentenenitrile and then further to adiponitrile) represents a yield loss of ADN.

Example 3 lowers production of undesired byproducts from the first reaction zone ($Z_1$), especially including 2-pentenenitrile, by about 1.0%. This is significant because 2-pentenenitriles in the reaction zone ($Z_1$) outlet carry through both the second isomerization reaction zone ($Z_2$) without substantially reacting to 3-pentenenitriles, and then carry through the third hydrocyanation zone ($Z_3$) without substantially reacting to form ADN. Thus 1,3-butadiene converted to 2-pentenenitrile is a yield loss with respect to ADN.

Using a monodentate phosphite ligand (rather than a bidentate phosphite ligand) in the first and second reaction zones ($Z_1$ and $Z_2$) allows the maximum temperatures in distillation apparatus 810 to be increased. This eliminates the need for vacuum operation, thus improving safety and reliability of the butadiene recovery steps.

Example 4 Through 7

Removing TBC

The following Examples 4 through 7 illustrate methods for removing TBC from 1,3-butadiene. Removing TBC from the 1,3-butadiene feed to the first reaction zone ($Z_1$) reduces formation of undesired byproducts generated by the reaction of TBC with the phosphite ligand present in $Z_1$.

Example 4

In Example 4, three commercial 1,3-butadiene feeds are separately and sequentially charged to the first reaction zone ($Z_1$). The three commercial 1,3-butadiene feeds contain 50, 100 and 500 ppm of TBC (tert-butylcatechol). For comparison, the feed containing 50 ppm TBC is contacted with a suitable sorbent such as activated carbon or activated alumina to extract the essentially all the TBC from the 1,3-butadiene feed, thus providing the feed for Comparative Example 4, containing less than about 1 ppm (weight) of TBC. Any suitable sorbent may be used in this Example 4, as is known to those of ordinary skill in the art.

|  | TBC content, ppm (weight) based on 1,3-butadiene feed | Process configuration of Example 2 - Bidentate Ligand in First Reaction Zone ($Z_1$) - Weight percent of $Z_1/Z_2$ catalyst inventory lost to TBC reaction products per unit time. | Process configuration of Example 3 - Monodentate Ligand in First Reaction Zone ($Z_1$) - Weight percent of $Z_1/Z_2$ catalyst inventory lost to TBC reaction products per unit time. |
|---|---|---|---|
| Comparative Example 4 | <1 | 0 | 0 |
| Example 4a | 50 | 10 | 1 |
| Example 4b | 100 | 20 | 2 |
| Example 4c | 500 | 100 | 10 |

Example 5

Flashing 1,3-butadiene to Remove TBC

Example 5 illustrates a first of two methods for removal of TBC from 1,3-butadiene feed.

1,3-butadiene is charged to a flash drum at near-atmospheric pressure. Heat input to the flash drum is approximately 417.8 kJ/kg of 1,3-butadiene feed. TBC is drawn off as a bottoms product. The 1,3-butadiene is then cooled and condensed before flowing the purified 1,3-butadiene to the first reaction zone ($Z_1$).

Example 6

Caustic Wash to Remove TBC 1,3-butadiene is flashed and charged to a lower inlet of a countercurrent gas-liquid contactor while an aqueous NaOH solution is charged to the top of the contactor through a liquid distributor. The purified, wet 1,3-butadiene overhead stream is then charged to a mutli-bed molecular sieve dryer piped and valved in parallel to allow selective sorption and regeneration. Dry nitrogen or dry flare gas is back-charged through the molecular sieve beds for regeneration. The dried, caustic-washed 1,3-butadiene contains less than about 5 ppm TBC.

Example 7

Direct Sorption to Remove TBC

Liquid 1,3-butadiene is charged to a first of two sorption beds containing an activated carbon sorbent as taught in U.S. Pat. No. 4,547,619 to Diaz. As described for the molecular sieve dryer of Example 6, the activated carbon sorption beds are piped and valved in parallel to allow selective sorption and regeneration. As needed, the sorbent beds are selectively regenerated by heating or by passing a heated non-oxidizing gas, such as nitrogen or superheated steam, through the sorption bed. The flow of commercially delivered 1,3-butadiene through the sorbent bed is controlled to provide a purified 1,3-butadiene intermediate product stream containing less than about 5 ppm TBC.

Example 8

Production of Vinylcyclohexane (VCH)—Normal Unit Operation

Examples 2 and 3 are repeated and VCH formation is monitored. VCH is an undesired byproduct of the first reaction zone ($Z_1$). VCH is a cyclic dimerization product formed by 1,3-butadiene and thus represents a yield loss of adiponitrile. During normal continuous operation, the VCH content of the crude reaction product of the first reaction zone ($Z_1$) of Example 2 is measured and compared with the VCH content of the crude reaction product of the first reaction zone ($Z_1$) of Example 3. VCH formation in the Example 2 crude pentenenitrile product stream is about 1% higher than that of Example 3.

Example 9

Production of Vinylcyclohexane (VCH)—Startup and Shutdown Unit Operation

Example 8 is repeated during unit startup and unit shutdown. During unit startup and shutdown, 1,3-butadiene recycle is increased, due in part to lower per-pass conversions and also by design to stabilize unit operations. VCH production increases as a function of contact time between the catalyst of the first reaction zone and the 1,3-butadiene, with VCH formation in the Example 3 (monodentate ligand in and $Z_2$, bidentate ligand in $Z_3$) process configuration consistently being lower than that of the Example 2 configuration (bidentate ligand in all of $Z_1$, $Z_2$ and $Z_3$ reaction zones).

Example 10

Removal of $C_9$ Mononitriles

This Example 10 illustrates the building up of $C_9$ mononitriles in an integrated catalyst recovery/regeneration loop. Example 1 is repeated and the concentration of $C_9$ mononitriles is measured at the outlet of the first reaction zone ($Z_1$). Concentrations vary during the run, ranging from about 1000 ppm to about 10,000 ppm based on total reaction zone effluent. Using the integrated catalyst purification system of Example 1, the $C_9$ mononitriles accumulate in the catalyst loop. As the concentration of $C_9$ mononitriles builds in the catalyst loop, these $C_9$ mononitriles are at least partially transferred into the 3-pentenenitrile-enriched feed to the third reaction zone ($Z_3$), where they readily convert to DDNs and degrade the quality of the crude as-produced dinitrile product.

Example 11

Removal of $C_9$ Mononitriles with Segregated Catalyst Recovery Systems

Example 3 is repeated.

Stream 126 has a higher concentration of (is enriched in) $C_9$ mononitriles relative to the effluent from the first reaction zone ($Z_1$). These $C_9$ mononitriles proportion between the raffinate and extract phases in the liquid/liquid extraction system. The raffinate is charged through line 510 and 515 to the first column $K_1$ of separation section 1000. The $C_9$ mononitriles concentrate in the $K_1$ bottoms stream 520 where they are charged to column $K_2$. Column $K_2$ is operated such a majority of the $C_9$ mononitriles leave the column in the bottoms stream 530, where they flow to column $K_3$ and exit via 535, then via 420 from column $K_4$.

Example 12

Removal of C9 Mononitriles with MGN

Example 3 is repeated.

This Example 12 illustrates that the removal of MGN, C9 mononitriles, phenol and cresols from the reaction system, ultimately through the distillation train used to treat the raffinate stream from the extractor, may be facilitated by distilling the reaction product stream from the first reaction zone ($Z_1$) in a particular manner. For example, after removing unreacted 1,3-butadiene and hydrogen cyanide from the reaction product stream 122 via distillation apparatus 810 as shown in FIG. 4, distillation apparatus 820 receives the bottoms stream (substantially free of 1,3-butadiene in this Example 12) from distillation apparatus 810 and is controlled to concentrate $C_9$ mononitriles in the bottoms stream 140. Distillation apparatus 820 is controlled by selecting the number of stages in the rectification section and the reflux ratio to concentrate $C_9$ mononitriles in the bottoms stream 140. The distillation apparatus 820 is operated in a manner such that the catalyst-enriched stream comprises at least 5% by weight of pentenenitrile including the sum of 3-pentenenitrile and 2-methyl-3-butenenitrile. In this way, MGN, $C_9$ mononitriles, phenol and cresols tend to pass into the catalyst-enriched stream.

These compounds may then be removed from bottoms stream 140, and accordingly, at least in part from the reaction system, by a liquid/liquid extraction process, as described above.

The process conditions in distillation apparatus 820 can be adjusted to increase the relative concentration of pentenenitriles in the bottoms stream 140, thus decreasing the relative concentration of $C_9$ mononitriles in the overhead stream 824. This tends to improve removal of $C_9$ mononitriles from the system.

About 90% by weight of the $C_9$ mononitriles present in the raffinate from the catalyst recovery system associated with the first reaction zone ($Z_1$) are removed in the overhead stream of column $K_4$. Conditions in distillation apparatus 820 are adjusted to provide $C_9$ mononitrile concentration in the charge to the third reaction zone ($Z_3$) of less than 1500 ppm, for example less than 1000, less than 500 ppm, or less than 100 ppm depending upon the purity requirements for the as-produced dinitrile effluent from the third reaction zone ($Z_3$).

Example 13

Enhanced Removal of $C_9$ Mononitriles—Chimney Tray Side Draw Column

Example 12 is repeated.

This Example 13 illustrates enhanced removal of $C_9$ mononitriles using a particular tray and pumparound configuration for the bottom tray of distillation apparatus 820 of FIG. 4, included in separation section 125 in FIG. 1.

One of the problems attendant to recycling catalyst to the first reaction zone ($Z_1$) is that dinitriles formed in the first reaction zone ($Z_1$) tend to build up in the catalyst recycle loop. This problem is at least partially mitigated by installing a chimney tray in the pentenenitrile separation column, referred to here as distillation apparatus 820.

For this Example 13, distillation apparatus 820 in FIG. 4 is fitted with a chimney tray.

This distillation apparatus 820 in FIG. 4 is illustrated with a chimney tray as distillation apparatus 850 in FIG. 6.

The chimney tray 870 is located at a point just above the feed inlet 852. Liquid accumulates on the chimney tray and is drawn off via line 872 and pump 874, charged via line 876 to trim heater 880 with capacity sufficient to vaporize at least part of the feed to the trim heater. The heated stream 882 is then returned to the chimney tray 870 or at a point along the distillation apparatus 850 just above the chimney tray 870, A catalyst-enriched liquid accumulates in the bottom section of distillation apparatus 850, and is heated by a reboiler 866. Above the chimney tray 870, the pentenenitrile separation column may contain one or more stages of separation in the form of trays or packing 854. The overhead stream 856 may be partially condensed and the liquid refluxed to the top of the distillation apparatus 850.

The side draw stream 878 downstream from pump 874 is enriched in $C_9$ mononitriles and dinitriles. This process configuration of Example 13 reduces the $C_9$ mononitrile and dinitrile content of the recycled catalyst stream to the first reaction zone ($Z_1$) and provides a stream concentrated in $C_9$ mononitriles and dinitriles for more effectively removing these components from the process upstream of the third reaction zone ($Z_3$). By operating this chimney tray side draw configuration of Example 13, flow of $C_9$ mononitriles and dinitriles to the third reaction zone ($Z_3$) is reduced.

Example 14

Comparison of $C_9$ Mononitrile Formation in Examples 2 and 3

Examples 2 and 3 are repeated, and the total production of $C_9$ mononitriles from the first reaction zone ($Z_1$) is measured.

In Example 3, the catalyst comprising the monodentate ligand produces a mixed pentenenitrile product from the first reaction zone ($Z_1$) containing about 500 ppm of $C_9$ mononitriles. In Example 2, the catalyst comprising the bidentate ligand produces a mixed pentenenitrile product from the first reaction zone ($Z_1$) containing from about 1000 to 10000 or more ppm of $C_9$ mononitriles.

Example 15

Dedicated 3-pentenenitrile Distillation

This Example 15 illustrates another option to reduce the concentration of $C_9$ mononitriles in the feed to the third reaction zone ($Z_3$).

One method to reduce the content of $C_9$ mononitriles in the 3-pentenenitrile feed to the third reaction zone ($Z_3$) is to modify the operation of Example 2 by distilling the 3-pentenenitrile feed stream to provide an overhead stream enriched in 3-pentenenitrile and a bottoms stream enriched in $C_9$ mononitriles.

The 3-pentenenitrile product from the first reaction zone ($Z_1$), and optionally isomerized pentenenitrile effluent ("isomerate") from the second reaction zone ($Z_2$), is charged to a multistage distillation column equipped with an overhead condenser and return piping with one or more control valves for adjusting column pressure and reflux ratio. The multistage distillation column also includes one or more reboilers and optional interstage heaters below the feed point for vaporizing liquid in the column. The column operation is controlled to provide an overhead stream enriched in 3-pentenenitrile and a bottom stream enriched in $C_9$ mononitriles and dinitriles including MGN. Energy input to this column for flashing, cooling and condensing essentially all of the 3-pentenenitrile effluent from the second reaction zone ($Z_2$) significantly increases the total energy consumption per unit time of the ADN process in comparison to Examples 2 and 3 operated without this additional distillation step.

Example 16

Enhanced Removal of Intermediate Boilers

In this Example 16, Example 13 is repeated.

Example 16 illustrates enhanced removal of intermediate boilers, such as MGN, $C_8H_{13}C{\equiv}N$ compounds, phenol and cresols from the reaction system, ultimately through the distillation and liquid/liquid separation sections by selectively treating stream 878 withdrawn from distillation apparatus 850 as shown in FIG. 6.

These compounds may then be removed at least in part from the reaction system by the extraction process into the raffinate and from the raffinate by the raffinate treatment process described above. The stream from the side draw 878 may then be passed either directly or indirectly (e.g., into the catalyst purge stream) to the extraction section. In this way, there is achieved an increased amount of MGN, $C_8H_{13}C{\equiv}N$ compounds, phenol and cresols passed into the extraction section and separated from recycled catalyst. Optionally, stream 878 can be fed to a multistage extraction section after the first stage of the multistage extraction section to further improve $C_9$ mononitrile rejection.

Example 17

TBC Byproducts

This Example 17 illustrates the behavior of tertiary-butylcatechol (TBC) in the disclosed process.

Tertiary-butylcatechol (TBC) is a polymerization inhibitor, which inhibits the polymerization of 1,3-butadiene, particularly while the 1,3-butadiene is in storage. Commercial sources of 1,3-butadiene often include small amounts of TBC to inhibit polymerization of 1,3-butadiene.

TBC reacts with monodentate phosphite ligands and bidentate phosphite ligands.

TBC in the 1,3-butadiene feed triggers a number of problems. TBC reacts with ligand in the first reaction zone ($Z_1$) to form TBC byproducts which complex with nickel and TBC byproducts which react with catalyst ligands. These nickel-containing complexes appear to be less catalytically active than the nickel-ligand complex of the first catalyst. Reactive TBC byproducts of the TBC reaction in the first reaction zone ($Z_1$) further include compounds, such as phenol and cresols, which may further react with catalyst ligand in the third reaction zone ($Z_3$). The reaction of these reactive TBC byproducts with catalyst ligand in the third reaction zone ($Z_3$) causes similar problems in that new nickel-containing complexes are generated. These newly generated nickel-containing complexes are less catalytically active than the nickel-ligand complex of the third catalyst. As described below, a portion of the reactive TBC byproducts is rejected into the raffinate phase of a liquid/liquid extraction section and removed from the process.

Examples 2 and 3 are repeated. The reactive TBC byproducts (e.g., phenol and cresols) described above are withdrawn from the $K_4$ column of FIG. 2 as overheads. This withdrawal through the $K_4$ column is made possible by operating the pentenenitrile separation column ($K_2$) to keep most of the TBC byproducts out of the pentenenitrile separation column overheads.

Example 18

Ligand Hydrolysis Products

Example 2 is repeated. The catalyst in the first, second and third reactions zones ($Z_1$, $Z_2$ and $Z_3$) contains a bidentate phosphite ligand.

A portion of the bidentate ligand in the first reaction zone ($Z_1$) catalyst loop reacts with water to form light ligand hydrolysis product (LLHP) and heavy ligand hydrolysis product (HLHP). The purge from the catalyst loop is contacted in the extraction system. The raffinate (polar) phase from the extraction system is charged to separation section 1000. The LLHP is removed from the system via the overheads 420 of $K_4$ and the HLHP is removed from the system via line 540 from $K_3$.

Example 19

Removal of Ligand Hydrolysis Products

Example 3 is repeated. The catalyst in the first and second reaction zones ($Z_1$ and $Z_2$) contains a monodentate phosphite ligand and the catalyst in the third reaction zone ($Z_3$) contains a bidentate phosphite ligand.

A portion of the bidentate ligand in the first reaction zone ($Z_1$) catalyst loop reacts with water to form light ligand hydrolysis product (LLHP) and heavy ligand hydrolysis product (HLHP). The purge from the catalyst loop is contacted in the extraction system.

The raffinate (polar) phase from the extraction system is charged to separation section 1000. The LLHP is removed from the system via the overheads 420 of $K_4$ and the HLHP is removed from the system via line 540 from $K_3$.

Example 20

Removal of MGN Through Liquid-Liquid Extraction

Example 3 is repeated. The crude product of the first reaction zone principally contains pentenenitriles and unreacted 1,3-butadiene, but also contains a minor portion of dinitriles including adiponitrile (ADN) and methylglutaronitrile (MGN).

The catalyst flowing from the first reaction zone ($Z_1$) or the second reaction zone ($Z_2$) or both the first and second reaction zone is concentrated in one or more distillation columns and recycled in at least one catalyst recycle stream to the first reaction zone ($Z_1$) or the second reaction zone ($Z_2$) or both the first and second reaction zone ($Z_1$ and $Z_2$).

At least a portion of the catalyst recycle stream is contacted with an extraction solvent in a liquid/liquid extraction step to produce a solvent phase and a raffinate phase. The solvent phase comprises extraction solvent and catalyst and the raffinate phase comprises the dinitrile compounds comprising MGN, compounds with a higher boiling point than the dinitrile compounds and compounds with a lower boiling point than the dinitrile compounds. The catalyst from the solvent phase obtained in the liquid/liquid extraction step is then recycled to the first reaction zone or the second reaction zone or both the first and second reaction zone.

Example 21

Isolating the First and Second Reaction Zones from the Lewis Acid of the Third Reaction Zone Example 3 is repeated except that $ZnCl_2$ (Lewis acid) from the third reaction zone $Z_3$ is charged back to the first reaction zone ($Z_1$). The crude product from the first reaction zone ($Z_1$) is continuously monitored for dinitrile content. Several minutes after the control valve is partially opened to charge the Lewis acid from the third reaction zone back to the first reaction zone at a concentration of about 100 ppm of zinc, based on total catalyst charged to the first reaction zone, the control valve is opened further to increase the zinc charge to the first reaction zone to about 500 ppm. At 100 ppm zinc, the crude product contains about 0.5% by weight MGN. Increasing the Lewis acid charge to 500 ppm increases the production of MGN to about 1.0% by weight of crude product from the first reaction zone ($Z_1$).

Example 22

Zinc Chloride in the Extraction Solvent

Example 1 is repeated. The cyclohexane extraction from the shared catalyst extraction system is analyzed for Zn as taught in U.S. Pat. No. 3,778,809 to Walter.

About 100 ppm of Zn in the recycled catalyst correlates with about 0.8% MGN yield. Increasing the Zn level in the recycled catalyst by another 100 ppm increases the MGN yield by another 0.5% for a total of 1.3% (weight).

Example 23

Adiponitrile is produced by the two-step hydrocyanation of 1,3-butadiene by reacting in a first reaction zone a mixture comprising 1,3-butadiene (BD) and hydrogen cyanide (HCN) in the presence of a first catalyst comprising zero-valent Ni and a first phosphorus-containing ligand to produce a reaction product comprising 3-pentenenitrile (3PN) and 2-methyl-3-butenenitrile (2M3BN).

At least a portion of the 2M3BN from the first reaction zone is isomerized in a second reaction zone in the presence of a second catalyst comprising zero-valent Ni and a second phosphorus-containing ligand to produce reaction product comprising 3PN.

A mixture comprising 3PN from the second reaction zone and hydrogen cyanide (HCN) is reacted in the presence of a third catalyst comprising zero-valent Ni and a third phosphorus-containing ligand and in the presence of Lewis acid promoter to produce a reaction product comprising adiponitrile.

The catalyst flows through the first, second and third reaction zones along with reactants and products.

The first catalyst is recycled to the first reaction zone through a first catalyst recycle loop.

The third catalyst is recycled to the third reaction zone through a separate catalyst recycle loop.

The catalyst recycle loops for recycling the first and third catalysts are different.

A portion of the first catalyst concentrated in the first recycle loop of the first stage is purified by a liquid/liquid extraction step.

Purified first catalyst is returned to the first reaction zone.

Example 24

The process of Example 23 is repeated with additional steps. In this Example 24, the separate catalyst recycle loops for recycling the first and third catalysts comprise one or more distillation apparatus for concentrating catalyst, and the distillation apparatus of the separate catalyst recycle loops are different.

Example 25

The process of Example 24 is repeated with additional steps. A portion of the concentrated first catalyst in the first catalyst recycle loop is purged by taking a purge stream from the first catalyst recycle loop. The first catalyst in the purge stream is purified and at least a portion of the purified first catalyst is returned to the first reaction zone.

Example 26

The process of Example 25 is repeated with additional steps. The purge stream from the first catalyst recycle loop is passed into a first liquid/liquid extraction zone along with a dinitrile stream and a solvent extraction stream. The liquids in the extraction zone are separated into an extraction solvent phase comprising the first catalyst and raffinate phase comprising dinitriles.

Example 27

The process of Example 26 is repeated with additional steps. The extraction solvent phase from the first liquid/liquid extraction zone is distilled to provide the purified catalyst which is returned to the first reaction zone.

Example 28

The process of Example 27 is repeated with additional steps. The raffinate phase comprises extraction solvent, pentenenitriles, dintiriles and catalyst degradation products. The extraction solvent, pentenenitriles, dintiriles and catalyst degradation products are separated from one another, and dinitriles are recycled to the first liquid/liquid extraction zone.

Example 29

The process of Example 28 is repeated with additional steps. At least a portion of the raffinate phase is passed to an adiponitrile product recovery section for recovering adiponitrile produced in a third reaction zone ($Z_3$).

Example 30

The process of Example 29 is repeated. At least a portion of the raffinate phase is passed to a dinitrile recycle loop, which is different from the adiponitrile product recovery section for recovering adiponitrile produced in the third reaction zone ($Z_3$).

Example 31

The process of Example 30 is repeated with additional steps. Effluent from third reaction zone ($Z_3$) is fed to a separate liquid/liquid extraction zone which is different from the first liquid/liquid extraction zone. An extraction solvent is also fed to the separate liquid/liquid extraction zone. The liquids in the separate liquid/liquid extraction zone are separated into an extraction solvent phase comprising the third catalyst and a raffinate phase comprising dinitriles.

Example 32

The process of Example 31 is repeated with additional steps. The extraction solvent phase from the separate liquid/liquid extraction zone is distilled to provide purified third catalyst which is recycled to the third reaction zone ($Z_3$).

Example 33

The process of Example 32 is repeated with additional steps. The raffinate phase from the separate liquid/liquid extraction zone is passed from the separate liquid/liquid extraction zone into an adiponitrile product recovery section, wherein extraction solvent, pentenenitriles, dintiriles and catalyst degradation products are separated from one another. The adiponitrile is further separated from other dinitriles, and is recovered.

Example 34

The process Example 33 is repeated with additional steps. A portion of the adiponitrile recovered in the adiponitrile product recovery section is recycled to the first liquid/liquid extraction zone.

Example 35

The process of Example 34 is repeated with additional features. The first phosphorus-containing ligand is a monodentate phosphorus-containing ligand. The second phosphorus-containing ligand is a monodentate phosphorus-containing ligand or a bidentate phosphorus-containing ligand. The third phosphorus-containing ligand is a bidentate phosphorus-containing ligand.

Example 36

The process of Example 35 is repeated with additional features. The second phosphorus-containing ligand is a monodentate phosphorus-containing ligand. The first phosphorus-containing ligand and the second phosphorus-containing ligand are the same.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also the individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±8%, or ±10%, of the numerical value(s) being modified. In addition, the phrase "about 'x' to 'y'" includes "about 'x' to about 'y'".

While the illustrative embodiments of the invention have been described with particularity, it will be understood that the invention is capable of other and different embodiments and that various other modifications will be apparent to and may be readily made by those skilled in the art without departing from the spirit and scope of the invention. Accordingly, it is not intended that the scope of the claims hereof be limited to the examples and descriptions set forth herein but rather that the claims be construed as encompassing all the features of patentable novelty which reside in the present disclosure, including all features which would be treated as equivalents thereof by those skilled in the art to which the invention pertains.

What is claimed is:

1. A process for making adiponitrile, said process comprising the steps of:
    (a) reacting in a first reaction zone a mixture comprising 1,3-butadiene (BD) and hydrogen cyanide (HCN) in the presence of a first catalyst comprising zero-valent Ni and a first phosphorus-containing ligand to produce a reaction product comprising 3-pentenenitrile (3PN) and 2-methyl-3-butenenitrile (2M3BN);
    (b) isomerizing at least a portion of the 2M3BN of step (a) in a second reaction zone in the presence of a second catalyst comprising zero-valent Ni and a second phosphorus-containing ligand to produce a reaction product comprising 3PN; and
    (c) reacting in a third reaction zone a mixture comprising 3PN from step (b) and hydrogen cyanide (HCN) in the presence of a third catalyst comprising zero-valent Ni and a third phosphorus-containing ligand and in the presence of Lewis acid promoter to produce a reaction product comprising adiponitrile,
    wherein the first catalyst flows through the first, second and third reaction zone along with reactants and products,
    wherein the second catalyst flows through the second reaction zone along with reactants and products,
    wherein the third catalyst flows through the third reaction zone along with reactants and products,
    wherein the first catalyst is recycled to the first reaction zone through a first catalyst recycle loop,
    wherein the third catalyst is recycled to the third reaction zone through a separate catalyst recycle loop,
    wherein the catalyst recycle loops for recycling the first and third catalysts are different,
    wherein a portion of the first catalyst concentrated in the first recycle loop is purified by a liquid/liquid extraction step, and
    wherein purified first catalyst is returned to the first reaction zone.

2. The process of claim 1, wherein the separate catalyst recycle loops for recycling the first and third catalysts comprise one or more distillation apparatus for concentrating catalyst, and wherein the distillation apparatus of the separate catalyst recycle loops are different.

3. The process of claim 1, wherein a portion of the concentrated first catalyst in the first catalyst recycle loop is purged by taking a purge stream from the first catalyst recycle loop, wherein first catalyst in the purge stream is purified, and wherein at least a portion of the purified first catalyst is returned to the first reaction zone.

4. The process of claim 3, wherein the purge stream from the first catalyst recycle loop is passed into a first liquid/liquid extraction zone along with a dinitrile stream and a solvent extraction stream, wherein the liquids in the extraction zone are separated into an extraction solvent phase comprising the first catalyst and a raffinate phase comprising dinitriles.

5. The process of claim 4, wherein the extraction solvent phase from the first liquid/liquid extraction zone is distilled to provide the purified catalyst which is returned to the first reaction zone.

6. The process of claim 4, wherein the raffinate phase comprises extraction solvent, pentenenitriles, dintiriles and catalyst degradation products, wherein extraction solvent, pentenenitriles, dintiriles and catalyst degradation products are separated from one another, and dinitriles are recycled to the first liquid/liquid extraction zone.

7. The process of claim 4, wherein at least a portion of the raffinate phase is passed to an adiponitrile product recovery section for recovering adiponitrile produced in the third reaction zone.

8. The process of claim 4, wherein at least a portion of the raffinate phase is passed to a dinitrile recycle loop, which is different from the adiponitrile product recovery section for recovering adiponitrile produced in the third reaction zone.

9. The process of claim 8, wherein an effluent from third reaction zone is fed to a separate liquid/liquid extraction zone which is different from the first liquid/liquid extraction zone, wherein an extraction solvent is also fed to the separate liquid/liquid extraction zone, and wherein the liquids in the separate liquid/liquid extraction zone are separated into an extraction solvent phase comprising the third catalyst and a raffinate phase comprising dinitriles.

10. The process of claim 9, wherein the extraction solvent phase from the separate liquid/liquid extraction zone is distilled to provide purified third catalyst which is recycled to the third reaction zone.

11. The process of claim 10, wherein the raffinate phase from the separate liquid/liquid extraction zone is passed from the separate liquid/liquid extraction zone into an adiponitrile product recovery section, wherein extraction solvent, pentenenitriles, dintiriles and catalyst degradation products are separated from one another, wherein adiponitrile is further separated from other dinitriles, and wherein adiponitrile is recovered.

12. The process of claim 11, wherein a portion of the adiponitrile recovered in the adiponitrile product recovery section is recycled to the first liquid/liquid extraction zone.

13. The process of claim 1, wherein the first phosphorus-containing ligand is a monodentate phosphorus-containing ligand, wherein the second phosphorus-containing ligand is a monodentate phosphorus-containing ligand or a bidentate phosphorus-containing ligand, and wherein the third phosphorus-containing ligand is a bidentate phosphorus-containing ligand.

14. The process of claim 13, wherein the second phosphorus-containing ligand is a monodentate phosphorus-containing ligand, and wherein the first phosphorus-containing ligand and the second phosphorus-containing ligand are the same.

15. The process of claim 1, wherein said first phosphorus-containing ligand, said second phosphorus-containing ligand and said third phosphorus-containing ligand are selected from the group consisting of a monodentate or bidentate phosphite ligand, a monodentate or bidentate phosphine ligand, a monodentate or bidentate phosphonite ligand, a monodentate or bidentate phosphinite ligand, and a mixture of these ligands.

16. The process of claim 1, wherein the first phosphorus-containing ligand of the catalyst which flows through the first reaction zone is a monodentate phosphorus-containing ligand, and
wherein the second phosphorus-containing ligand is the same as the first phosphorus-containing ligand.

17. The process of claim 16, wherein said first phosphorus-containing ligand and said second phosphorus-containing ligand is at least one ligand of Formula I,
where Formula I is $$P(OR^2)(OR^3)(OR^4) \qquad (I)$$

where $R^2$, $R^3$ and $R^4$ are the same or different and are aryl groups, where the aryl groups are each optionally substituted with up to four alkyl groups, each alkyl group having from 1-4 carbon atoms.

18. The process of claim 17, wherein $R^2$, $R^3$ and $R^4$ are the same or different phenyl or tolyl groups.

19. The process of claim 18, wherein the phosphorus-containing ligand of Formula I is one or more ligands selected from the group consisting of (o-tolyl-O—)₃P, (p-tolyl-O—)(phenyl-O—)₂P, (m-tolyl-O—)(phenyl-O—)₂P, (o-tolyl-O—)(phenyl-O—)₂P, (p-tolyl-O—)₂(phenyl-O—)P, (m-tolyl-O—)₂(phenyl-O—)P, (o-tolyl-O—)₂(phenyl-O—)P, (m-tolyl-O—)(p-tolyl-O—)(phenyl-O—)P, (o-tolyl-O—)(p-tolyl-O—)(phenyl-O—)P, (o-tolyl-O—)(m-tolyl-O—)(phenyl-O—)P, (p-tolyl-O—)₃P, (m-tolyl-O—)(p-tolyl-O—)₂P, (o-tolyl-O—)(p-tolyl-O—)₂P, (m-tolyl-O—)₂(p-tolyl-O—)P, (o-tolyl-O—)₂(p-tolyl-O—)P, (o-tolyl-O—)(m-tolyl-O—)(p-tolyl-O—)P, (m-tolyl-O—)₃P, (o-tolyl-O—)(m-tolyl-O—)₂P, and (o-tolyl-O—)₂(m-tolyl-O—)P.

20. The process of claim 15, wherein said Lewis acid promoter is an inorganic compound or an organometallic compound comprising a cation of a metal selected from the group consisting of scandium, titanium, vanadium, chromium, manganese, iron, cobalt, copper, zinc, boron, aluminum, yttrium, zirconium, niobium, molybdenum, cadmium, rhenium, lanthanum, erbium, ytterbium, samarium, tantalum, and tin.

21. The process of claim 15, wherein said Lewis acid promoter is selected from the group consisting of salts of metals having atomic numbers 13, 21-32, 39-50, and 57-80 and compounds of the formula BR'₃ wherein R' is an alkyl or an aryl radical of up to 18 carbon atoms.

22. The process of claim 21, wherein said Lewis acid promoter comprises ZnCl₂ or triphenylboron.

* * * * *